US012678503B2

(12) United States Patent
Lee et al.

(10) Patent No.: US 12,678,503 B2
(45) Date of Patent: Jul. 14, 2026

(54) WATER-ACTIVATED MUCOADHESIVE COMPOSITIONS AND METHODS OF DELIVERING BIOLOGICALLY ACTIVE SUBSTANCES

(71) Applicant: The Brigham and Women's Hospital, Inc., Boston, MA (US)

(72) Inventors: Yuhan Lee, Cambridge, MA (US); Ali Tavakkoli, Boston, MA (US); Jeffrey M. Karp, Brookline, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 816 days.

(21) Appl. No.: 17/617,785

(22) PCT Filed: Jun. 10, 2019

(86) PCT No.: PCT/US2019/036423
§ 371 (c)(1),
(2) Date: Dec. 9, 2021

(87) PCT Pub. No.: WO2020/251545
PCT Pub. Date: Dec. 17, 2020

(65) Prior Publication Data
US 2022/0226475 A1 Jul. 21, 2022

(51) Int. Cl.
| *A61K 47/30* | (2006.01) |
| *A61K 9/00* | (2006.01) |
| *A61K 45/06* | (2006.01) |
| *A61K 47/36* | (2006.01) |

(52) U.S. Cl.
CPC ............ *A61K 47/30* (2013.01); *A61K 9/0095* (2013.01); *A61K 45/06* (2013.01); *A61K 47/36* (2013.01)

(58) Field of Classification Search
None
See application file for complete search history.

(56) References Cited

U.S. PATENT DOCUMENTS

| | | | |
|---|---|---|---|
| 3,432,489 | A | 3/1969 | Nitta et al. |
| 4,522,811 | A | 6/1985 | Eppstein et al. |
| 4,866,856 | A | 9/1989 | Feeley |
| 4,885,281 | A | 12/1989 | Hanstein et al. |
| 5,013,557 | A | 5/1991 | Tai |
| 5,246,697 | A | 9/1993 | Conte et al. |
| 5,294,434 | A | 3/1994 | King et al. |
| 5,321,013 | A | 6/1994 | Zagnoli et al. |
| 5,464,828 | A | 11/1995 | Katayama et al. |
| 5,563,258 | A | 10/1996 | Ochi et al. |
| 5,595,977 | A | 1/1997 | Dyrsting et al. |
| 5,661,137 | A | 8/1997 | Zagnoli |
| 5,718,923 | A | 2/1998 | Matsuda et al. |
| 5,968,906 | A | 10/1999 | Kashimura et al. |
| 6,319,518 | B1 | 11/2001 | Lee et al. |
| 6,391,294 | B1 | 5/2002 | Dettmar et al. |
| 6,391,860 | B1 | 5/2002 | McGrath |
| 6,555,137 | B1 | 4/2003 | Yamazaki et al. |
| 6,773,722 | B2 | 8/2004 | Zagnoli et al. |
| 10,716,802 | B2 | 7/2020 | Karp et al. |
| 10,973,846 | B2 | 4/2021 | Karp et al. |
| 11,433,094 | B2 | 9/2022 | Karp et al. |
| 11,524,024 | B2 | 12/2022 | Karp et al. |
| 2002/0068088 | A1 | 6/2002 | Gruber et al. |
| 2007/0190139 | A1 | 8/2007 | Zerbe et al. |
| 2008/0319230 | A1 | 12/2008 | Sigl et al. |
| 2009/0196896 | A1 | 8/2009 | Patton et al. |
| 2010/0172967 | A1 | 7/2010 | Nemoto et al. |
| 2011/0021455 | A1 | 1/2011 | Chesnoy et al. |
| 2011/0229556 | A1 | 9/2011 | Irvine et al. |
| 2012/0039981 | A1 | 2/2012 | Pedersen et al. |
| 2012/0064139 | A1 | 3/2012 | McGrath et al. |
| 2013/0274209 | A1 | 10/2013 | Colombo |
| 2016/0022729 | A1 | 1/2016 | Karp et al. |
| 2020/0046754 | A1 | 2/2020 | Karp et al. |
| 2020/0289546 | A1 | 9/2020 | Karp et al. |
| 2021/0236538 | A1 | 8/2021 | Karp et al. |
| 2022/0226475 | A1 | 7/2022 | Karp et al. |
| 2023/0141842 | A1 | 5/2023 | Karp et al. |

FOREIGN PATENT DOCUMENTS

| | | |
|---|---|---|
| CA | 2067070 | 10/1992 |
| EP | 0511703 | 11/1992 |
| EP | 0245855 | 1/1993 |
| EP | 0437406 | 3/1993 |
| EP | 2482822 | 8/2012 |
| RU | 2422133 | 6/2011 |
| WO | WO 1989/005645 | 6/1989 |
| WO | WO 2011/041509 | 4/2011 |
| WO | WO 2014/151565 | 9/2014 |
| WO | WO 2017/053970 | 3/2017 |

OTHER PUBLICATIONS

IN Office Action in Indian Appln. No. 202217001272, mailed on Feb. 1, 2024, 7 pages.

EP Extended Search Report in European Appln. No. 19932383.3, dated Apr. 11, 2023, 10 pages.

Beheshti et al., "Comparison of topical sucralfate and silver sulfadiazine cream in second degree burns in rats," Adv Clin Exp Med, 2013, 22: 481-487.

Cancer.gov, "Gastrointestinal tract," retrieved Oct. 23, 2021 from URL https://www.cancer.gov/publications/dictionaries/cancer-terms/def/gastrointestinal-tract, 2 pages.

chemicalprocessing.com [online]. "Marion Mixers: Comparing Microwave to Conventional Heating and Drying Systems," dated Jun. 12, 2015 [retrieved on Nov. 22, 2016]. Retrieved from the Internet <URL:http://www.chemicalprocessing.com/assets/wp_downloads/pdf/comparing-microwave-tocovnetional-heating-drying-systems-v2.pdf> 7 pages.

(Continued)

*Primary Examiner* — Katherine Peebles

*Assistant Examiner* — Afua Bamfoaa Boateng

(74) *Attorney, Agent, or Firm* — Fish & Richardson P.C.

(57) ABSTRACT

This disclosure relates to compositions including formulated sucralfate or other aluminum-crosslinked sulfated agents and one or more biologically active substances to mucosal surfaces within the GI tract and methods for the manufacture and the use of these compositions.

20 Claims, 27 Drawing Sheets

(56)                    References Cited

OTHER PUBLICATIONS

Couzin, "Bypassing Medicine to Treat Diabetes," Science, 2008, 320: 438-440.

Cummings and Flum, "Gastrointestinal Surgery as a Treatment for Diabetes," J. Am. Med. Assoc., 2008, 299: 341-343.

De Kruif et al., "Complex coacervation of proteins and anionic polysaccharides," Current Opinion in Colloid & Interface Science, Dec. 1, 2004, 9(5):340-9.

en.wikipedia.org [online]. "Freeze-drying," dated Sep. 18, 2015 [retrieved on Nov. 22, 2016], Retrieved from the Internet <URL: https://en.wikipedia.org/w/index.php?title=Freezedrying&oldid-681682674> 7 pages.

en.wikipedia.org [online]. "Coacervate," dated May 20, 2015 [retrieved on Nov. 22, 2016]. Retrieved from the Internet <URL:https://en.wikipedia.org/w/index.php?title=Coacervate&oldid=663181907> 2 pages.

en.wikipedia.org [online]. "List of water-miscible solvents," dated Mar. 31, 2015 [retrieved on Nov. 22, 2016]. Retrieved from the Internet <URL:https://en.wikipedia.org/w/index.php?title=list_ofwater-miscible_solvents&oldid=654319850> 3 pages.

en.wikipedia.org [online]. "Propylene glycol," dated Sep. 19, 2015 [retrieved on Nov. 22, 2016]. Retrieved from the Internet <URL:https://en.wik1pedia.org/w/index.php?title=Propylene_glycol&oldid=681710532> 7 pages.

EP Extended European Search Report in Application No. 16849871.5, dated May 7, 2019, 10 pages.

EP Office Action in European Appln. No. 16849871, dated Jun. 24, 2020, 8 pages.

Fuhrmann et al., "Sustained gastrointestinal activity of dendronized polymer-enzyme conjugates," Nature Chemistry, Jul. 2013, 5(7):582-9.

Gersin et al., "Open-label, sham-controlled trial of an endoscopic duodenojejunal bypass liner for preoperative weight loss in bariatric surgery candidates," Gastrointest. Endosc. 2010, 71: 976-82.

Gupta et al., "Topical Sucralfate Treatment of Anal Fistulotomy Wounds: A Randomized Placebo-Controlled Trial," Diseases of the Colon & Rectum, 2011, 54: 699-704.

Hem et al., "Form and stability of aluminum hydroxide complexes in dilute solution," Geological Survey Water-Supply Paper, Jan. 1967, 60 pages.

Higo et al., "A novel evaluation method of gastric mucoadhesive property in vitro and the mucoadhesive mechanism of tetracycline-sucralfate acidic complex for eradication of Helicobacter pylori," Pharmaceutical Research, Mar. 2004, 21(3):413-9.

Higo et al., "A Novel Evaluation Method of Gastric Mucoadhesive Property in Vitro and the Mucoadhesive Mechanism of Tetracycline-Sucralfate Acidic Complex for Eradication of Helicobacter pylori," Pharm. Res, 2004, 21: 413-419.

Lee et al., "Therapeutic luminal coating of the intestine, " Nature Materials, Sep. 1, 2018, 17(9):834-42.

Malbert et al., "Duodenal Bulb Control of the Flow Rate of Digesta in the Fasted and Fed Dog," J. Physiol., 1989, 409:371-384.

Markham et al., "Topical sucralfate for erosive irritant diaper dermatitis," Archives of Dermatology, 2000, 136: 1199-200.

Nail et al., "Structure of aluminum hydroxide gel I: initial precipitate," Journal of Pharmaceutical Sciences, Aug. 1976, 65(8):1188-91.

New et al., "Assessing the prevalence, monitoring and management of chronic kidney disease in patients with diabetes compared with those without diabetes in general practice," Diabetic Medicine, 2007, 24: 364-369.

Ochi, "Chemistry of Sucralfate" in Sucralfate: From Basic Science to the Bedside, Chapter 5, 1995, pp. 53 and 55.

PCT International Preliminary Report on Patentability in International Application No. PCT/US2014/26007, dated Sep. 15, 2015, 9 pages.

PCT International Preliminary Report on Patentability in International Application No. PCT/US2016/053781, mailed on Mar. 27, 2018, 8 pages.

PCT International Preliminary Report on Patentability in International Appln. No. PCT/US2019/036423, dated Dec. 14, 2021, 7 pages.

PCT International Search Report and Written Opinion in International Application No. PCT/US2014/26007, dated Jul. 7, 2014, 16 pages.

PCT International Search Report and Written Opinion in International Application No. PCT/US2016/053781, mailed on Jan. 26, 2017, 15 pages.

PCT International Search Report and Written Opinion in International Appln. No. PCT/US2019/036423, dated Aug. 27, 2019, 14 pages.

Pories et al., "Who Would Have Thought It? An Operation Proves to Be the Most Effective Therapy for Adult-Onset Diabetes Mellitus," Ann. Surg., 1995, 222: 339-350.

pueschner.com [online]. "Microwave Vacuum Drying for advanced Process Technology," Oct. 29, 2012 [retrieved on Nov. 22, 2016). Retrieved from the Internet <URL:http://www.pueschner.com/downloads/vacuumdrying.pdf> 8 pages.

Ritz et al., "Nephropathy in patients with type 2 diabetes mellitus," New Engl. J. Med., 1999, 341: 1127-1133.

Rubino et al., "Potential of Surgery for Curing Type 2 Diabetes Mellitus," Ann. Surg., 2002, 236: 554-559.

Schouten et al., "A multi-center, randomized efficacy study of the EndoBarrier™ Gastrointestinal Liner for pre-surgical weight loss prior to bariatric surgery," Ann. Surg., 2010, 251(2), 236-243.

Slomiany et al., "Enhancement of the protective qualities of gastric mucus by sucralfate: Role of phosphoinositides," Am. J. of Med., 1991, 91: 30S-36S.

Tasman-Jones et al., "Sucralfate interactions with gastric mucus," Am. J. Med., 1989, 86: 5-9.

US Office Action in U.S. Appl. No. 14/776,594, dated Jan. 18, 2017, 12 pages.

US Office Action in U.S. Appl. No. 14/776,594, dated Nov. 28, 2017, 12 pages.

US Office Action in U.S. Appl. No. 14/776,594, dated May 8, 2019, 13 pages.

US Office Action in U.S. Appl. No. 15/763,018, dated Aug. 19, 2020, 29 pages.

Veis et al., "Phase separation in polyelectrolyte systems. I. Complex coacervates of gelatin," The Journal of Physical Chemistry, Sep. 1960, 64(9):1203-10.

Wang et al., "The polyelectrolyte complex/coacervate continuum," Macromolecules, May 13, 2014, 47(9):3108-16.

Zelikin et al., "Materials and methods for delivery of biological drugs," Nature Chemistry, Nov. 2016, 8(11):997-1007.

Zhang et al., "A pH-responsive supramolecular polymer gel as an enteric elastomer for use in gastric devices," Nature Materials, Oct. 2015, 14(10):1065, 20 pages.

Zuidam et al., "Overview of Microencapsulates for Use in Food Products or Processes and Methods to Make Them" in Encapsulation Technologies for Active Food Ingredients and Food Processing, Chapter 2, 2010, p. 15.

CN Office Action in Chinese Appln. No. 201980099194.6, mailed on Aug. 25, 2023, 18 pages (with English translation).

KR Office Action in Korean Appln. No. 10-2022-7000322, mailed on Sep. 19, 2024, 20 pages (with English translation).

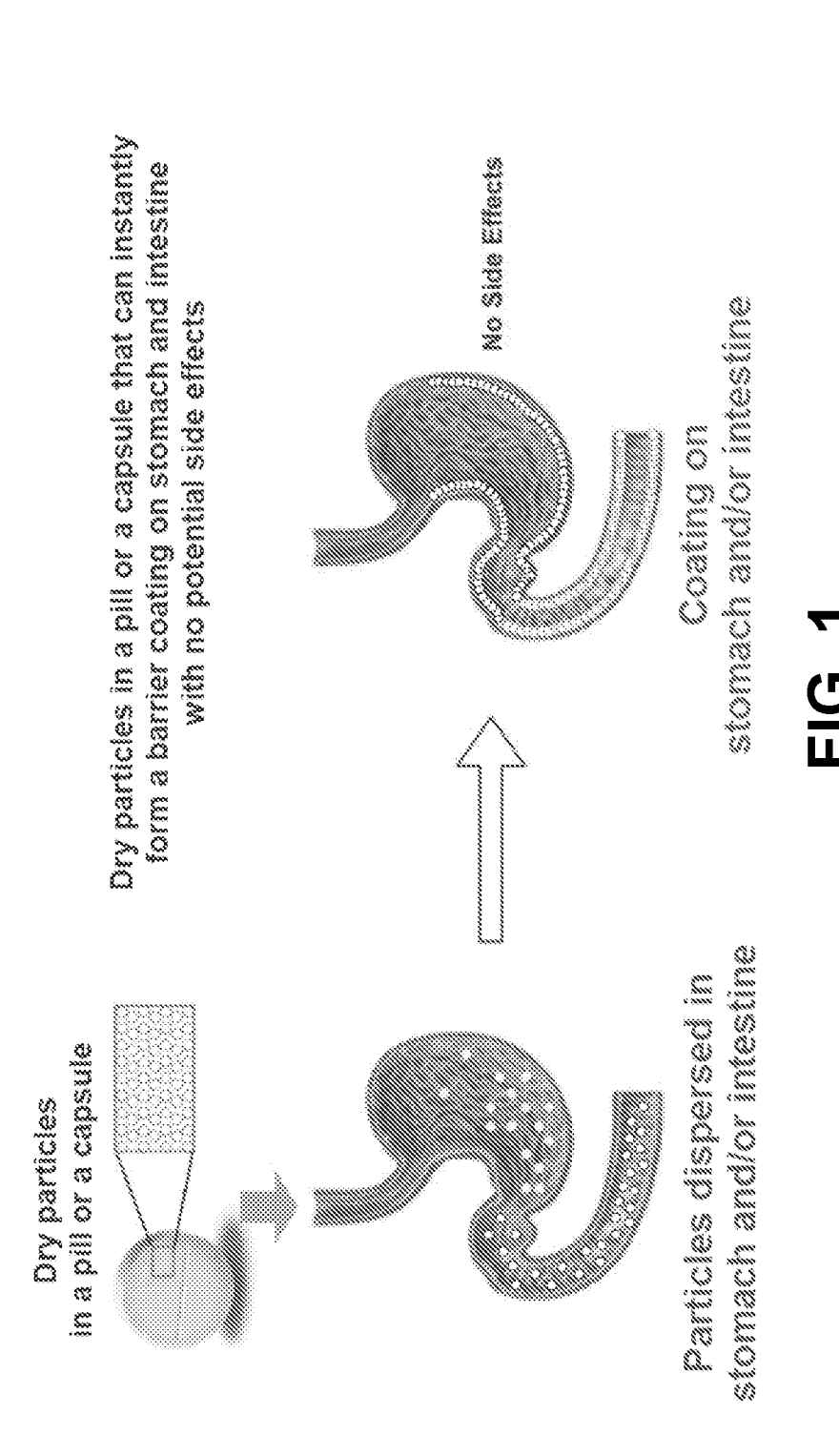

AF-LuCl particles that can be orally delivered and instantly form a barrier coating on stomach and intestine Dry particles in a pill or a capsule that can instantly form a barrier coating on stomach and intestine with no potential side effects Dry particles in a pill or a capsule No Side Effects Particles dispersed in stomach and/or intestine Coating on stomach and/or intestine

FIG. 1

Sticky acidified sucralfate paste can be formulated into non-sticky particles using water soluble solvents. The particles can be rehydrated using water to form sticky paste similar to the original acidified sucralfate paste.

High MW PAC
(in Sucralfate)

2H⁺ + 2H₂O

Strong Acid
(> 0.3N HCl)

FIG. 4B

Low MW PAC
(in LuCl)

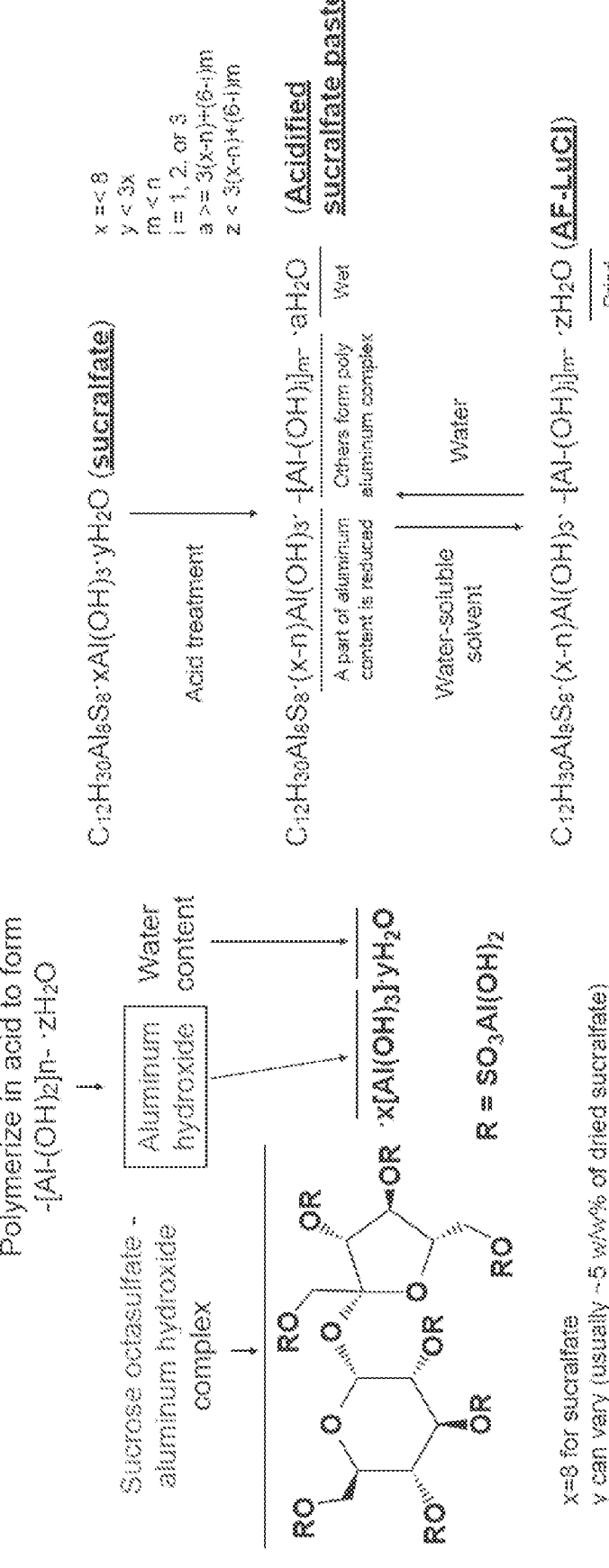

Aluminum hydroxide in sucralfate polymerize in acid to form acidified sucralfate paste and further dehydrate in solvents Polymerize in acid to form
$-[Al-(OH)_2]_n- \cdot zH_2O$ Sucrose octasulfate - aluminum hydroxide complex Aluminum hydroxide Water content $\cdot x[Al(OH)_3] \cdot yH_2O$ $R = SO_3Al(OH)_2$ x=8 for sucralfate
y can vary (usually ~5 w/w% of dried sucralfate)

Chemical Structure of Sucralfate

FIG. 4C

$C_{12}H_{30}Al_8S_8 \cdot xAl(OH)_3 \cdot yH_2O$ (Sucralfate)

Acid treatment $C_{12}H_{30}Al_8S_8 \cdot (x-n)Al(OH)_3 \cdot -[Al-(OH)_i]_m- \cdot aH_2O$ — Wet A part of aluminum content is reduced | Others form poly aluminum complex Water-soluble solvent | Water $C_{12}H_{30}Al_8S_8 \cdot (x-n)Al(OH)_3 \cdot -[Al-(OH)_i]_m- \cdot zH_2O$ (AF-LuCl)

Dried (z < a)

x =< 8
y < 3x
m < n
i = 1, 2, or 3
a >= 3(x-n)+(6-i)m
z < 3(x-n)+(6-i)m (Acidified sucralfate paste)

FIG. 4D

Amount of aluminum released: AF-LuCls release significantly low aluminum after exposure to SGF (pH 1.0)

Aluminum release after exposure to simulated gastric fluid (pH 1.0)

*** (p<0.0001)

Native Paste
LuCl0.3
LuCl0.4
LuCl0.5

AF-LuCl

Sucralfate

*** 1-way ANOVA

Released Aluminum (w/w%)

Thermogravimetric analysis (TGA) thermal curves (a-b) of sucralfate and AF-LuCl, and their first derivative curves (c-d)

Ability to flow and form a film: AF-LuCls can flow and form stable films of 100-300um in thickness on mucus surface The film formed from AF-LuCl on mucous substrate remains stable for multiple hours AF-LuCl film thickness change with shear stress Swelling: AF-LuCl pastes on mucus surface show low swelling in simulated body fluids Swelling of AF-LuCl paste in simulated body fluids AF-LuCl in SGF (pH 1.0)
AF-LuCl in SIF (pH 6.5)

Relative Swelling (%)

Time (min)

Barrier to Glucose: AF-LuCIs show excellent barrier function to glucose in vivo (rats)

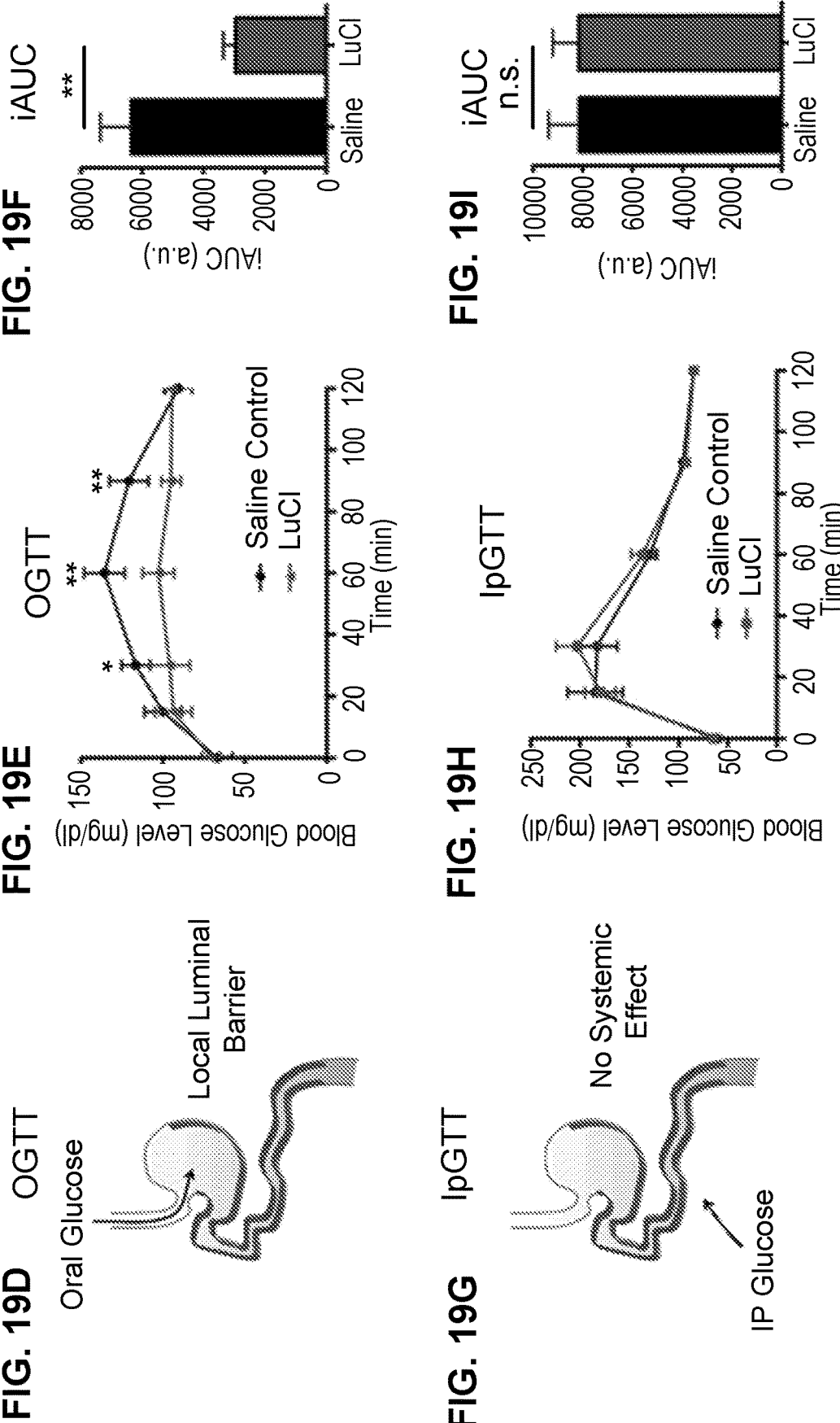

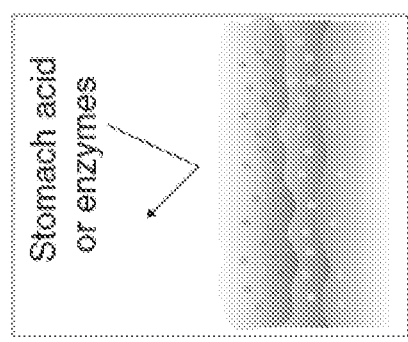
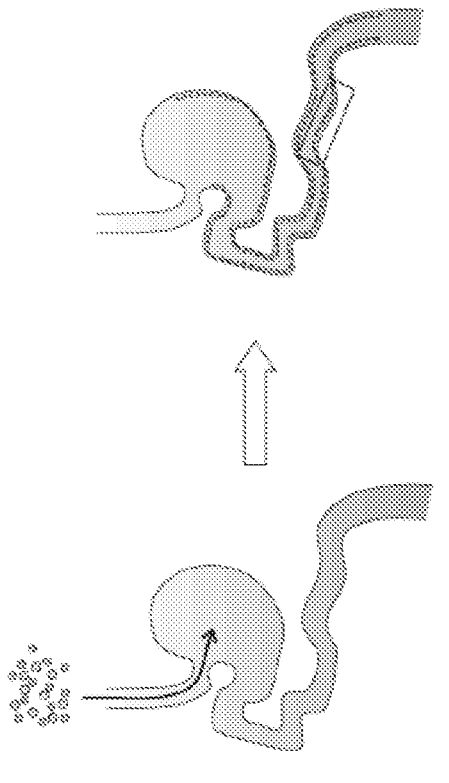
FIG. 20A

Time after the administration of LuCI
encapsulated with FITC-BSA (hr)

*100% indicates the total fluorescence in the
harvested stomach and intestine 1hr after the
administration of LuCI encapsulted with FITC-BSA

WATER-ACTIVATED MUCOADHESIVE COMPOSITIONS AND METHODS OF DELIVERING BIOLOGICALLY ACTIVE SUBSTANCES

STATEMENT OF FEDERALLY SPONSORED RESEARCH

This invention was made with government support under Grant Nos. DK084064, and GM086433 awarded by the National Institutes of Health. The government has certain rights in the invention.

CLAIM OF PRIORITY

This application is a § 371 National Stage Application of PCT/US2019/036423, filed on Jun. 10, 2019, the contents of which are hereby incorporated by reference in its entirety.

FIELD OF THE INVENTION

This disclosure relates to compositions that form coatings on mucosal surfaces, e.g., within the gastrointestinal (GI) tract, and methods of delivering biologically active substances to the GI tract for an extended duration.

BACKGROUND

The GI tract and specifically the small bowel are not only the principal site of nutrient digestion and absorption, but also one of the body's largest reservoirs of immunologically active and hormone-producing cells. As such, the intestine has been increasingly recognized as critical to the pathogenesis of systemic diseases, with substantial data highlighting the role of the small bowel as a therapeutic target for local and systemic diseases. The most notable of these observations have been data supporting the role of small intestine as a therapeutic target in type-2 diabetes (T2D).

Furthermore, many well-known diseases such as inflammatory bowel disease (IBD) affect the mucosal surface of the bowel, yet direct localized drug delivery to the affected mucosa is challenging. For the purposes of topical delivery of biologics to the distal small bowel, which is often the affected diet in patients with IBD, the main obstacles include high gastric acidity and low pH, and proteolytic gut enzymes (see, e.g., Zhang et al., "A pH-responsive supramolecular polymer gel as an enteric elastomer for use in gastric devices," Nat. Mater., 14:1065-1073 (2015) and Zelikin et al., "Materials and methods for delivery of biological drugs," Nature Chem., 8:997-1007 (2016)).

Although there have been approaches to overcome each challenge, the bioavailability of drugs such as protein drugs delivered through oral route remains too low (Fuhrmann, "Sustained gastrointestinal activity of dendronized polymer-enzyme conjugates," Nature Publishing Group, 5:582-589 (2013). As a result, these agents are given systemically, increasing their cost as well as side effects. Drug delivery systems that can directly deliver drugs to the targeted regions of the gut with minimal systemic exposure would provide significant advantages including prolonged drug efficacy, lowered dosing frequency, and decreased side effects. These diverse observations highlight the critical need to develop a therapeutic platform technology that can provide reliable access to the small bowel mucosa.

SUMMARY

The present disclosure describes water-activated mucoadhesive hydratable compositions (also referred to herein as Acid-Free Luminal Coating of the Intestine particles, abbreviated as "AF-LuCI" or "LuCI" particles) that can be utilized to deliver a wide variety of biologically active substances, e.g., one or more of these substances, to locations within the gastrointestinal (GI) tract, e.g., the small intestines, for a predefined period of time, e.g., 1 to 24 hours, e.g., 2 to 6 hours, 6 to 12 hours, 10 to 15 hours, 20 to 24 hours, or 24 to 48 hours.

In one aspect, the disclosure relates to methods of delivering a biologically active substance to at least a portion of the gastrointestinal (GI) tract of a subject, the method including orally administering to the subject a composition including a water-based liquid hydratable composition comprising one or more aluminum crosslinked sulfated agents, and at least one biologically active substance; wherein the biologically active substance is protected from acid in the subject's stomach and maintains at least some of its biological activity when present in the GI tract after passing through the subject's stomach.

In these methods, the composition can be in the dosage form of a pill, tablet, capsule, or gel-cap. In some embodiments, the dosage form degrades at a pH of fluids in the small intestine, but does not degrade at a pH of fluids in the stomach.

In various embodiments, the biologically active substance maintains at least about 10%, e.g., at least about 20%, at least about 30%, at least about 40%, at least about 50%, at least about 60%, at least about 70%, at least about 80%, at least about 90%, or at least about 95%, of its biological activity when present in the GI tract after passing through the subject's stomach.

In some embodiments, the composition is altered to allow specific distribution of the composition within the GI tract or to modulate the duration of an effect of the composition. For example, the alteration of the composition is one or more of a change in pH sensitivity of the composition, a change in size of the composition, and a change in an electrostatic charge of the composition.

In some embodiments, the one or more aluminum crosslinked sulfated agents include a complex coacervate comprising a complex of two or more oppositely charged agents where one agent is a sulfated agent.

In various embodiments, the one or more aluminum crosslinked sulfated agents are selected from the group consisting of sucralfate, sulfated dextran, sulfated dextrin, sulfated amylopectin, sulfated amylose, sulfated cellulose, carrageenan, chondroitin sulfate, glucose sulfate, sucrose sulfate, heparin, heparin sulfate, and raffinose sulfate. For example, the one or more aluminum crosslinked sulfated agents can be sucralfate.

In some embodiments, at least some amount of the biologically active substance remains in the GI tract for at least one hour. In other embodiments, at least some amount of the biologically active substance remains in the GI tract for at least one 8 hours, e.g., at least 10, 12, 15, 18, 20, 22, 24, 30, 36, 40, or 48 hours.

In some embodiments, the biologically active substance includes one or more of gene editing agents (e.g., CRIPSR systems), modified or naturally occurring bacteria (to alter the microbiome), viruses, antibiotics, cells, such as stem cells and immune cells (e.g., T cells and CAR T cells), biomolecules, small molecular drugs including immune modulating drugs (e.g., dexamethasone, hydrocortisone, and triamcinolone), antibiotics (e.g., cipfloxacin), anti-cancer drugs (e.g., doxorubicin and paclitaxel).

The biomolecule can include, for example, any one or more of an enzyme, biologics, receptor, neurotransmitter, hormone, cytokine, growth factor, chemotactic factor, antibody, vaccine, hapten, toxin, small molecule, neutraceutical, vitamin, interferon, ribozyme, antisense agent, plasmid, DNA, and RNA. For example, the small molecule can include one or more of an anti-inflammatory agent, an analgesic, an antimicrobial agent, a steroid, a stem cell activating molecule, and a regenerative therapeutic agent.

In some embodiments, the biologically active substance can be or include one or more of the following therapeutic agents: insulin, metformin, sulfonylurea, alpha-glucosidase inhibitor, thiazolidinediones, amylin analog, bile acid sequestrant, DPP-4 inhibitors, dopamine agonist, incretin mimetics, non-sulfonylurea secretagogues, and meglinitides, orlistat, lorcaserin, sibutramine, rimonabant, metformin, exenatide, pramlintide, and topiramate/phentermine.

In another aspect, the disclosure includes use of any of the compositions as described herein in method to treat one or more disorders or diseases, e.g., as described herein. For example, the compositions can be used for the treatment of Crohn's disease, by administering the composition to a subject in need thereof, wherein the one or more biologically active substances are selected from the group consisting of: aminosalicylates, corticosteroids, immunomodulators, antibiotics, and biologics, include adalimumab, adalimumab-adbm, adalimumab-atto, certolizumab, infliximab, infliximab-abda, infliximab-dyyb, natalizumab, ustekinumab, and vedolizumab.

In another aspect, the disclosure includes method or uses of the composition as described herein for the treatment of rheumatoid arthritis, by administering the composition to a subject in need thereof, wherein the one or more biologically active substances are selected from the group consisting of: biologics including abatacept, adalimumab, adalimumab-adbm, adalimumab-atto, anakinra, certolizumab, etanercept, etanercept-szzs, golimumab, infliximab, infliximab-abda, infliximab-dyyb, rituximab, and tocilizumab.

The compositions include one or more aluminum crosslinked sulfated agents that can form a paste following contact with an aqueous liquid in the absence of acid. In another aspect, the disclosure relates to hydratable compositions, e.g., in a dry form, that include the biologically active substance, such as biomolecules, in particles each including one or more aluminum crosslinked sulfated agents that can form a paste following contact with an aqueous liquid in the absence of acid. In some embodiments, the compositions used in the new methods include a complex coacervate having a complex of two or more oppositely charged agents where one agent is a sulfated agent. The biologically active substances form a physical mixture with the compositions and non-covalent interactions, e.g., ionic interactions and hydrogen bonding, form between the biologically active substances and the water-based, liquid hydratable compositions.

In some embodiments, these compositions can have the following chemical structure:

$$C_{12}H_{30}Al_8S_8O_{51} \cdot x[Al(OH)_i] \cdot zH_2O$$

wherein x is less than or equal to 8;
i=1, 2, or 3; and
z<x·i.

The sulfated agents in these hydratable compositions can include any one or more of, consist essentially of, or can be selected from the group consisting of sucralfate, sulfated dextran, sulfated dextrin, sulfated amylopectin, sulfated amylose, sulfated cellulose, carrageenan, chondroitin sulfate, glucose sulfate, sucrose sulfate, heparin, heparin sulfate, and raffinose sulfate.

The hydratable compositions can include a non-aqueous liquid carrier and when rehydrated, the viscous liquid composition can have a viscosity in the range of 1 to 1000 Pascal-seconds (Pa·s), regardless of the pH of the liquid. The hydratable compositions can be dissolved in an amount of liquid sufficient to obtain a viscous liquid composition having a viscosity in the range of 10 to 100 Pa·s, e.g., 25 to 75 Pa·s. In various embodiments, the particles can range in size from about 0.1 to about 500 microns.

The hydratable compositions can be rehydrated by the addition of an aqueous solvent, and following hydration the particles in the composition stably adhere to a mucin coated surface under shear stress conditions. In various examples, when hydrated, the compositions form a barrier that when prepared at 10 mg/ml and applied to 1 cm$^2$ surface area cellulose nitrate filter with 0.45 micron holes in a Franz diffusion chamber exhibits less than 60% permeation of glucose 5 minutes after addition of 120 g/L glucose solution to the top chamber, and more preferably less than 40% permeation.

The hydratable compositions can release less than about 2.0 weight/weight percent of their original aluminum content in the presence of an aqueous liquid. In some embodiments, the hydratable compositions release <0.5% aluminum by weight in the presence of an aqueous liquid and when administered to a subject form an effective nutrient barrier in the gastrointestinal tract. The biologically active substance delivery properties do not appreciably change when the compositions are dried and rehydrated in the intestinal tract.

The biologically active substances include antimicrobial agents, e.g., iodine, silver ions, and chlorine, and biomolecules, e.g., any one or more of enzymes, receptors, neurotransmitters, hormones, cytokines, cell response modifiers such as growth factors and chemotactic factors, antibodies, vaccines, haptens, toxins, bacteria, small molecules, neutraceuticals, interferons, ribozymes, antisense agents, plasmids, DNA, and RNA. In some embodiments, the hydratable compositions (or the particles in the hydratable compositions) are crosslinked to the one or more biologically active substance. In some embodiments, the hydratable compositions are loaded with the one or more biologically active substances. In some embodiments, the biologically active substances are encapsulated in the hydratable composition (or in the particles of the hydratable compositions).

In various implementations, the hydratable compositions can be hydrated into a sticky paste and the paste can be dehydrated again to form the hydratable compositions.

In another aspect, the disclosure includes methods of making a stable, sulfated agent hydratable compositions that include biologically active substances. The methods include mixing a sulfated agent with an acid solution (e.g., 0.1-1.0 N HCl solution) to form a viscous ("sticky paste") precipitate; dehydrating, e.g., rapidly dehydrating, the precipitate by mixing (e.g., by vortexing, homogenization, or sonication) the viscous precipitate with a sufficient amount, e.g., at least 30 v/v %, of a water-miscible solvent for a time sufficient to obtain a particle suspension; removing particles from the suspension (e.g., removing the solvent); and adding one or more biologically active substances to obtain a stable, sulfated agent hydratable composition including one or more biologically active substances. These methods can further include further drying the stable, sulfated agent hydratable composition to remove any remaining solvent.

In some embodiments, the methods include the steps of mixing a sulfated agent with an acid solution to form a precipitate; adding water-miscible common solvents to the precipitate; stirring to form a suspension in brittle particle form; drying in vacuum to evaporate solvents; and adding one or more the biologically active substances. In some embodiments, the water-miscible common solvent is ethanol, methanol, dimethylsulfoxide (DMSO), or acetone.

In various embodiments, the water-soluble solvent or water-miscible solvent can include any one or more of an alcohol (e.g., methanol, ethanol, isopropanol, n-propanol, reagent alcohol, 2-butoxiethanol, and furfuryl alcohol), acetone, dimethyl sulfide (DMSO), N,N-dimethyl formamide (DMF), acetonitrile, 1,4-dioxane, tetrahydrofuran (THF), acetic acid, acetaldehyde, 1,2-butandiol, 1,3-butandiol, 1,4-butandiol, butyric acid, diethanolamine, diethylenetriamine, dimethoxyethane, ethylamine, ethylene glycol, formic acid, glycerol, methyl diethanolamine, methyl isocyanide, 1,3-propanediol, 1,5-pentanediol, propanoic acid, propylene glycol, pyridine, and triethylene glycol.

In another embodiment, the disclosure includes other methods of making a stable, sulfated agent hydratable composition that includes one or more biologically active substances, by mixing a sulfated agent with an acid solution (e.g., 0.1-1.0 N HCl solution) to form a viscous ("sticky paste") precipitate; and rapidly dehydrating the precipitate by applying microwave energy for a time sufficient to obtain dried particles. Any of these methods can further include grinding or crushing the dried hydratable composition to form a powder.

In another aspect, the disclosure includes methods of delivering one or more biologically active substances to a subject having a disorder in need of treatment. The methods include selecting a subject suffering from a disorder requiring one or more biologically active substances; and administering to the subject a therapeutically effective amount of any of the hydratable compositions described herein that include one or more biologically active substances that are appropriate for the specific disorder. For example, the administering can be done by direct application of the composition, e.g., via endoscopy, needle, brush, or spray, or wherein the composition is in the form of a pill, tablet, capsule, or gel-cap. In these methods, the disorder can be, for example, Type-2 diabetes (e.g., treated with GLP-1), pre-diabetes, obesity, Crohn's disease (e.g., treated with HUMIRA® (adalimumab) or STELARA® (ustekinumab)), irritable bowel syndrome, gastritis, ulcerative colitis, diverticulitis, peptic ulcers, duodenal ulcers, intestinal ulcers, celiac disease, flora imbalances, rheumatoid arthritis (e.g., treated with biologics), hypothyroidism, acromegaly, gastrointestinal infections, leuprolide, intestinal cancer, colorectal cancer, prostate cancer, endometriosis, anti-diuretic hormone deficiency, and the like.

In some embodiments, the hydratable compositions including one or more biologically active substances described herein coat different regions of the GI tract to treat specific diseases. For example, a composition that coats the esophagus can be used to treat Barrett's esophagus. For example, a composition that coats the duodenum can be used to treat Zollinger-Ellison syndrome. For example, a composition that coats the stomach can be used to gastric cancer, peptic ulcer, gastritis, acid reflux (gastroesophageal reflux (GER) and GER disease (GERD)), Ménétrier's disease, and the like. For example, a composition that coats the small intestine can be used to treat Crohn's disease (also large intestine), celiac disease, viral gastroenteritis (also large intestine), Whipple disease, and the like. For example, a composition that coats the large intestine can be used to treat irritable bowel syndrome (also small intestine), ulcerative colitis, colon polyp, and the like. For example, a composition that coats the rectum can be used to treat diverticulosis, hemorrhoid, colorectal cancer (also large intestine), microscopic colitis, proctitis, and the like.

In these methods, the composition can be encapsulated in a degradable capsule, tablet, or pill, e.g., a capsule, tablet, or pill configured to degrade in a specific region of the GI tract. For example, the capsule can include a pH-sensitive material, e.g., one that degrades in alkaline or in acidic conditions. The methods can include the use of compositions that are altered to allow specific cranio-caudal distribution of the composition. For example, the alteration of the composition is a change in the pH sensitiveness of the composition, a change in the electrostatic charge of the composition, and/or a change in the size of the composition. In some embodiments, it coats a specific length of the GI tract.

In some embodiments, the composition coats the entire length of the GI tract. In some embodiments, a composition is administered via site-specific delivery instead of in a pill, tablet, or capsule.

In another aspect, the disclosure includes dehydrated acid-pretreated compositions that include particles including aluminum crosslinked sulfated agents that can form a paste following contact with water in the absence of acid and dry aluminum crosslinked sulfated compositions for use as an aqueous film forming barrier with aluminum content less than 15.5% that forms a viscous paste in the presence of water. These compositions, when in the presence of gastrointestinal fluid, can in certain embodiments, release less than 2% wt/wt aluminum.

In some embodiments, the hydratable compositions provided herein form a paste upon hydration (e.g., re-hydration), such as hydration or rehydration in an aqueous fluid, regardless of the pH of that fluid, that has a viscosity that is, e.g., greater than 35 Pa·s (e.g., greater than 40, 45, 50, 55, or 60 Pa·s). Some embodiments further include placing the hydratable composition into a coating material (e.g., gelatin or hydroxypropyl methylcellulose (HPMC), or any combination of the coating materials described herein or known in the art) to form a coating around the hydratable composition in the particular composition. Some embodiments further include adding the hydratable compositions to a food substance or food additive.

The disclosure also provides methods of treating an oral, gastric, stomach, or intestinal ulcer or wound in a subject (e.g., a subject having mucositis, cancer sore(s), ulcerative colitis, or Crohn's disease) that include, consist of, or consist essentially of selecting a subject having an ulcer or wound and administering to the selected subject a therapeutically effective amount of any of the hydratable compositions provided herein.

Also provided are methods of treating a microbial infection or colonization in a subject in need of such treatment (e.g., a subject having a disorder in need of such treatment) that include, consist of, or consist essentially of selecting a subject in need of such treatment (e.g., a subject having a disorder requiring treatment of a microbial colonization or infection) and administering to the subject a therapeutically effective amount of any of the hydratable compositions described herein. For these uses, the compositions provide a protective and therapeutic effect.

In some embodiments, the hydratable compositions contain, are crosslinked to, are attached to (e.g., physically attached), or combined with an antimicrobial agent (e.g., any of the exemplary antimicrobial agents described herein or known in the art). For example, the antimicrobial agent can be selected from the group of iodine, silver ions, and chlorine, or selected from the group of iodine, silver ions, bismuth (e.g., bismuth salicylate), and chlorine.

In some embodiments, the hydratable compositions described herein are used in combination with or as a supplement to an additional agent, e.g., a therapeutic agent, to treat disorders such as diabetes, obesity, pre-diabetes, and mucositis. For example, the additional agent can be a therapeutic agent that is known to be useful to treat the disorder. The additional agent also can be an agent that imparts a beneficial attribute to the therapeutic composition (e.g., an agent that affects the viscosity of the composition).

The combination therapies contemplated herein include, for example, administration of one or more hydratable compositions as described herein and one or more additional biologically active substances in a single pharmaceutical formulation, as well as administration of one or more compositions as described herein and one or more additional agent(s) in separate pharmaceutical formulations. For example, the additional agents can be administered simultaneously or sequentially over a period of time.

For example, in various embodiments, the hydratable compositions described herein are administered with (e.g., simultaneously or sequentially or as part of the composition) one or more of the following diabetes therapeutic agents: insulin, a metformin, sulfonylurea, alpha-glucosidase inhibitor, thiazolidinediones, amylin analog, bile acid sequestrant, DPP-4 inhibitors, dopamine agonist, incretin mimetics, non-sulfonylurea secretagogues, and meglinitides (Repaglinide/Prandin, Nateglinide/Starlix®). In other embodiments, the hydratable compositions are administered with one or more of the following obesity therapeutic agents: orlistat, lorcaserin, sibutramine, rimonabant, metformin, exenatide, pramlintide (Symlin®), and topiramate/phentermine (Qsymia®). In some embodiments, the hydratable compositions are administered with one or more biologically active substances that would normally be toxic when administered systemically, such as kinase inhibitors.

The agents and compositions set forth herein are for illustrative purposes and not intended to be limiting. The combinations can also include more than one additional agent, e.g., two or three additional agents if the combination is such that the resulting composition can perform its intended function.

The new hydratable compositions can be designed to form a temporary protective layer and carrier to deliver one or more biologically active substances to any portion of the gastro-intestinal (GI) tract, regardless of the pH of the fluid in that portion of the GI tract. Thus, the new compositions can be used to temporarily deliver one or more biological substances to the lining of portions of the GI tract (e.g., the stomach, duodenum, and the small intestines) and release the substance(s) to have effect in the GI tract or to be absorbed through the intestinal lining into the bloodstream. As a result, various medical conditions, e.g., obesity, metabolic disorders (e.g., type II diabetes (T2DM), pre-diabetes, hypothyroidism, and acromegaly), gut disorders (e.g., Crohn's disease, irritable bowel syndrome, gastritis, ulcerative colitis, diverticulitis, peptic ulcers, duodenal ulcers, intestinal ulcers, celiac disease, and flora imbalances), rheumatoid arthritis, gastrointestinal infections, leuprolide, cancers (e.g., intestinal cancer, colorectal cancer, and prostate cancer), endometriosis, anti-diuretic hormone deficiency, and the like, can be treated.

The term "biologically active substances," as used herein, refers to gene editing agents (e.g., CRIPSR systems), modified or naturally occurring bacteria (to alter the microbiome), viruses, antibiotics, cells, such as stem cells and immune cells (e.g., T cells and CAR T cells), biomolecules, small molecular drugs including immune modulating drugs (e.g., dexamethasone, hydrocortisone, and triamcinolone), antibiotics (e.g., cipfloxacin), anti-cancer drugs (e.g., doxorubicin and paclitaxel), and the like. In some embodiments, these biologically active substances are capable of being released by the compositions described herein at a site of action. In some embodiments, these biologically active substances are biologically active at the site of action. In some embodiments, these biologically active substances are biologically active at distal sites.

The hydratable compositions described herein may contain one or more biologically active substances that are therapeutic, prophylactic, and/or diagnostic agents, e.g., that are released from the compositions. The agents can may be a small molecule agent (e.g., molecular weight less than 2000, 1500, 1000, 750, or 500 amu), a macromolecule, or a biomolecule, or combinations thereof. The agent may also be a vaccine.

In some embodiments, the hydratable compositions containing one or more biologically active substances are biologically active at the site of action. For example, a composition described herein can affect the GI tract mucosa for local treatment, such as a biologically active substance for treatment of Crohn's disease, such as one or more of aminosalicylates, corticosteroids, immunomodulators, antibiotics, and the like. In some embodiments, Crohn's disease can be treated with biologically active substances in the form of biologics such as adalimumab (HUMIRA®), adalimumab-adbm (CYLTEZO®), adalimumab-atto (AMJEVITA®), certolizumab (CIMZIA®), infliximab (REMICADE®), infliximab-abda (RENFLEXIS®), infliximab-dyyb (INFLECTRA®), natalizumab (TYSABRI®), ustekinumab (STELARA®), and vedolizumab (EN-TYVIO®).

In another embodiment, the new compositions can be used to treat rheumatoid arthritis with biologically active substances in the form of biologics such as abatacept (OR-ENCIA®), adalimumab (HUMIRA®), adalimumab-adbm (CYLTEZO®), adalimumab-atto (AMJEVITA®), anakinra (KINERET), certolizumab (CIMZIA®), etanercept (EN-BREL®), etanercept-szzs (ERELZI®), golimumab (SIM-PONI®, SIMPONI ARIA®), infliximab (REMICADE®), infliximab-abda (RENFLEXIS), infliximab-dyyb (INFLEC-TRA®), rituximab (RITUXAN®), and tocilizumab (ACTEMRA®).

In another embodiment, a composition described herein having local biological activity can contain one or more beneficial bacterial strains to reduce at least one symptom of a bacterial imbalance.

In some embodiments, a composition described herein comprising one or more biologically active substances release the one or more biologically active substances into the blood stream for treatment. In some embodiments, these biologically active substances are biologically active at distal sites and/or systemically.

Examples of classes of small molecule agents include, but are not limited to, anti-inflammatories, analgesics, antimicrobial agents, steroids, stem cell activating molecules, regenerative therapeutics, and combinations thereof.

Examples of cytokines and growth factors include, without limitation, TNF, TGF-b, acidic fibroblast growth factor, basic fibroblast growth factor, chemokines such as SDF-1, epidermal growth factor, IGF-I and II, vascular endothelial-derived growth factor, bone morphogenetic proteins, platelet-derived growth factor, heparin-binding growth factor, hematopoietic growth factor, and peptide growth factor.

Examples of extracellular matrix components include, but are not limited to, collagen, fibronectin, laminin, elastin and combinations thereof proteoglycans and glycosaminoglycans can also be covalently or non-covalently associate with the materials described herein.

The term "biomolecules," as used herein, refers to molecules (e.g., proteins, amino acids, peptides, polynucleotides, nucleotides, polysaccharides, carbohydrates, lipids, nucleoproteins, glycoproteins, lipoproteins, and steroids) whether naturally-occurring or artificially created (e.g., by synthetic or recombinant methods) that are commonly found in cells and tissues. Specific classes of biomolecules include, but are not limited to, enzymes, receptors, neurotransmitters, hormones, neutraceuticals, small molecules, cytokines, cell adhesion sequences (e.g., RGD sequence and integrins), extracellular matrix components) cell response modifiers such as growth factors and chemotactic factors, antibodies, vaccines, haptens, toxins, interferons, ribozymes, antisense agents, plasmids, aptamers, DNA and RNA (e.g., cDNA, shRNA, siRNA, mRNA, or modRNA).

In some embodiments, the average number of aluminum ions per molecule in the composition is less than 40, 30, 20, or 10. In some embodiments, the composition is capable of forming a paste following contact with an aqueous liquid with a pH greater than 6, 7, 8, 9, or 10.

The terms "polynucleotide," "nucleic acid," or "oligonucleotide" refer to a polymer of nucleotides. The terms "polynucleotide," "nucleic acid," and "oligonucleotide," may be used interchangeably. Typically, a polynucleotide comprises at least three nucleotides. DNAs and RNAs are polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5 bromouridine, C5 fluorouridine, C5 iodouridine, C5 methylcytidine, 7 deazaadenosine, 7 deazaguanosine, 8 oxoadenosine, 8 oxoguanosine, O(6) methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N phosphoramidite linkages).

As used herein, a "polypeptide," "peptide," or "protein" comprises a string of at least three amino acids linked together by peptide bonds. The terms "polypeptide," "peptide," and "protein" may be used interchangeably. Peptide may refer to an individual peptide or a collection of peptides. Inventive peptides preferably contain only natural amino acids, although non-natural amino acids (i.e., compounds that do not occur in nature but that can be incorporated into a polypeptide chain; see, for example, as described on the world-wide-web at cco.caltech.edu/~dadgrp/Unnatstruct. gif, which displays structures of non-natural amino acids that have been successfully incorporated into functional ion channels) and/or amino acid analogs as are known in the art may alternatively be employed.

In addition, one or more of the amino acids may be modified, for example, by the addition of a chemical entity such as a carbohydrate group, a phosphate group, a farnesyl group, an isofarnesyl group, a fatty acid group, a linker for conjugation, functionalization, or other modification, etc. In a preferred embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

The terms "polysaccharide," "carbohydrate," or "oligosaccharide" refer to a polymer of sugars. The terms "polysaccharide," "carbohydrate," and "oligosaccharide," may be used interchangeably. Typically, a polysaccharide comprises at least three sugars. The polymer may include natural sugars (e.g., glucose, fructose, galactose, mannose, arabinose, ribose, and xylose) and/or modified sugars (e.g., 2'-fluororibose, 2'-deoxyribose, and hexose).

The term "humectant" refers to a substance that absorbs or helps another substance retain moisture, such as a hygroscopic substance. It has the property to promote water retention in a substance. When incorporated into a compound structure, hydrophilic humectant molecules increase efficacy of hydration. A crosslinking humectant is an effective cross-linker or spacer that connects different components of a compound or composition.

The hydratable compositions described herein may also be used as a vehicle to deliver cells and/or transfection agents.

The hydratable compositions described herein may be applied via multiple modalities including direct application, endoscopy, needle, brush, spray, plug, pill, tablet, and gelcap.

In some embodiments, the particulate, e.g., microparticulate, hydratable compositions described herein are not absorbed by the body of the patient to whom they are administered.

In some embodiments, the hydratable compositions can be formulated as a powder, emollient, cream, ointment, or suspension.

In some embodiments, the paste, which is obtained by contacting the hydratable composition with a liquid containing water, can be used to coat biological surfaces, e.g., the rectum, vagina, nasal, and skin.

In some embodiments, the hydratable composition can be delivered as a drink, a solution, or an elixir. In some embodiments, the composition can be administered in a drinking straw form.

In some embodiments, the hydratable composition can be used to deliver sensing molecules (e.g., sensors) as well as contrast agents (e.g., microbubbles or radiocontrast agent).

In another aspect, the present disclosure also provides methods to promote mucosal healing by identifying a subject in need of such treatment, and applying the hydratable composition or the paste as described herein containing an appropriate biologically active substance, which is obtained by contacting the hydratable composition with a liquid containing water, to the sites in need of such treatment.

In one aspect, the present disclosure also provides methods to treat dermatitis. The method includes the step of identifying a subject in need of such treatment, and applying the hydratable composition or the paste as described herein with a suitable biologically active substance, which is obtained by contacting the hydratable composition with a liquid containing water, to the sites of dermatitis. Other uses are also contemplated, e.g., treating hemorrhoids, treating venous ulcers, treating infection, etc.

The term "subject" is used throughout the specification to describe an "animal" or a "human." The term "animal" includes, but is not limited to, birds, reptiles, amphibians, and mammals, e.g., humans, other primates, pigs, rodents such as mice and rats, rabbits, guinea pigs, hamsters, cows, horses, cats, dogs, sheep and goats. Preferred subjects are humans, farm animals, and domestic pets such as cats and dogs.

As used herein, the phrase "therapeutically effective amount" refers to the amounts of the hydratable composi- tions and the one or more biologically active substances as described herein that elicit the desired biological or medici- nal response including one or more of the following: (1) inhibiting a disease, condition, or disorder, or one or more symptoms of the disease, disorder, or condition, in an individual who is experiencing or displaying the pathology or symptomatology of the disease, condition or disorder such as in the case of type 2 diabetes mellitus, inhibiting increased plasma glucose levels; (2) promoting weight loss; (3) preventing or reducing the risk of developing type II diabetes in a subject having pre-diabetes; or (4) ameliorating the disease or symptoms of the disease; for example, ame- liorating a disease, condition, or disorder, or symptom thereof, in an individual who is experiencing or displaying the pathology or symptomatology of the disease, condition, or disorder (i.e., reversing the pathology or symptomatol- ogy) such as ameliorating plasma glucose levels.

For example, the following symptoms of diabetes can all be improved by treating a subject with the compositions described herein: ameliorating plasma glucose levels, HbA1c levels, plasma insulin levels, or active or total Glucogon-like peptide (GLP) levels, or eliminating increased thirst, frequent urination, increased hunger, hyper- tension, hyperlipidemia, weight loss or gain, obesity-related joint problems, high blood pressure, total cholesterol, elevated LDL and triglycerides, metabolic syndrome, fatigue, blurred vision, slow healing sores, frequent infec- tions, neuropathic pain, kidney failure, or darkened skin AND/OR elicit one or more of the following: increased levels of postprandial active GLP-1 in plasma, decreased levels of postprandial glucose in plasma, increased levels of C-peptide in plasma, decreased levels of appetite sensation measured by Visual Analogue Scale (VAS), decreased levels of 24-hour plasma glucose assessed by Continuous Glucose Monitoring System (CGMS) or weight loss.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, or other problem or complica- tion, commensurate with a reasonable benefit/risk ratio.

The term "kit" refers to pharmaceutical kits useful, for example, in the treatment or prevention of diabetes or obesity, which include one or more containers containing a compound or pharmaceutical composition comprising a therapeutically effective amount of one or more of the compounds described herein. Such kits can further include, if desired, one or more of various conventional pharmaceu- tical kit components, such as, for example, containers with one or more pharmaceutically acceptable carriers, additional containers, etc., as will be readily apparent to those skilled in the art. Instructions, either as inserts or as labels, indi- cating quantities of the components to be administered, guidelines for administration, and/or guidelines for mixing the components, can also be included in the kit.

The term "polymer" is employed herein to refer to chemi- cal compounds or a mixture of compounds comprised of repeating structural units.

The phrase "mucoadhesion" is employed herein to refer to a form of adhesion between two materials, at least one of which is a mucosal surface. Mucoadhesion typically occurs within the body of a subject.

The phrase "oral glucose tolerance test" refers to a diag- nostic assay in which blood samples are obtained from a subject or patient following glucose administration to deter- mine time to clearance of the glucose from the subject's or patient's system. The test is commonly utilized in determin- ing the presence of diabetes or insulin resistance in a subject or patient.

The term "hydratable composition," "water hydratable composition," or "water-based liquid hydratable composi- tion" refers to a composition that can form a paste following contact with a liquid containing water, e.g., pure water, or an aqueous solution with one or more solutes. The liquid can have any pH, for example, it can be acidic, or non-acidic, e.g., it can have a pH value from 1 to 14.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 1 is a schematic diagram depicting the concept of oral delivery of the new sulfated agent-based hydratable compositions (AF-LuCI particles), e.g., in a pill or a capsule, that are dispersed to form a barrier coating in the gastroin- testinal tract, e.g., in the stomach and/or small intestines, and to deliver one or more biologically active substances.

FIGS. 4A and 4B are schematic representation of the chemical changes of poly aluminum complex (PAC) in sucralfate and AC-LuCI during fabrication.

FIGS. 4C and 4D are representations of the chemical structures and chemical formulas of sucralfate, acidified sucralfate paste, and AF-LuCI. The ionized aluminum atoms (coordination number=6) are polymerized through coordi- nation bonds with hydroxyl groups and surrounded by water molecules also through coordination bonds.

FIG. 19D is a schematic diagram showing local barrier effect of AF-LuCI in OGTT with orally administered glucose.

FIG. 19E is a graph showing OGTT curves of rats gavaged with AF-LuCI pastes. Rats gavaged with 0.9 w/v % normal saline was used as a control.

FIG. 19F is a graph showing iAUC of the OGTT curves in FIG. 19E. (*<0.05 and **<0.001 in one-way Analysis of Variance (ANOVA)).

FIG. 19G is a schematic diagram showing representative schematic of no systemic effect of AF-LuCI in intraperitoneal injection (IpGTT) with systemically administered glucose.

FIG. 19H is a graph showing IpGTT curves of rats gavaged with AF-LuCI pastes. Rats gavaged with 0.9 w/v % normal saline was used as a control.

FIG. 19I is a graph showing iAUC of the OGTT curves in (h). (*<0.05 and **<0.001 in one-way ANOVA).

FIG. 20A is a schematic diagram that demonstrates oral administration and mucoadhesive delivery of a biologically active substance (e.g., therapeutic agent) using LuCI.

DETAILED DESCRIPTION

Figure 2:
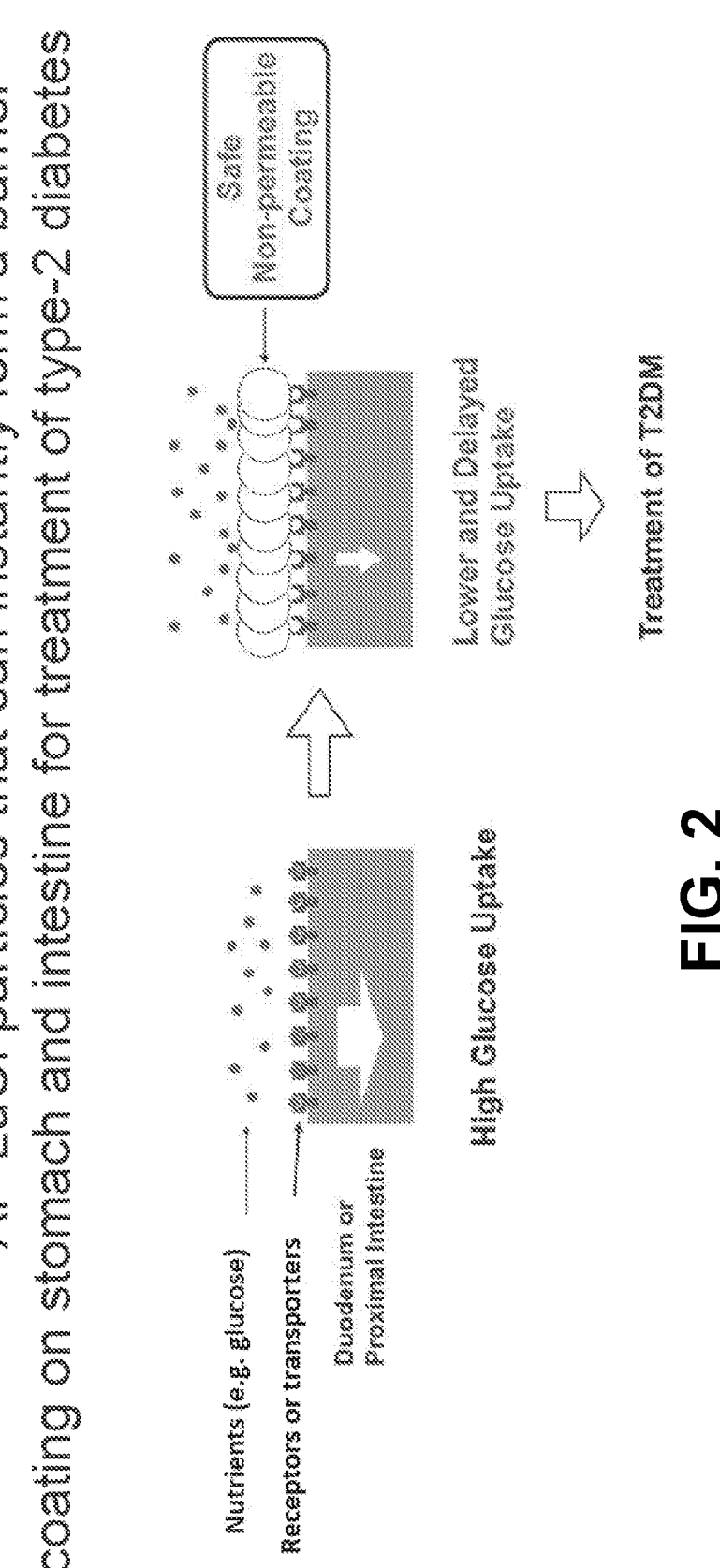
FIG. 2 is a schematic diagram showing the dispersal of the dry particles in the presence of liquids within the stomach and/or small intestines and instantly forming a safe, non- permeable barrier coating on the stomach and/or intestinal lining that can reduce and/or delay the uptake of glucose and other nutrients and be used to deliver one or more biologi- cally active substances.

The present disclosure describes methods of delivering a biologically active substance by mixing the substance with one or more water-based, liquid hydratable compositions and coating of the luminal surface of portions of the GI tract (e.g., proximal GI tract) including the duodenum, jejunum, ilium, proximal intestine, the entire small intestine, the large intestine, and the colon, with an orally administered mucoadhesive hydratable compositions, e.g., microparticulate, formulation, or a liquid formulation (see, e.g., FIG. 1). These hydratable compositions are made of particles that include aluminum crosslinked sulfated agents, such as sucralfate, which is a sucrose octasulfate-aluminum complex that is an FDA-approved, orally administrated drug indicated for the treatment of active gastric and duodenal ulcers. The viscosity of sucralfate is a key determinant of its barrier and delivery/carrier performance. When exposed to an aqueous liquid (i.e., stomach acid or intestinal fluid), the hydratable compositions form a sticky paste that physically coats the luminal surface of the mouth, throat, stomach, duodenum, and/or small intestines to thicken the protective mucosal layer via a strong mucoadhesive interaction with gastric and duodenal mucus (S. Higo et al; Pharm. Res. 21, 413-419 (2004); Tasman-Jones and Morrison, Am. J. Med., 86, 5-9 (1989); Slomiany et al., Am. J. of Med., 91, 30-36, 1991).

However, when sucralfate is used by itself and reacts with stomach acid to form a sticky paste, it releases a significant amount of aluminum. Hence, one hurdle for the use of sucralfate for the treatment of T2DM is potential excessive aluminum absorption, particularly because a prolonged, repeated dosing required for T2DM therapy, leading to long-term aluminum exposure. Further, 25-40% of diabetic patients suffer from chronic renal impairment and hence, may be increasingly susceptible to potential side effects due to the aluminum release from sucralfate. Unlike patients with normal renal function who can adequately excrete the aluminum and hence only retain a limited quantity, patients with CRI can have an impaired excretion of aluminum that could limit the long-term use of sucralfate for T2DM patients (J. P. New et al., Diabetic Medicine, 24, 364-369; Eberhard, Ritz et al., New Engl. J. Med., 341, 1127-1133 (1999)). Thus, it is essential to ensure that transient nutrient barrier coatings that are to be administered over prolonged periods of time release little to no toxic components such as aluminum. Reducing the exposure of aluminum to a T2DM patient would increase the safety profile of this therapy for clinical translation of sucralfate as an intestinal barrier in patients.

Sucralfate has also been used to prepare sucralfate compositions, e.g., as described in PCT WO2014/151565, which is incorporated herein by reference. While prior sucralfate compositions exhibit an effective barrier property to glucose absorption when rehydrated in acidic liquids, a significant quantity of sucralfate is liberated during gelation after rehydration, and thus the full amount of the composition not available for subsequent coating. Furthermore, during the initial rehydration process, the compositions release aluminum. This released aluminum can potentially accumulate in tissue over time with repeated exposures, which can be highly undesirable and is specifically contraindicated in patients with renal insufficiency.

Ideal mucoadhesive formulation for gut coating should 1) be capable to form a layer on mucus layer on the lumen upon contact with aqueous mucus on different segments of GI tract with different pH (i.e. stomach pH ~1, duodenum pH 3-5, intestine pH>6), 2) have good barrier properties, 3) be stable in shear stress under aqueous environment (i.e. shear resistance, low swelling), 4) be able to be encapsulated into enteric coated capsules, thus should be in dried formulation, 5) be safe to use, 6) be effectively combined with a biologically active substance, 7) protect a biologically active substance from the stomach environment, 8) successfully deliver a biologically active substance to various parts of the GI tract (including, but not limited to, the ilium, jejunum, and duodenum).

Commonly used gelatinous mucoadhesive polymers are not suitable for this purpose given that they absorb water and swell rapidly that can compromise the mucoadhesion, shear resistance and the barrier properties. In the screening result in our earlier study, sucralfate has been identified as having the best barrier properties. In stomach acid, sucralfate forms a sticky paste that can bind to stomach ulcers to form a protective layer. However, given that sucralfate requires acid (pH lower than ~2) to form the sticky paste and the binding is specific to ulcers, it is undesirable to form a layer on duodenum or intestine with higher pH environment.

Hence, as described herein, new mucoadhesive particle compositions combined with at least one biologically active substance were developed based on sucralfate and other sulfated agents that can form a mucoadhesive sticky paste that protects and delivers the biologically active substance and that simultaneously minimize the potential side effects by reducing the amount of aluminum content released into the body.

A surprising benefit realized for the new hydratable compositions is that they can be rehydrated in liquids at any pH and mixed with a biologically active substance. Thus, compositions described herein can be used to form viscous coatings and deliver biologically active substance(s) not only in the stomach, but also in other parts of the GI tract, e.g., in the stomach (pH 1), duodenum (pH 3-5), intestine (pH 6-7), and colon (pH 5.5-7). The new methods described herein can significantly reduce the water content below the levels found in prior sucralfate compositions, which enables the new hydratable compositions to be rehydrated with aqueous liquids, such as water, regardless of pH, and without altering PAC chemistry or without using any additives (gel protector agents, humectants, etc.). As a result, one can deliver more of the hydratable composition per unit volume in a given pill, tablet, or capsule than is possible for prior sucralfate compositions with a higher water content.

In some embodiments, the new hydratable compositions can form a paste following contact with a liquid having any pH, for example, pH 1, pH 2, pH 3, pH 4, pH 5, pH 6, pH 7, pH 8, pH 9, pH 10, pH 11, pH 12, pH 13, or pH 14. In some embodiments, the liquid can have a pH from 1 to 14, from 2 to 13, from 3 to 12, from 4 to 11, from 5 to 10, from 6 to 9, from 6 to 10, from 6 to 11, from 6 to 12, from 6 to 13, or from 6 to 14; or have a pH greater than 6, 7, 8, 9, 10, 11, 12, or 13. In some embodiments, new compositions can be mixed with a biologically active substance at a biologically active substance to LuCI ratio of about 1:1, about 1:10, about 2:10, about 3:10, about 4:10, about 5:10, about 6:10, about 7:10, about 8:10, about 9:10, about 10:1, about 10:2, about 10:3, about 10:4, about 10:5, about 10:6, about 10:7, about 10:8, or about 10:9.

General Methodology

The novel aluminum-crosslinked sulfated agent-based, e.g., sucralfate-based, hydratable compositions are inert, non-absorbable compositions in the form of dried particulates or suspensions that can temporarily coat the luminal lining of the digestive track and reduce absorption of ingested nutrients through the intestinal lining and thus keep those blocked nutrients from entering into the blood stream or having other systemic effects.

The examples below demonstrate that the administration of the new particulate, e.g., microparticulate, compositions described herein provide an effective barrier to glucose absorption anywhere in the GI tract, e.g., to thereby lower postprandial blood glucose concentration. Thus, the new compositions and methods can be useful to treat disorders in which one desires to reduce the absorption of one or more nutrients into the body.

For example, management of type II diabetes requires an altered diet, often in addition to a drug or insulin-based therapy. Similarly, controlling various forms of obesity require regulation of food intake together, often with drug therapy or surgical approaches including bariatric surgery. As shown schematically in FIG. 2, the sulfated agent-based hydratable compositions described herein reduce nutrient passage from the intestinal lumen to the blood stream through the intestinal lining. For example, inhibition or delayed inhibition of nutrient absorption can mean inhibiting glucose absorption. Thus, the new hydratable compositions can be used to treat type II diabetes. For example, new compositions can include a LuCI formulation mixed with a biologically active substance already approved to treat obesity or diabetes. Non-limiting examples of such biologically active substances are insulin, a metformin, sulfonylurea, alpha-glucosidase inhibitor, thiazolidinediones, amylin analog, bile acid sequestrant, DPP-4 inhibitors, dopamine agonist, incretin mimetics, non-sulfonylurea secretagogues, meglinitides (Repaglinide/Prandin, Nateglinide/Starlix®), orlistat, lorcaserin, sibutramine, rimonabant, metformin, exenatide, pramlintide (Symlin®), and topiramate/phentermine (Qsymia®).

The hydratable compositions described herein are prepared in a manner to reduce the presence of metallic ions (i.e., aluminum ion) in the compositions to thereby reduce the release of aluminum from the sucralfate based hydratable composition in the presence of acid (i.e., stomach acid), in turn, reducing the potential side effects from excess aluminum in the bloodstream. Moreover, hydratable compositions described herein are mixed with a biologically active substance and prepared in a manner to protect the biologically active substance from the acidic environment of the stomach, and deliver the biologically active substance to the desired area of the GI tract.

Hydratable Compositions and Methods of Making the Compositions

The aluminum-crosslinked sulfated agent-based, e.g., sucralfate-based, hydratable compositions (also referred to herein as "AF-LuCI" particles) include or consist of a polymer of ionized aluminum ions. Sucralfate is composed of aluminum hydroxides linked to sucrose octasulfate. Other sulfated agents include sulfated dextran, sulfated dextrin, sulfated amylopectin, sulfated amylose, sulfated cellulose, carrageenan, chondroitin sulfate, glucose sulfate, sucrose sulfate, heparin, heparin sulfate, and raffinose sulfate. Once the LuCI particles are formed, one can add the one or more biologically active substances. If the biologically active substance is stable in acid or alcohol, the substance can be added just before the final acid or alcohol treatment, as described below.

Figures 4A, 4B:
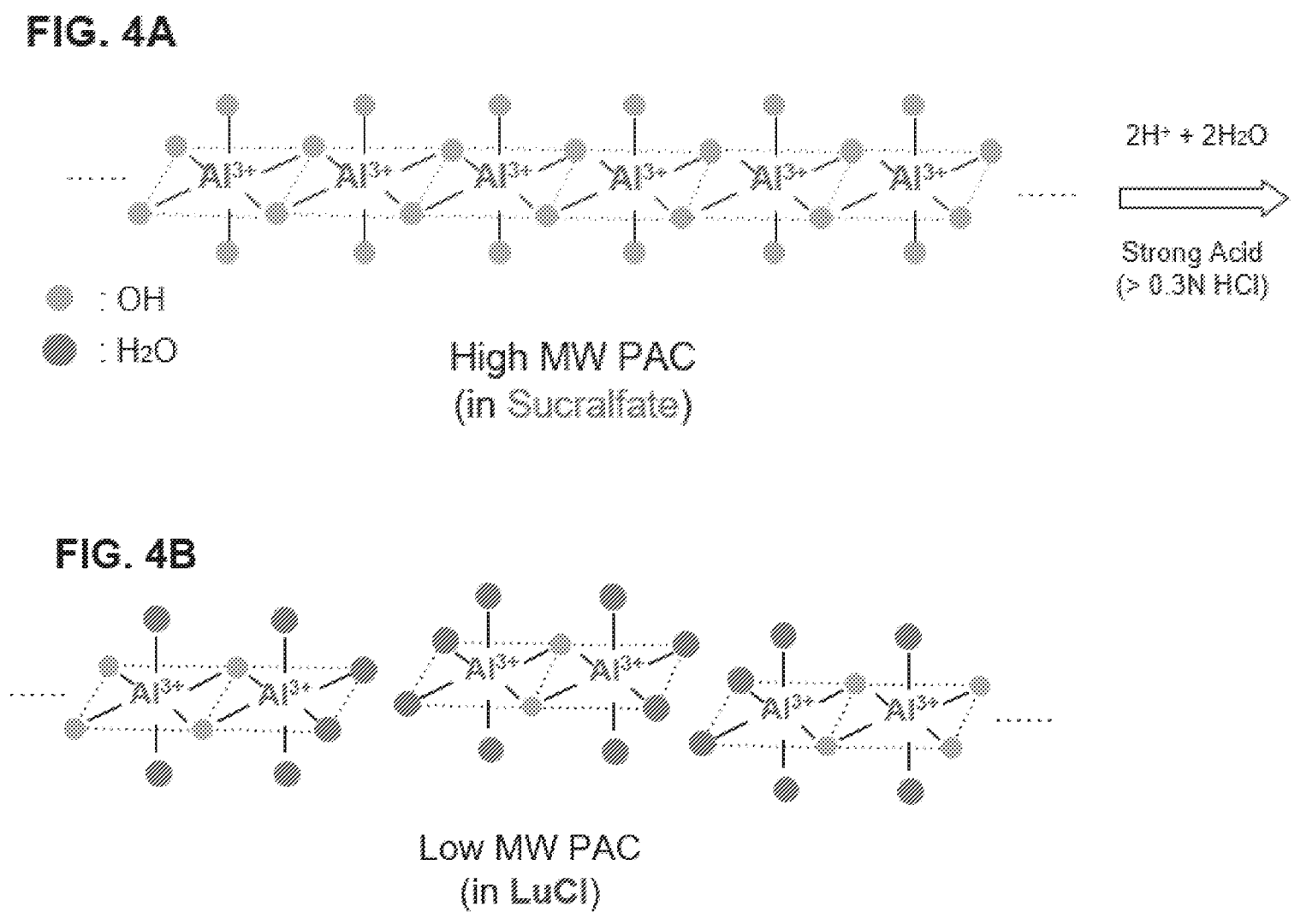

Sucralfate comprises two oppositely charged polyions forming a water-insoluble salt: anionic sucrose octasulfate, and cationic poly aluminum complex (PAC) (FIG. 4A). PAC is a cationic inorganic polymer with aluminum ions as backbone linked together via coordination bonds with hydroxo linkages (—OH—). When it is exposed to acid, a part of the hydroxo linkages are reversibly protonated to form water (—OH$_2$) and in stronger acid additional protonation (H$^+$) and further hydration (H$_2$O) irreversibly break the bond to shorten the polymer chain that is surrounded by more water molecules compared to the PAC in the native sucralfate (FIG. 4B).

When a sulfated agent such as sucralfate reacts with an acid, a part of the aluminum component is released and another part cross-links together to form a "poly aluminum complex." The ionized aluminum atoms (coordination number=6) are believed to be polymerized through coordination bonds with hydroxyl groups and surrounded by water molecules also through coordination bonds. As shown in FIG. 4C, when the aluminum hydroxide groups react with acid they form partially hydrated cationic poly-aluminum complexes. The hydrated poly-aluminum complex has an overall positive charge and strongly binds to negatively charged sucrose octasulfate through electrostatic interactions to form a water-insoluble sticky paste. As the hydroxo linkages are responsible for the pH-dependent change of rheological properties by reversible protonation, the shorter PAC polymers with less hydroxo linkages and more bound water (—OH$_2$) would minimize the pH-dependency and can be easily dehydrated/re-hydrated without the need of acid. In addition, by controlling the electrostatic charge, the shorter and more hydrated PAC polymers would undergo complex coacervation with anionic sucrose octasulfate where the two polyions are electrostatically entangled to form a water-immiscible liquid with controlled viscosity.

Figure 3:
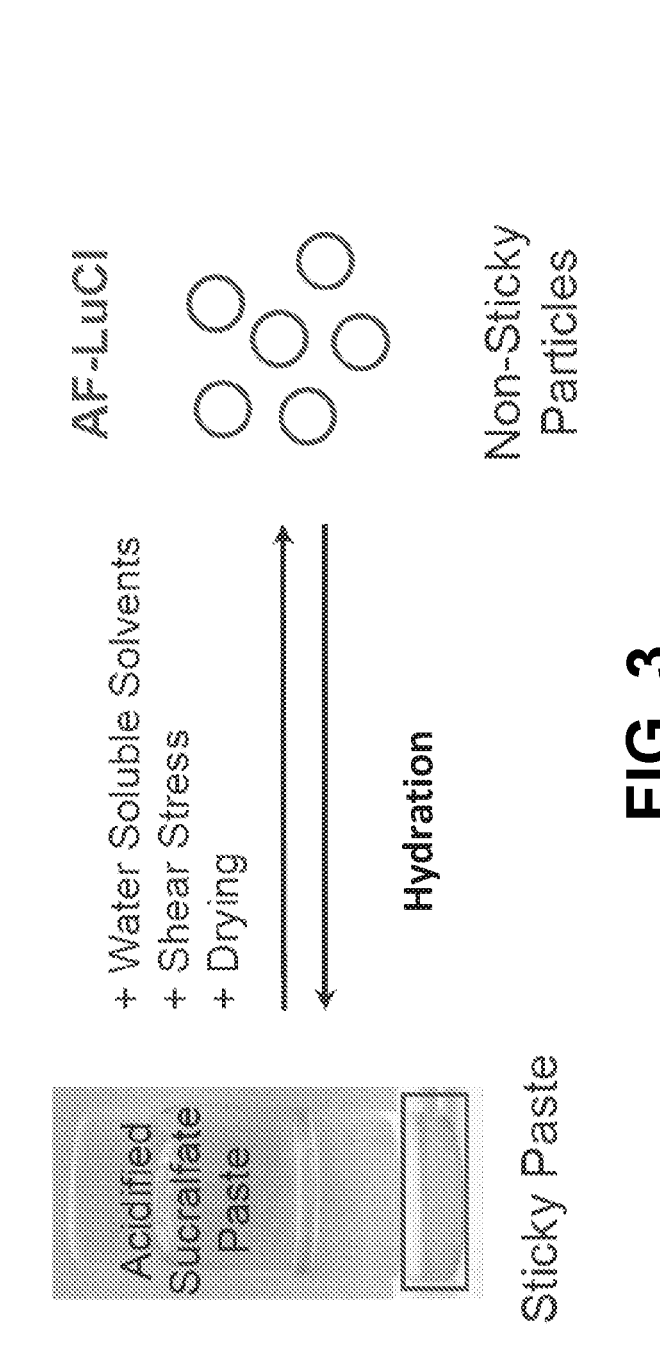
FIG. 3 is a schematic diagram showing how a sticky acidified sucralfate paste can be easily reformulated into non-sticky particles of AF-LuCI using water-soluble sol- vents.

Based on thermogravimetric analysis (TGA) and Fourier-transform infrared spectroscopy (FT-IR) as described in the examples below, and without being bound by the following theory, in the example using sucralfate, as shown in FIGS. 3 and 4D, it appears that when the acidified sucralfate sticky paste is mixed with a water-soluble (water-miscible) solvent such as alcohol (and then the solvent is removed), a rapid dehydration reaction occurs and a number "n" of the x aluminum hydroxide groups (Al(OH)$_3$) of sucralfate leave the structure (leaving "x–n"), and a number "m" of aluminum hydroxide groups appear to form a poly-aluminum complex that is crosslinked via 1 or 2 or 3 hydroxyl groups (—(OH)$_i$)(where i=1 or 2 or 3) between the aluminum ions to form —[Al—(OH)$_i$]$_m$. Therefore, the predicted chemical structures of sucralfate, acidified sucralfate paste, and AF-LuCI are:

| | |
|---|---|
| C$_{12}$H$_{30}$Al$_8$S$_8$•$x$Al(OH)$_3$•$y$H$_2$O | (sucralfate) |
| C$_{12}$H$_{30}$Al$_8$S$_8$•($x$-$n$)Al(OH)$_3$•—[Al—(OH)$_i$]$_m$-•$a$H$_2$O | (Acidified sucralfate paste) |
| C$_{12}$H$_{30}$Al$_8$S$_8$O$_{51}$•$x$[Al(OH)$_i$]•$z$H$_2$O | (AF-LuCI) | where x is less than or equal to 8 (8 for sucralfate, and is equal to the number of aluminum atoms), 0<n<x, m is greater than or equal to 2 (and can be less than n), i=1 or 2 or 3, and z<x·i.

The variable y in yH$_2$O is the moisture that is absorbed and potentially complexed with Al. Therefore, y<(6–3) x=3x, where 3× denotes the maximum number of water molecule that can bind to Al(OH)$_3$. The variable z is also the absorbed moisture in AF-LuCI. Therefore, z<3(x–n)+(6–i) m, where (3(x–n) is the maximum number of water molecules that can bind to Al(OH)$_3$, and (6–i)m is that for the poly aluminum complex. Note that the "y" and "z" "H$_2$O" values can range from 5.0-40.0 w/w % in sucralfate, e.g., can be less than 20 w/w %.

In general, to fabricate the dry AF-LuCI particles using solvent-based dehydration, a sulfated agent, such as sucralfate, is first treated with an acid solution (e.g., 0.1-1.0 N HCl solution) to form a viscous precipitate ("sticky paste") (as shown schematically in FIG. 3). The precipitate is then rapidly dehydrated, e.g., by mixing with a sufficient amount, e.g., at least 30 v/v %, of a water-soluble (water-miscible)

solvent (but not a water-immiscible solvent) and mixed to apply a shear stress for a time sufficient to obtain a particle suspension, e.g., from a few seconds to a few minutes, and then removing the solvent. In some embodiments, these particles can be white.

In some embodiments, the viscous sticky paste is further combined with water-soluble solvents (e.g., alcohol, acetone, DMSO, and DMF) and vortexed resulting in a white particle suspension. The suspension is then dried to remove the solvent and the dried particles are further ground to form a white powder. The biologically active substances can be added to the dried LuCI composition to form a physical mixture, or if stable in acid, the substances can be added to the composition just prior to the acid treatment, and if stable in the water-soluble solvent, can be added to the sticky paste just prior to treatment with the water-soluble solvent such as alcohol.

In some embodiments, the acid solution is hydrochloric acid (HCl), hydroiodic acid (HI), hydrobromic acid (HBr), perchloric acid ($HClO_4$), nitric acid ($HNO_3$) or sulfuric acid ($H_2SO_4$). In some embodiments, the acid solution is 0.1 N HCl, 0.2 N HCl, 0.3 N HCl, 0.4 N HCl, 0.5 N HCl, 0.6 N HCl, 0.7 N HCl, 0.8 N HCl, 0.9 N HCl, or 1.0 N HCl. In some embodiments, the hydrochloric acid (HCl) has a concentration greater than 0.1N, 0.2 N, 0.3 N, 0.4 N, 0.5 N, 0.6 N, 0.7 N, 0.8 N, 0.9 N, or 1.0 N.

Useful water-soluble solvents include alcohols (e.g., methanol, ethanol, isopropanol, n-propanol, reagent alcohol, 2-butoxiethanol, and furfuryl alcohol), acetone, dimethyl sulfide (DMSO), N,N-dimethyl formamide (DMF), acetonitrile, 1,4-dioxane, tetrahydrofuran (THF), acetic acid, acetaldehyde, 1,2-butandiol, 1,3-butandiol, 1,4-butandiol, butyric acid, diethanolamine, diethylenetriamine, dimethoxyethane, ethylamine, ethylene glycol, formic acid, glycerol, methyl diethanolamine, methyl isocyanide, 1,3-propanediol, 1,5-pentanediol, propanoic acid, propylene glycol, pyridine, and triethylene glycol.

In another embodiment, instead of using water-soluble (water-miscible) solvents to quickly dehydrate the acidified sucralfate paste, one can also use other quick dehydration methods, e.g., to quickly heat and dry the composition, e.g., with a microwave oven, to prepare AF-LuCI particles. For example, an amount of a sulfated agent, such as sucralfate, can be added to a container, e.g., a glass vial, and then mixed with an acidic solution, e.g., an amount, e.g., 10 ml, of 0.1-1.0 N HCl solution in water, and immediately vortexed in 3000 rpm for 10 seconds to form a viscous precipitation. For example, a microwave drying process can be performed with a microwave oven (power: 800 W) for 30 seconds.

The particles from which the solvent is removed can be further dried to remove any remaining water-soluble solvent. The dried particles can be ground or crushed to form even smaller particles to form a AF-LuCI powder.

After the biologically active substances are added, the dried particles or powder can then be rehydrated as needed in any aqueous liquid regardless of pH. The resulting viscous sticky paste, or the particles or powder, can be mixed with various agents to stabilize the paste or particles and to control the level of hydration and control overall viscosity. For example, those agents can include humectants or cross-linking humectants. These agents can include, consist of, or consist essentially of, e.g., carrageenan, propylene glycol, 1,2,6-hexanetriol, butylene glycol, dipropylene glycol, hexylene glycol, glycerin, triethylene glycol, erythritol capryl glycol, phytantriol, hexanediol beeswax, hexanetriol beeswax, panthenol, sodium pyrollidone carboxylic acid, hyaluronic acid, inositol, glycogen, sorbitol, polyglyceryl sorbitol, glucose, fructose, xylitol, elastin, collagen, silk, keratin, isoceteth, isolaureth, laneth, laureth, steareth, polyethylene glycol, silicon copolymers, ammonium lactate, glyceryl triacetate, hydrolyzed collagen, hydrolyzed elastin, hydrolyzed keratin, hydrolyzed silk, lactic acid, manitol, panthenol, polydextrose, propylene glycerol, quilaia, urea, or betaine.

Particle stabilizers can be selected, for example, from the non-limiting group of phosphate ions, pectin, carrageenan, chitosan, cellulose derivatives, gellan gum, alginate, gum karaya, dextran, pullulan, polyethylene glycol (PEG), polyvinyl alcohol (PVA) beeswax, sodium borate, stearic acid, carbomer, cetyl alcohol, propylene glycol, polysorbate, lecithin, glyceryl monostearate, acetic esters of fatty acid, lactic esters of fatty acid, citric esters of fatty acid, tartaric esters of fatty acid, acetyltartaric esters of fatty acid, sucroglycerides, polyglycerol esters of fatty acid, propane-2,3-diol esters of fatty acid, sodium stearoyl-2-lactylate, calcium stearoyl-2-lactylate, stearyl tartate, and castor oil derivatives.

Figure 5:
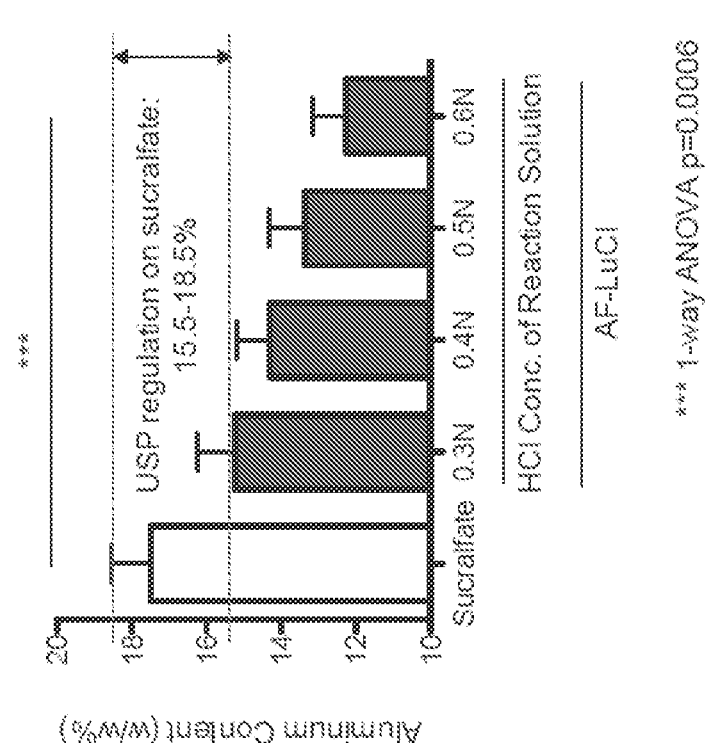
FIG. 5 is a bar graph showing the aluminum content of sucralfate vs. AF-LuCI particles. The AF-LuCI particles contain significantly lower aluminum content (lower than 15 w/w % of the total weight) compared to the native sucralfate (which is 15.5-18.5 w/w % of the total weight).

Because a part of aluminum content is released from sucralfate upon the acid treatment, the AF-LuCI particles have a significantly lower aluminum content (lower than 15.5 w/w % of the total weight, ranging from about 10.0 to about 15.5 w/w %) than the native sucralfate (USP regulation on the aluminum content of sucralfate is 15.5-18.5 w/w % of the total weight) (FIG. 5). As a result, the new hydratable compositions release a significantly lower level of aluminum compared to sucralfate and prior sucralfate compositions when rehydrated. For example, when sucralfate is used and exposed to an acidic fluid, e.g., gastric fluid, it releases about 15.0 w/w % of its original aluminum content. On the other hand, the new AF-LuCI hydratable compositions exposed to the same acidic fluid (or any aqueous liquid, regardless of pH) release less than about 2.0 w/w % of the original aluminum content of commercially available sucralfate.

In some embodiments, polyaluminum complex (PAC) polymers in AF-LuCI are shorter than in sucralfate, for example, the average number of aluminum ions per molecule of AF-LuCI can be less than 50, 40, 30, 20, 19, 18, 17, 16, 15, 14, 13, 12, 11, 10, 9, 8, 7, 6, or 5. In some embodiments, the numbers of aluminum ions per molecule of AF-LuCIs can be less than 40 or 30. In some embodiment, the average number of aluminum ions per molecule of AF-LuCIs can be about 20, 19, 18, 17, 16, 15, 14, 13, 12, 11, 10, 9, 8, 7, 6, or 5.

While sucralfate has been tested, other sulfated agents can also be used in the methods described herein. For example, sulfated agents including, but not limited to, sulfated dextran, sulfated dextrin, sulfated amylopectin, sulfated amylose, sulfated cellulose, carrageenan, chondroitin sulfate, glucose sulfate, sucrose sulfate, and raffinose sulfate, can be used to create the compositions described herein. In addition, all of the hydratable compositions described herein can be prepared by methods described herein using reagents that can be readily obtained from a commercial source. For example, sucralfate can be obtained from a commercial source such as Sigma-Aldrich (St. Louis, Michigan).

The dry particles, e.g., microparticles, described herein can be packaged into a pill, tablet, or capsule form. For example, the particles within any of the compositions described herein can be encapsulated by an enteric coating. For example, the coating can be comprised of one or more of gelatin, hydroxypropyl methylcellulose (HPMC), Eudragit®, and Acryl-EZE®. In some embodiments, the composition is a capsule containing the particles described herein. In addition, any of the hydratable compositions described herein can be mixed into a food substance (e.g., a bar or shake) or with other additives (e.g., a salt). Additional examples of food substances or additives are known in the art.

For example, the compositions containing the biologically active substances can be filled into a gelatin capsule. For an enteric coating, Eudragit® can be dispersed in water in the presence of plasticizer (e.g., triethyl citrate) and anti-tacking agent (e.g., talc), and gently stirred with a conventional stirrer. The suspension can be filtered through a 0.5 mm sieve and will then can be coated on the prepared gelatin capsule using a spray coater. For each segment in the GI tract, Eudragit® E100, Eudragit® E12, 5 or Eudragit® E PO can be used for targeting the stomach (non-enteric coating) Eudragit® L30 D-55 or Eudragit® L100-55 can be used for targeting the duodenum, and Eudragit® L100 or Eudragit® L12, 5 can be used for targeting the jejunum. In addition, Eudragit® S100, Eudragit® S12, 5 or Eudragit® FS30D can be used to target the ileum.

Methods of Using the Hydratable Compositions

The aluminum-crosslinked sulfated agent-based, e.g., sucralfate-based, hydratable compositions are combined with a biologically active substance and used as a therapy for any patients, or can be used as an add-on therapy for patients with disorders that require reduction of ingested nutrients. For example, hydratable compositions can be mixed with biologically active substances such as insulin, a metformin, sulfonylurea, alpha-glucosidase inhibitor, thiazolidinediones, amylin analog, bile acid sequestrant, DPP-4 inhibitors, dopamine agonist, incretin mimetics, non-sulfonylurea secretagogues, meglinitides (Repaglinide/Prandin, Nateglinide/Starlix®), orlistat, lorcaserin, sibutramine, rimonabant, metformin, exenatide, pramlintide (Symlin®), and topiramate/phentermine (Qsymia®).

For example, T2DM patients exhibit increased blood glucose after ingesting glucose via routine food intake due to insulin resistance. Increased blood glucose levels lead to the classical symptoms of polyuria, polydipsia, and polyphagia. However, if left untreated, T2DM can lead to serious complications including ketoacidosis, hyperosmolar coma, cardiovascular disease, chronic renal failure, and retinopathy. Maintaining a healthy weight as a T2DM patient is an important life style factor to avoid increased severity of diabetes, increased complications, or even death. Hence, the use of a sucralfate-crosslinking humectant microparticulate by a T2DM patient would have dual benefits: reduction of glucose absorption, as well as reduction of absorption of other nutrients resulting in weight loss (e.g., fats and carbohydrates), and weight loss.

The decreased, or in some cases delayed, uptake of, for example glucose, could be a treatment for type II diabetes. In effect, it can lessen the dose needed for diabetes treatments including insulin, metformin, or sulfonylureas. The presence of the barrier particles resulting from the novel formulation forming a lining along the gastrointestinal tract can also modulate (e.g., decrease) the absorption of nutrients as the digested nutrients move through the intestine. The presence of the barrier particles creates a decreased surface area of the intestinal lining available to be in contact with digested nutrients and hence results in decreased or delayed absorption of such nutrients. The sucralfate based, hydratable compositions described herein are a potential therapy or add-on therapy for obesity, weight control, insulin resistance, hyperlipidemia, hypertension, and T2DM.

The duration of the sticky pastes formed by the new hydratable compositions in the GI tract is about 2-6 hours followed by degradation and excretion. However, the duration can be tailored to be shorter or longer based on viscosity and charge for specific compositions.

The new compositions can be used to carry and deliver biologically active substances and other materials. The release of the substances and materials from the barrier layer can be controlled and can occur for an extended time period, yet is temporary. In yet another example, one can combine iodine, silver ions, and/or a chlorine-containing substance with the new compositions for attachment and slow release to inhibit the growth and/or proliferation of various microorganisms on surfaces, e.g., in the GI tract.

In any of the methods described herein, the subject is administered a dose of any of the compositions described herein. For example, in any of the methods described herein the subject is administered a dose of any of the hydratable compositions described herein before eating (e.g., before eating a meal). The subject can be administered any of the compositions described herein between about 5 hours and about 1 minute (e.g., 4 hours, 3 hours, 2 hours, between 1.8 hours and 5 minutes, between 1.5 hours and 10 minutes, between 1.3 hours and 15 minutes, between 1.0 hour and 20 minutes, between 50 minutes and 25 minutes, between 40 minutes and 25 minutes, between 5 hours and 3 hours, between 4 hours and 2 hours, between 3 hours, and 1 hour, or between 2.5 hours and 1 hour) before eating (e.g., before eating a meal). In other embodiments, the subject is administered any of the hydratable compositions described herein at substantially the same time as eating (e.g., while eating). The subject can be administered, e.g., one, two, three, four, five, six, or seven doses of any of the compositions described herein a day (e.g., over a total period of at least 1 month, at least 6 weeks, at least 2 months, at least 10 weeks, or at least 3 months). Some examples of the methods provided herein further include monitoring a subject's blood glucose levels and/or weight (e.g., before and after administration (e.g., repeated administration) of any of the compositions provided herein.

In some embodiments, the hydratable compositions described herein may also be used as a vehicle to deliver cells and/or transfection agents. The hydratable compositions described herein may be applied via multiple modalities including direct application, endoscopy, needle, brush, spray, plug, pill, tablet, capsule, and gel-cap. In some embodiments, the particulate, e.g., microparticulate, hydratable compositions described herein are not absorbed by the body of the patient to whom they are administered. In some embodiments, the hydratable compositions can be formulated as a powder, emollient, cream, ointment, or suspension.

In some embodiments, the paste that is obtained by contacting the hydratable composition with a liquid containing water (e.g., at least 45% w/w, or at least 50, 60, 70, 80, 90, 95, or 100%), can be used to coat biological surfaces, e.g., the rectum, vagina, nasal, and skin. In some embodiments, the hydratable compositions can be delivered as a drink, a solution, or an elixir. In some embodiments, the compositions can be administered in a drinking straw form. See, for example, the world-wide-web at pharmaceuticalonline.com/doc/pediatric-drug-delivery-systems-drinking-straw-xstraw-0001.

In some embodiments, the hydratable composition can be used to deliver sensing molecules (e.g., sensors) as well as contrast agents (e.g., microbubbles or radiocontrast agent).

The present disclosure also provides methods to treat topical wounds and burns. The methods include identifying a subject in need of such treatment, and applying the hydratable composition or the paste, which is obtained by contacting the hydratable composition with a liquid containing water to the sites of topical wounds and burns. In some embodiments, the composition is in the form of cream. A method of using sucralfate for treating topical wounds and burns is described in Beheshti, Akram, et al. "Comparison of topical sucralfate and silver sulfadiazine cream in second degree burns in rats," Adv. Clin. Exp. Med., 22(4):481-487 (2013), which is incorporated herein by reference in its entirety. In some embodiments, the composition includes silver sulfadiazine.

In another aspect, the present disclosure also provides a method to promote mucosal healing. The method includes the step of identifying a subject in need of such treatment, and applying the hydratable composition or the paste, which is obtained by contacting the hydratable composition with a liquid containing water, to the sites in need of such treatment. A method of using sucralfate to promote mucosal healing is described in Gupta, Pravin J., et al. "Topical sucralfate treatment of anal fistulotomy wounds: a randomized placebo-controlled trial," Diseases of the Colon & Rectum, 54(6):699-704 (2011), which is incorporated herein by reference in its entirety.

In one aspect, the present disclosure also provides a method to treat dermatitis. The method includes the step of identifying a subject in need of such treatment, and applying the hydratable composition or the paste, which is obtained by contacting the hydratable composition with a liquid containing water, to the sites of dermatitis. A method of using sucralfate to treat dermatitis is described in Markham, Trevor, Fionnuala Kennedy, and Paul Collins. "Topical sucralfate for erosive irritant diaper dermatitis," Archives of Dermatology, 136:10 (2000), which is incorporated herein by reference in its entirety.

Other uses are also contemplated, e.g., treating hemorrhoids, treating venous ulcers, treating infection, etc. Some of these uses, with compositions other than those described herein, are described in, e.g., WO1989005645A1, which is incorporated by reference in its entirety.

Pharmaceutical Formulations and Dosage Forms

Also within the scope of this disclosure are pharmaceutical compositions containing at least one hydratable composition mixed with a biologically active substance described herein, with or without an additional pharmaceutically acceptable carrier. Further, this disclosure covers methods of administering an effective amount of the compounds described herein, e.g., in a pharmaceutical composition, to a patient having T2DB or obesity, e.g., as described herein. "An effective amount" or "an amount effective" refers to the amount of a compound and the one or more biologically active substances that is required to form a barrier on the lining of a portion or portions of the GI tract to deliver the one or more biologically active substances and/or confer a therapeutic effect on the treated patient. Effective doses will vary, as recognized by those skilled in the art, depending on the types of diseases treated, route of administration, excipient usage, and the possibility of co-usage with other therapeutic treatment. In some embodiments, hydratable compositions can be mixed with a biologically active substance at a biologically active substance to LuCl ratio of about 1:1, about 1:10, about 2:10, about 3:10, about 4:10, about 5:10, about 6:10, about 7:10, about 8:10, about 9:10, about 10:1, about 10:2, about 10:3, about 10:4, about 10:5, about 10:6, about 10:7, about 10:8, or about 10:9.

Dosage, toxicity, and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Exemplary doses can range from about 4 g/day for an adult to a maximum dose of sucralfate of about 8 g/day for adult (~114 mg/kg for 70 kg adult). For the new hydratable compositions the dosages can be higher, from about 20 to about 50 g/day, with the potential to be administered in a liquid form, because of the significantly lower level of aluminum in the new compositions compared to sucralfate alone. In other examples, the dose can be between about 1 g/day to about 8 g/day (e.g., between 2 g/day to about 7 g/day).

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound described above. Examples of other carriers include colloidal silicon oxide, magnesium stearate, cellulose, sodium lauryl sulfate, and D&C Yellow #10.

The therapeutic compounds can also be prepared with carriers that will protect the therapeutic compounds against rapid elimination from the body, such as a controlled release formulation. Biodegradable, biocompatible polymers can be used, such as ethylene vinyl acetate, polyanhydrides, polyglycolic acid, collagen, polyorthoesters, and polylactic acid. The new compositions can be incorporated into controlled release formulations to modulate cranio-caudal distribution and retention time. Examples using such formulations are included below (examples 6 and 7). In addition, these formulations can be used to control the duration of the desired effects, for example, by altering the charge and/or viscosity of the overall formulation. In addition, the new compositions can be mixed with, e.g., "doped" with, additional drugs and can then be used as a drug delivery system.

Such formulations can be prepared using standard techniques, or obtained commercially, e.g., from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

Some compositions and pharmaceutical compositions can include a dry acid salt or a liquid acid salt (e.g., any of the exemplary dry acid salts or liquid acid salts described herein or known in the art). Such compositions and pharmaceutical compositions can be wetted with an aqueous solution before being administered to a subject or patient (e.g., administered to the small intestine of a subject).

The pharmaceutical compositions can be included in a container, pack, or dispenser together with instructions for administration.

Methods of formulating suitable pharmaceutical compositions are known in the art, see, e.g., the books in the series *Drugs and the Pharmaceutical Sciences: a Series of Textbooks and Monographs* (Dekker, NY).

The compositions described herein can be preliminarily screened for their efficacy in treating above-described diseases by the whole-organism screening methods described herein and then confirmed by additional animal experiments and clinic trials. Other screening methods will also be apparent to those of ordinary skill in the art.

EXAMPLES

The invention described herein is a novel formulation of a polymer that can form a mucoadhesive layer on the intestinal wall, and hence act as a barrier to the absorption of digested nutrients traveling through the digestive tract. The invention is further described in the following examples, which do not limit the scope of the invention described in the claims.

Example 1—Method for Making a Hydratable Composition

The following method was used to fabricate an AF-LuCI particle composition that forms a viscous sticky paste in water without requirement of acid.

One gram of sucralfate (Heisen Pharmaceutical, China) was added in a 20 ml glass vial, added with 10 ml of 0.1-1.0N HCl solutions in water, and immediately vortexed in 3000 rpm for 10 seconds to form a viscous precipitation. The supernatant solution was removed and 10 ml of methanol, ethanol, isopropanol, or crude reagent alcohol was added. The vial was vortexed in 3000 rpm for 30 seconds to obtain a white particle suspension. The particles were precipitated using centrifugation (1000 rpm for 1 minute) or gravitational precipitation and the supernatant was removed.

In another test, instead of using solvents to dehydrate the acidified sucralfate paste, microwave-assisted drying was used to prepare AF-LuCI particles. One gram of sucralfate (Heisen Pharmaceutical, China) was added in a 20 ml glass vial, added with 10 ml of 0.1-1.0 N HCl solutions in water, and immediately vortexed in 3000 rpm for 10 seconds to form a viscous precipitation. The microwave drying process was performed with a microwave oven (power: 800 W) for 30 seconds.

The white particles were further dried using air-drying for more than 12 hours or under vacuum for at least 1 hour. The dried particles were ground using a mortar and pestle to formulate into white powders. The powders were stored in a closed glass vial in room temperature before use. The chemical status of sucralfate and AF-LuCI particles were evaluated using FT-IR (Bruker, measured from 500 cm-1 to 4000 cm-1 in wavenumber) and TGA (Perkin Elmer, measured from 20° C. to 800° C.). The key differences in prior sucralfate compositions (referred to herein as LuCI-X) and the new AF-LuCI particle fabrication methods are described in Table 1 below.

TABLE 1

| Formulation | LuCI-X particle | AF-LuCI Particle |
|---|---|---|
| Particle fabrication | Acidified sucralfate paste is solidified in pH 7.4 and stabilized using phosphate ions to formulate into particles. | Acidified sucralfate paste is dehydrated using alcohol to formulate into particles. |
| Humectant requirement | A humectant (e.g., carrageenan) is required to form a paste in acid. | No humectant is required and capable to form a paste in any aqueous solutions. |
| Final drying | The final product is suspended in water (requires freeze-drying or long vacuum drying in high temperature). | The final product is suspended in volatile alcohol that can be easily dried. |

In one test, in solvent-based dehydration, the acidified sucralfate paste was added with excess amount of water-miscible common solvents (e.g., ethanol, methanol, dimethylsulfoxide (DMSO), acetone, etc.), and stirred to form a suspension in brittle particle form that is further dried in vacuum to evaporate solvents. In microwave-assisted dehydration, the acidified sucralfate paste was placed in a microwave oven, exposed to 1200 W microwave for 30 sec and ground into white powder using mortar and pestle. Briefly, to fabricate the dry particles using solvent-based dehydration, sucralfate was first treated with acid (0.3-0.8N HCl solutions) to form a viscous sticky paste that was further combined with water-soluble solvents (e.g., alcohol, acetone, DMSO, DMF, etc.) and vortexed resulting in a white particle suspension. The suspension was then dried to remove the solvent and the dried particles were further ground to form a white powder.

Example 2—Aluminum Content and Release from the Hydratable Compositions

Aluminum contents of sucralfate and AF-LuCI particles were measured using the colorimetric method recommended by USP. Briefly, about 1.0 g of sucralfate or AF-LuCI particle was transferred to a 250 mL volumetric flask, 10 mL of 6.0 N hydrochloric acid was added, mixed, and heated with continuous stirring in a water bath at 70° C. for 5 minutes. The solution was cooled to room temperature, diluted with water to volume, and mixed. The solution was filtered, discarding the first portion of the filtrate. Twenty-five milliliter of the filtrate was transferred to a 250 mL beaker, 25 mL of 0.05 M edetate disodium was added, 20 mL of acetic acid-ammonium acetate buffer was added, and mixed. The solution was heated in a water bath at 70° C. for 5 minutes. The resultant solution was cooled to room temperature, added with 50 mL of alcohol and 2 mL of dithizone, and mixed. The solution was then titrated with 0.05 M zinc sulfate until they form a bright rose-pink color. Each mL of 0.05 M edetate disodium consumed is equivalent to 1.349 mg of aluminum.

Because a part of aluminum content is released upon the acid treatment, the AF-LuCI contains significantly lower aluminum content compared to the native sucralfate (USP regulation on the aluminum content of sucralfate is 15.5-18.5 w/w % of the total weight). FIG. 5 shows the aluminum contents of sucralfate and AF-LuCIs. The AF-LuCI particles contain significantly lower aluminum content (lower than 15 w/w % of the total weight) compared to the native sucralfate (USP regulation on the aluminum content of sucralfate is 15.5-18.5 w/w % of the total weight).

Figure 6:
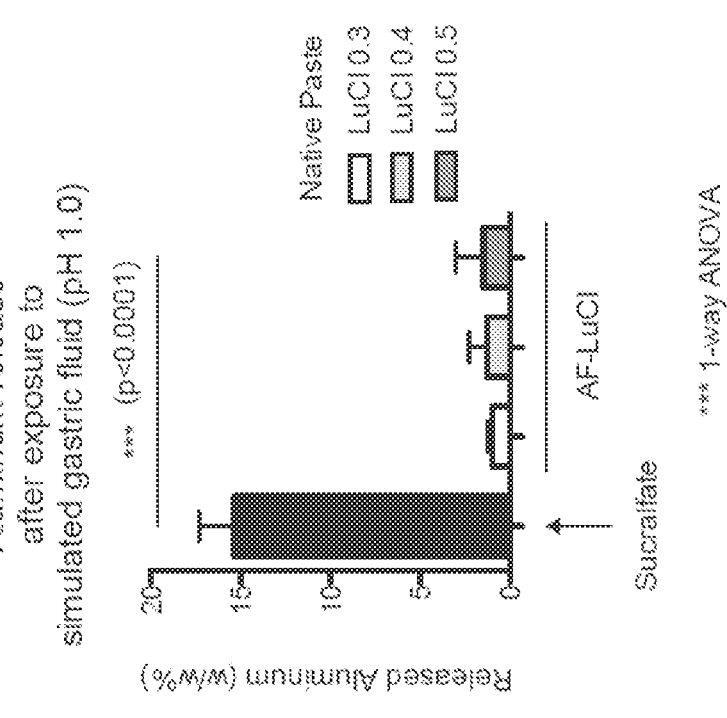
FIG. 6 is a bar graph showing the release of the aluminum components from sucralfate vs. AF-LuCI in simulated gastric fluid (simulated gastric fluid (SGF), pH 1.0).

As shown in FIG. 6, when exposed to simulated gastric fluid (SGF, pH 1.0), the release of aluminum from AF-LuCIs was significantly lower (less than 2 w/w % of total aluminum content of AF-LuCI particle) compared to sucralfate (15 w/w % of total aluminum content of sucralfate). Moreover when exposed to simulated duodenal fluid (SDF, pH 3.5) or simulated intestinal fluid (SIF, pH 6.5), the aluminum release from AF-LuCI was undetectable using the colorimetric methods suggesting the enhanced safety for long-term use.

Example 3—Thermogravimetric Analysis (TGA) and Fourier Transform-Infrared (FT-IR)

Figures 7A, 7B, 7C, 7D:
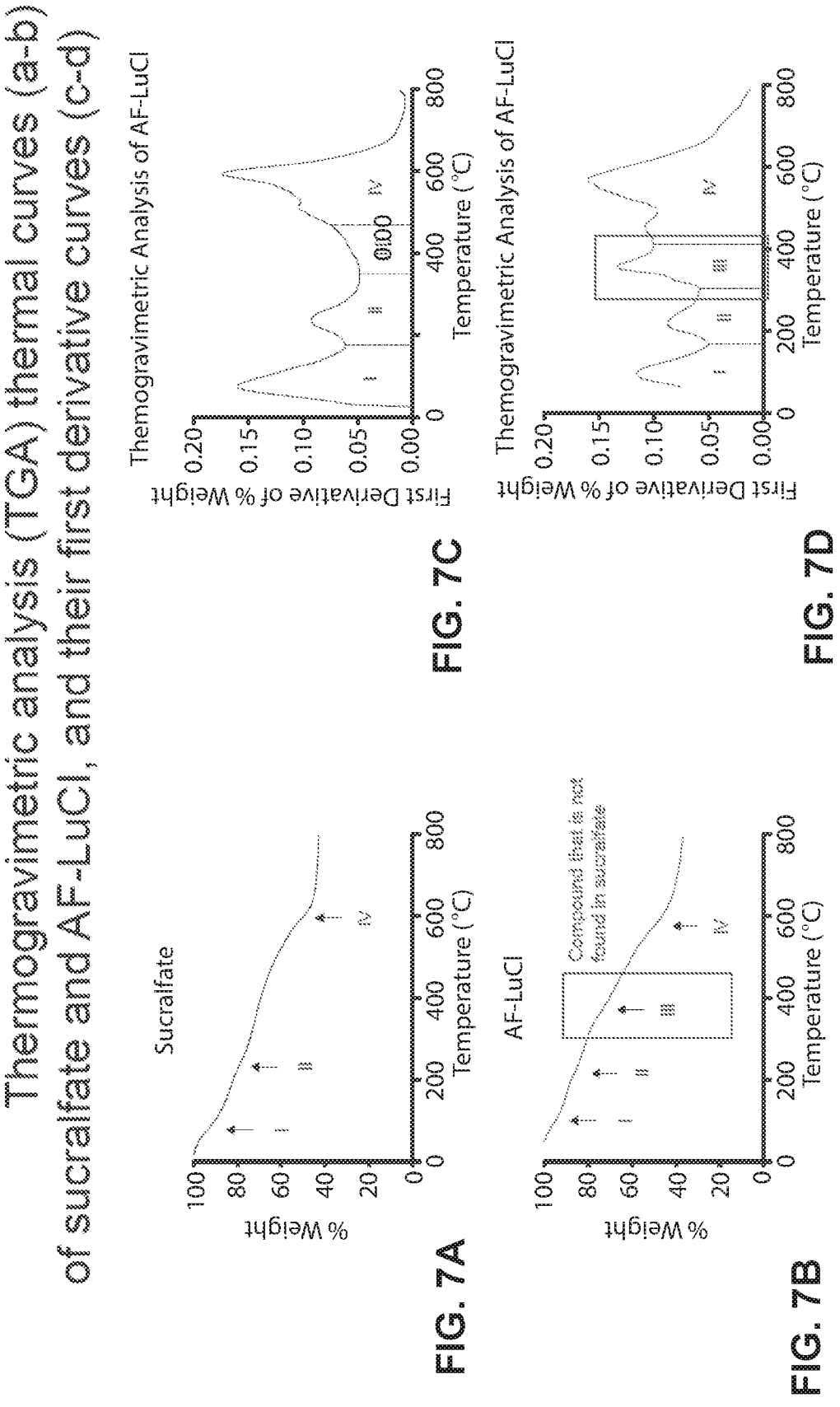
FIGS. 7A to 7D are a series of graphs that show thermogravimetric analysis (TGA) of sucralfate (thermal curve in FIG. 7A and first derivative curve in FIG. 7C) and AF-LuCI (thermal curve in FIG. 7B and first derivative curve in FIG. 7D) measured from 20° C. to 800° C.

The chemical composition was further evaluated in detail using thermogravimetric analysis (TGA) and the Fourier Transform-Infrared (FT-IR). As shown in FIGS. 7A-D, the TGA thermal curve of AF-LuCI showed a distinctive weight loss at 340-400° C. that was not found in the thermal curve of sucralfate suggesting that AF-LuCI has a component (i.e. poly aluminum complex) that does not exist in sucralfate. In particular, FIG. 7 shows the thermogravimetric analysis (TGA) thermal curve of (7a) sucralfate and (7b) AF-LuCI measured from 20° C. to 800° C. (c-d). The first derivative curves of (7c) graph (7a) (sucralfate) and (7d) graph (7b) (AF-LuCI) were also shown for clearer distinction of each segment. The TGA thermal curve of AF-LuCI showed a distinctive weight loss at 340-400° C. that was not found in the thermal curve of sucralfate suggesting that AF-LuCI has a component (i.e. poly aluminum complex) that does not exist in sucralfate.

Figure 8:
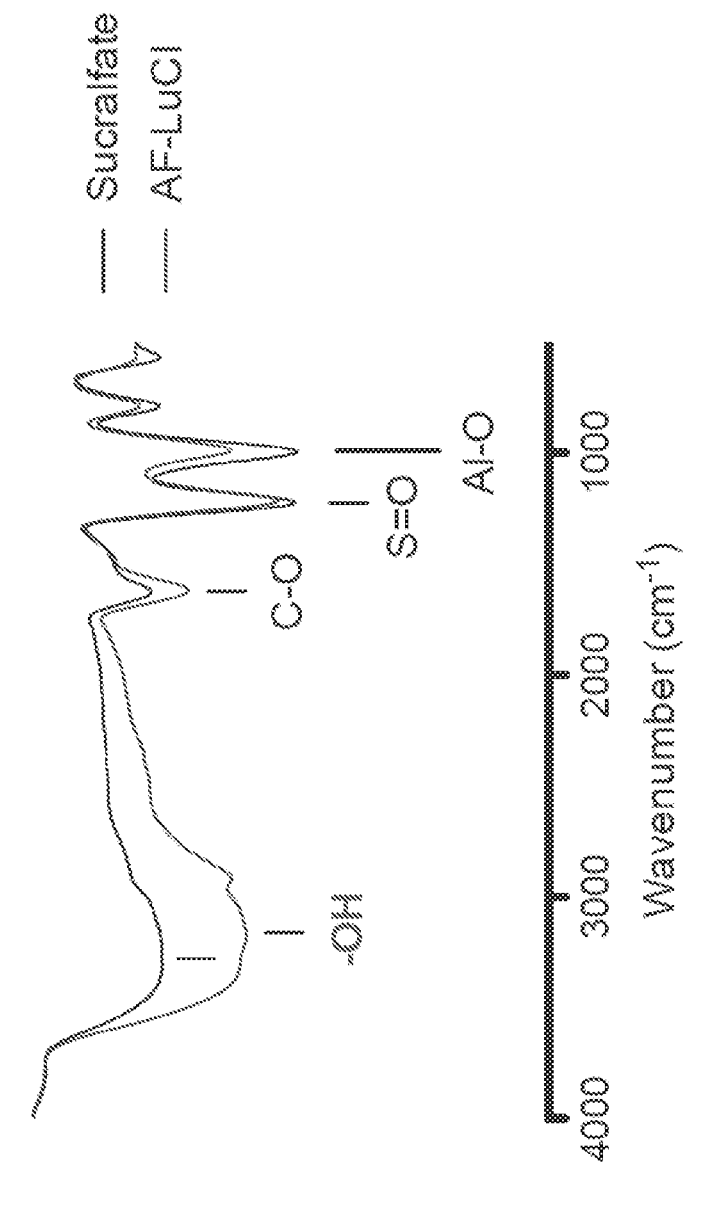
FIG. 8 is a representation of FT-IR spectra of sucralfate and AF-LuCI. The spectrum of AF-LuCI has a broad peak for —OH stretching at 3174 cm$^{-1}$ whereas sucralfate has a broad peak for —OH stretching at 3312 cm$^{-1}$ suggesting the —OH is in lower energy state indicating the —OH is more strongly bound to aluminum ions in poly aluminum complex compared to the —OH bound in aluminum hydroxide (Al (OH)$_3$) in sucralfate.

The relatively high temperature for the weight loss of AF-LuCI (340-400° C.) compared to the thermal oxidation of aluminum hydroxide ($Al(OH)_3$) in sucralfate indicates that the new component in AF-LuCI requires higher energy to get oxidized supporting the presence of poly aluminum complex. In addition, as shown in FIG. 8, the FT-IR spectrum of the AF-LuCI showed a broad peak for —OH stretching at 3174 cm$^{-1}$ whereas sucralfate has a broad peak for —OH stretching at 3312 cm$^{-1}$ suggesting the —OH is in lower energy state indicating the —OH is more strongly bound to aluminum ions in poly aluminum complex compared to the —OH bound in aluminum hydroxide ($Al(OH)_3$) in sucralfate. Interestingly, FT-IR spectra of the paste formed by hydration of AF-LuCI and the acidified sucralfate pastes were closely similar indicating that they have similar chemical structures when they are hydrated to form paste in GI tract.

Example 4—Viscosity Measurements of AF-LuCI Hydratable Compositions

The mechanical properties of 1 w/v % material solutions in simulated stomach gastric fluid (SGF) were analyzed using a rheometer (AR-G2, TA Instruments). The dynamic viscosity of each material solution was measured using a 20 mm plate with 200 μm gaps (shear rate: 0.01-100 1/s in log scale, shear rate of 1 1/s was selected to compare viscosity of materials).

When the fabricated dry AF-LuCI particles were exposed to water, they rapidly formed a viscous sticky paste that had similar viscosity with the acid-treated sucralfate paste. This paste formation process had a few aspects that are quite distinct from the paste formation process of sucralfate, and that are clearly beneficial to form a coating layer in contact with wet surface (i.e. luminal surface of gut). The AF-LuCI particles could form the viscous sticky paste in all the pH that can be found in GI tract (i.e. pH 1-7).

Figure 9:
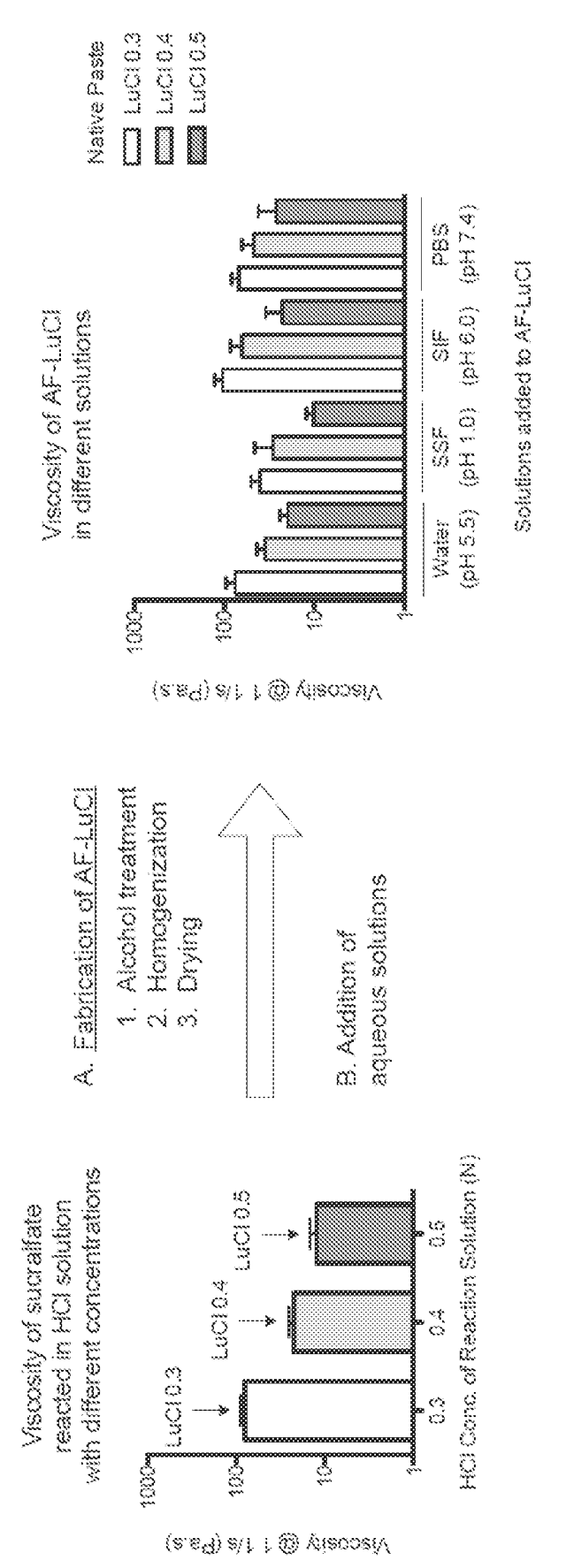
FIG. 9 is a pair of bar graphs showing the viscosity of acidified sucralfate paste (left graph) and hydrated AF-LuCI (right graph). Sucralfate pastes were fabricated from different concentration of HCl solution (0.3-0.5N) and were treated with ethanol to fabricate AF-LuCIs. The AF-LuCI particles could form the viscous sticky paste in all the pH that can be found in GI tract (i.e. pH 1-7).

In particular, FIG. 9 shows the viscosity of acidified sucralfate paste and hydrated AF-LuCI. The left graphs shows the results for sucralfate pastes fabricated from different concentration of HCl solution (0.3-0.5N) and were treated with ethanol to fabricate AF-LuCIs. The right graph shows the results of AF-LuCI particles that could form the viscous sticky paste in all the pH that can be found in GI tract (i.e. pH 1-7).

When the AF-LuCI particles were exposed to simulated gastric fluid (SGF, pH 1.0), simulated duodenal fluid (SDF, pH 3.5), simulated intestinal fluid (SIF, pH 6.5), and phosphate buffered saline (PBS, pH 7.4), they all generated similar viscous sticky pastes. For example, when the acidified sucralfate paste with the viscosity of 80 Pa·s was used to fabricate AF-LuCI, the resultant AF-LuCI particles could form pastes with the viscosity of 77 Pa·s, 41 Pa·s, 105 Pa·s, and 70 Pa·s in distilled water (pH 5.5), SGF, SIF, and PBS, respectively. The viscosity of the paste from AF-LuCI hydration was tunable using acidified sucralfate pastes with different viscosities. When the acidified sucralfate pastes with the viscosities of 80, 22, and 12 Pa·s were treated with alcohol to fabricate AF-LuCI, the resultant AF-LuCI particles could form the viscous pastes in distilled water with the viscosities of 77, 36, and 20 Pa·s.

Moreover, given that it is a rehydration process and the water content in the original paste that AF-LuCI was made from is about 5-20 w/w %, only minimal amount of water was required to generate the viscous sticky paste, whereas sucralfate requires at least 0.6-0.8 equivalents of acid for the reaction to generate the similar paste. This is clearly beneficial to form a coating instantly after contact with the wet luminal surface of gut.

Example 5—Film Thickness of Hydrated AF-LuCI Hydratable Compositions

Five hundred milligrams of AF-LuCI (excess) was added onto mucus-coated cellulose nitrate membrane (disk shape with 2 cm diameter) and DDW (pH 5.5), SGF (pH 1.0), or SIF (pH 6.5) was added immediately. After AF-LuCI becomes a paste and flow to form a layer (3-5 minutes), supernatant was removed and the paste-coated membrane was quickly frozen in −80° C. freezer to measure the thickness. The thickness of the mucus-coated cellulose nitrate membrane without AF-LuCI was separately measured as a baseline.

Figure 10:
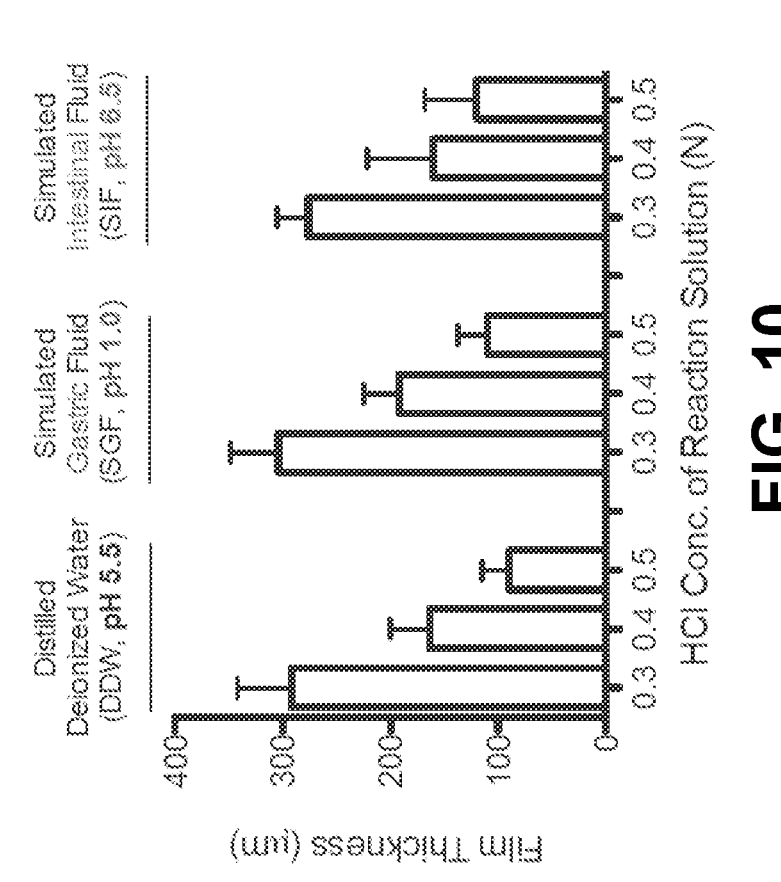
FIG. 10 is a bar graph showing the thickness of a layer formed by hydrated AF-LuCI paste. The AF-LuCI could form a layer of paste in contact with mucus surface in the GI tract including stomach (pH 1-3) and intestine (pH higher than 6).

The AF-LuCI could form a layer of paste in contact with mucus surface in GI tract including stomach (pH 1-3) and intestine (pH higher than 6). When AF-LuCI powders were added onto the mucus-coated cellulose nitrate membrane and added with distilled water (pH 5.5), SGF (pH 1.0), or SIF (pH 6.5), they could form a paste that slowly flowed over the mucus membrane to form a continuous layer with the thickness of 100-300 μm (FIG. 10). Sucralfate formed ~250 μm layer on the mucus-coated cellulose nitrate membrane only in SGF (pH 1.0) whereas it did not form any layer in distilled water or SIF.

Example 6—Stability of Hydrated AF-LuCI Hydratable Compositions

Five hundred milligrams of AF-LuCI (excess) was added onto mucus-coated cellulose nitrate membrane (disk shape with 2 cm diameter) and SIF (pH 6.5) was added immediately. After AF-LuCI became a paste and flow to form a layer (3-5 minutes), AF-LuCI coated membrane was placed on a 10 cm petri dish with 5 ml of SIF (pH 6.5). The petri dish was placed in a shaking incubator in 37° C. shaking in 500 rpm for 1 or 2 hours to apply shear as a test of stability over time. At the end of the selected time period, the AF-LuCI coated membrane was quickly frozen in −80° C. freezer to measure the thickness as a measure of stability. The thickness of the mucus-coated cellulose nitrate membrane without AF-LuCI was separately measured as a baseline.

Figure 11:
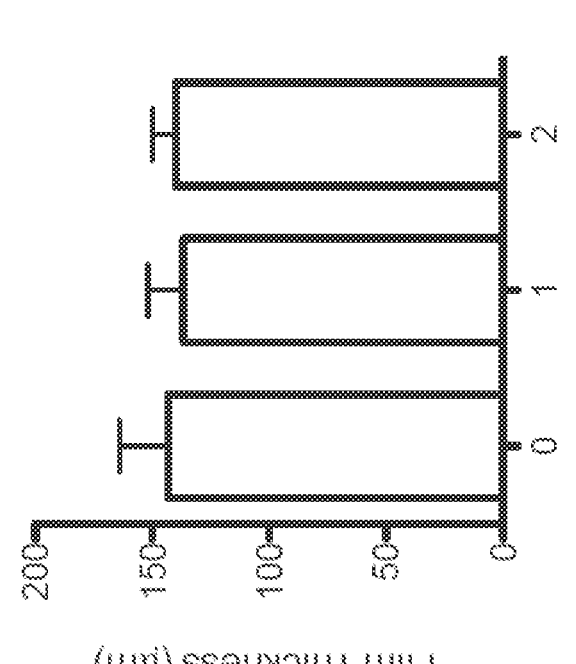
FIG. 11 is a bar graph showing the resistance to shear stress of the hydrated AF-LuCI pastes. The layer formed on mucus surface remains stable for at least 2 hours.

As shown in FIG. 11 the layer formed on mucus surface remains stable (no change in thickness) for at least 2 hours. These results indicate that the AF-LuCI particles can form a continuous layer on gut and the layer formed on the luminal mucus surface of gut should stay on the initial adhesion site during the duration of meal (i.e., 30-60 minutes and up to 2 hours) and have minimal change of the barrier properties during the meal.

Example 7—Swelling of Hydrated AF-LuCI Hydratable Composition Pastes

Five hundred milligrams of AF-LuCI 0.4 (excess) was added onto mucus-coated cellulose nitrate membrane (disk shape with 2 cm diameter) and SIF (pH 6.5) was added immediately. After AF-LuCI becomes a paste and flow to form a layer (3-5 minutes), AF-LuCI coated membrane was placed on a 10 cm petri dish with 10 ml of SGF (pH 1.0) or 10 ml of SIF (pH 6.5). The petri dish was placed in an incubator in 37° C. without shaking for 30, 60, and 120 minutes. The wet weights of resultant AF-LuCI coated membranes were measured to calculate swelling of AF-LuCI paste. The weight of the mucus-coated cellulose nitrate membrane without AF-LuCI was separately measured as a baseline.

Figure 12:
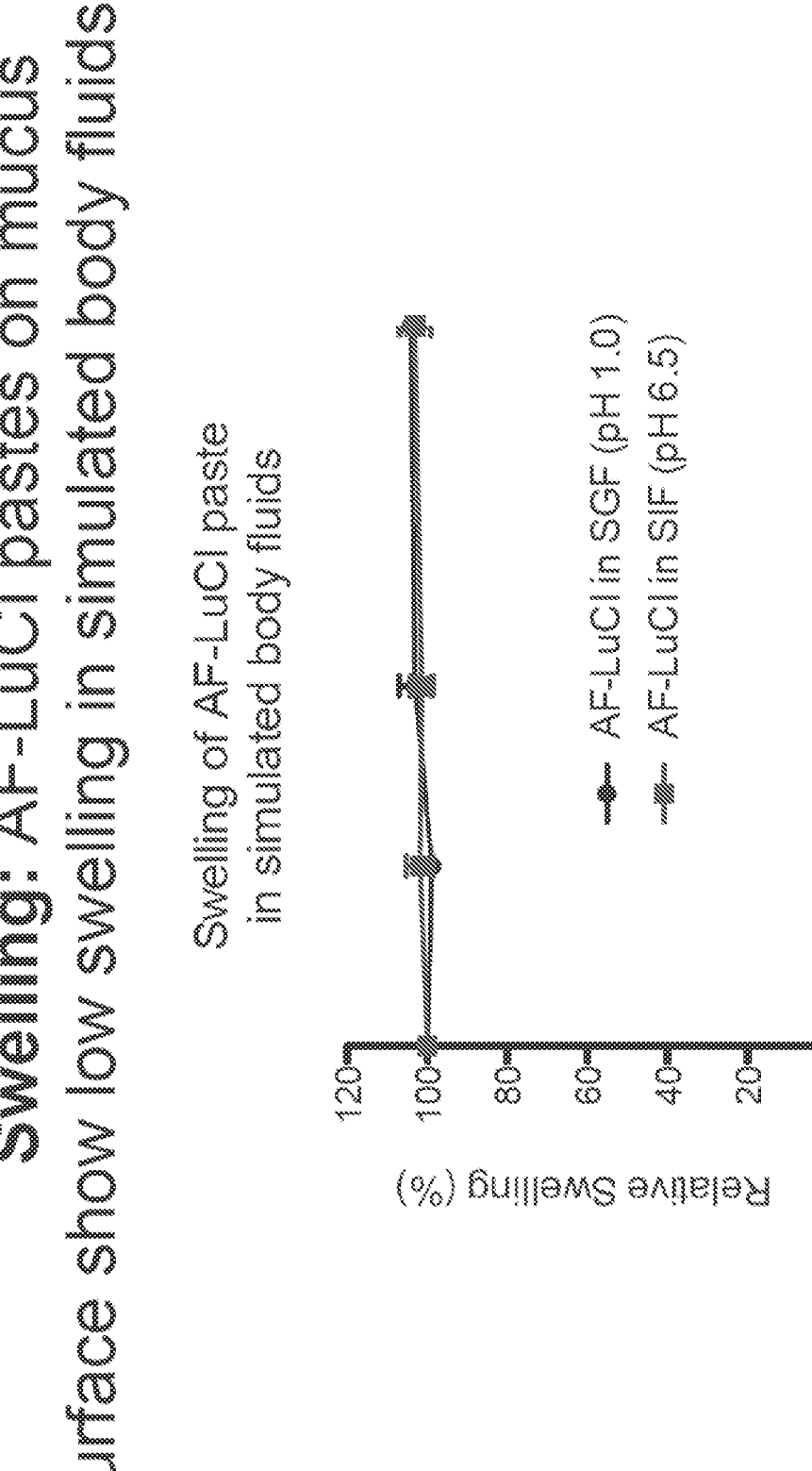
FIG. 12 is a graph showing the swelling of the hydrated AF-LuCI pastes. The hydrated AF-LuCI pastes showed significantly low swelling less than 5 w/w % for at least 2 hours in both SGF (pH 1.0) and simulated intestinal fluid (SIF)(pH 6.5).

As shown in FIG. 12, the layer formed on mucus surface showed significantly low swelling, less than 5 w/w %, for at least 2 hours in both SGF (pH 1.0) and SIF (pH 6.5). These results further indicate that the AF-LuCI particles can form a continuous layer on gut and the layer formed on the luminal mucus surface of gut should stay on the initial adhesion site during the duration of meal (i.e. 30-60 minutes) and have minimal change of the barrier properties during meal.

Example 8—Integrative Barrier Property Test Using Mucin-Coated Membranes

To examine the barrier properties of pastes formed from the new hydratable compositions in vitro, a mucin-coated membrane was prepared to mimic the mucus surface of the intestine. Specifically, a cellulose nitrate membrane (pore size: 0.2 μm, Whatman, Germany) was incubated in a 3% w/v porcine stomach mucin (Sigma Aldrich, USA) solution in PBS (pH 7.4) and gently shaken for 2 hours at room temperature. The membrane was washed with distilled deionized water (DDW, pH 5.5) to remove the excess mucin solution. The mucin-coated membranes were used within 1 hour following preparation.

To measure the thickness of the mucin layer, the mucin-coated membrane was lyophilized and imaged using scanning electron microscope (SEM) and the thickness of randomly selected positions was examined (average mucin layer thickness: ~100 μm). To test the nutrient barrier properties, 10 mg of sucralfate or AF-LuCI was added evenly to a mucin-coated membrane and vertically tilted for 1 minute. The material-attached to the mucin-coated membrane was mounted in the Franz-cell system and three milliliters of glucose solution (120 g/L) was added and samples were collected from the receiver part of the system after 5 minutes.

The permeation tests were performed in triplicate for each material. The glucose concentration was measured using high performance liquid chromatography (HPLC, Agilent, USA) with an analytical C18 column (Zorbax Eclipse XDB-C18, Agilent). The flow rate was 1 ml/min, the eluent was DDW, and the wavelength of UV detector was 195 nm. All results were normalized to a mucin-coated membrane without application of a test material (0% blocked).

Figure 13:
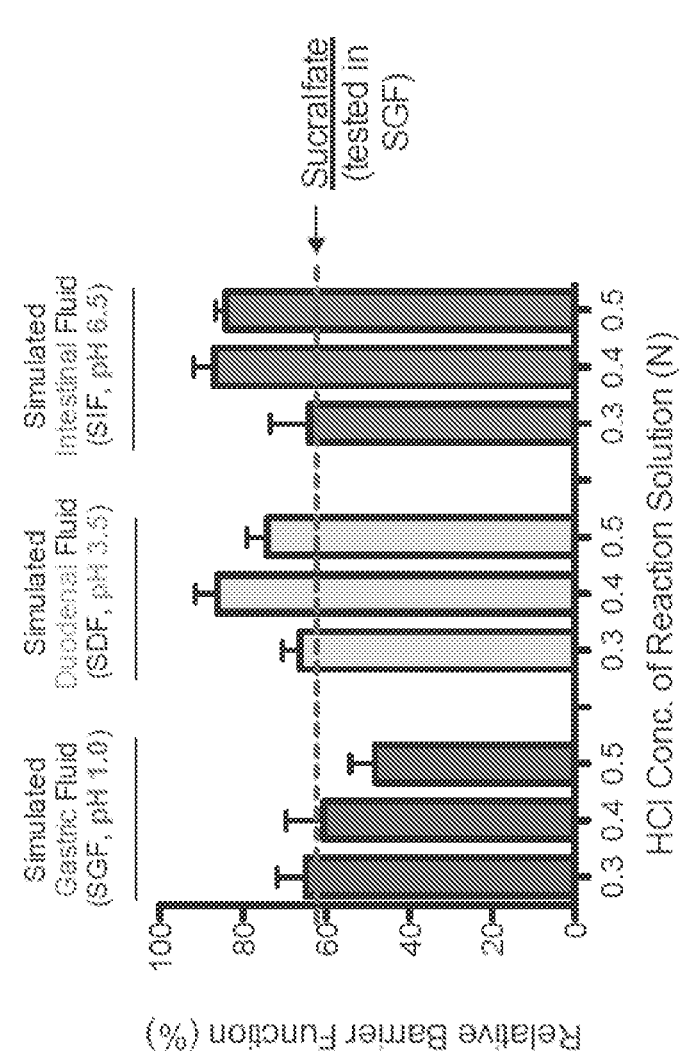
FIG. 13 is a series of bar graphs showing the barrier properties of AF-LuCI particles. The AF-LuCI particles showed excellent barrier properties on mucus substrate in SGF (pH 1.0), simulate duodenal fluid (SDF)(pH 3.5) and SIF (pH 6.5).

As shown in FIG. 13, the AF-LuCI particles showed excellent barrier properties on mucus substrate in SGF (pH 1.0), SDF (pH 3.5) and SIF (pH 6.5). In SGF, AF-LuCIs could block 40-70% of glucose penetration, and in higher pH environment using SDF and SGF, AF-LuCIs showed more enhanced barrier function (65-90% glucose blocked) that was higher than the barrier function of sucralfate in SGF (~60%). This enhanced barrier function is due to the formation of strong layer on the freshly harvested gut mucosa, and seems closely related to mucoadhesion of AF-LuCI.

Thus, when hydrated, the composition forms a barrier that when prepared at 10 mg/ml and applied to 1 cm$^2$ surface area cellulose nitrate filter with 0.45 micron holes in a Franz diffusion chamber exhibits less than 60% permeation of glucose 5 minutes after addition of 120 g/L glucose solution to the top chamber, and more preferably less than 40% permeation.

Example 9—In Vivo Evaluation of the Effect of AF-LuCI on Glucose Tolerance

Male Sprague Dawley (SD) rats between 330 and 350 grams were fasted overnight from 7 pm the night preceding the oral glucose tolerance test (15 hours). Two different formulations (hydrated paste and dry particles encapsulated in capsules) were tested. For the hydrated paste, 180 mg of AF-LuCI particles were hydrated using 0.9% normal saline before each gavage. The hydrated pastes were gavaged into stomach using gavage needles.

After oral gavages the animals were allowed access to water ad libitum. Rats gavaged with 0.9% normal saline were used as controls. Three hours after administration of capsules all animals underwent an oral glucose tolerance test (OGTT). In brief, all rats were gavaged with a glucose solution of 2 g/kg. Blood samples were collected prior to and 15, 30, 60, 90 and 120 minutes after administration of glucose solution. Blood was collected from the tail vein with a 30 gauge needle to measure blood glucose level using a glucometer (OneTouch UltraSmart®, LifeScan Inc., USA).

For the dry particle formulation, AF-LuCI particles were encapsulated in a hard gelatin capsule (Torpac®) to deliver compounds via oral gavage. Each capsule contained 30 mg of AF-LuCI particles. The 100% soluble capsules dissolve rapidly and completely in the stomach without enteric coating. Six capsules (total dose: 180 mg) were used without further coating and six capsules were manually covered with enteric coating ((15 w/v % Eudragit L100-55, 0.1 w/v % triethyl citrate (plasticizer), 0.5 w/v % talc (anti-tack) in 9.5 ml methanol and 0.5 ml water)) to ensure targeted delivery to the lower GI tract. Gavaging the capsules required an appropriate pill gavage needle and briefly anesthetizing the rats with isoflurane in oxygen. After oral gavages the animals were allowed to recover and access to water ad libitum. Rats gavaged with the same number of empty non-coated capsules were used as controls. Three hours after administration of capsules all animals underwent an OGTT as described above.

AF-LuCI particles were able to inhibit glucose response in SD rats with oral administration in both pre-hydrated formulation and dry formulation in capsules (FIGS. 14A-D). Rats gavaged with the hydrated formulation showed 18.7% reduction of glucose response (area under curve, AUC) and rats gavaged with the dry-capsules in non-coated capsules showed 19.2% reduction. Enteric-coated capsules that prevent release of AF-LuCI in the stomach and release particles in duodenum were also tested. With administration of enteric-coated capsules over three hours, rats showed 17.8% reduction in glucose response indicating the paste formed in duodenum can also block the nutrient sensing and absorption.

Figures 14A, 14B, 14C, 14D:
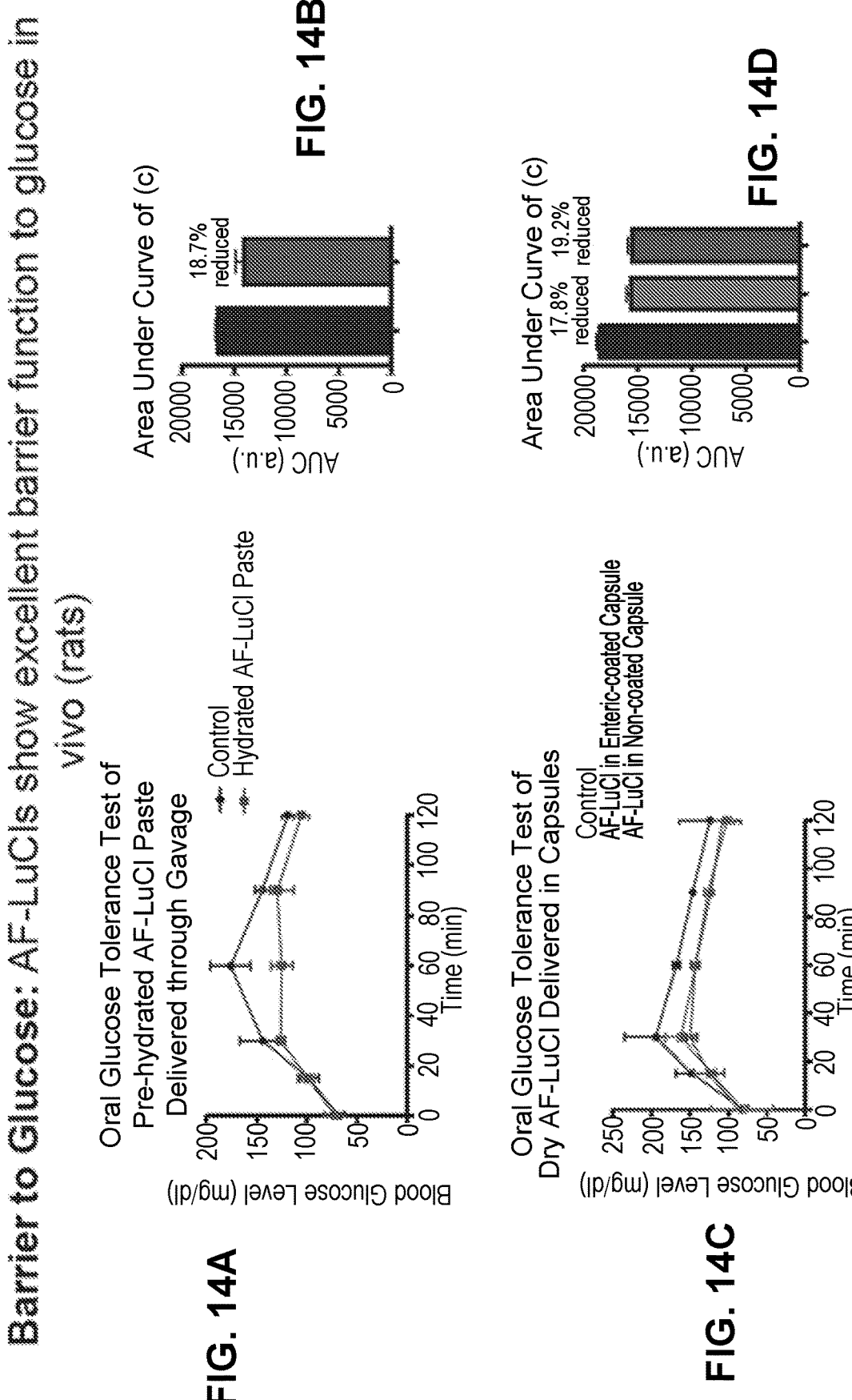
FIG. 14A is a graph showing the oral glucose tolerance test (OGTT) curves of rats gavaged with hydrated AF-LuCI (180 mg before hydration) and rats gavaged with the same amount of saline.
FIG. 14B is a bar graph showing the area under curve (AUC) of the OGTT curves in FIG. 14A.
FIG. 14C is a graph showing the OGTT curves of rats gavaged with non-coated gelatin capsules containing 180 mg of dry AF-LuCI, rats gavaged with enteric-coated gelatin capsules containing 180 mg of dry AF-LuCI, and rats gavaged with empty non-coated gelatin capsules.
FIG. 14D is a bar graph showing the AUC of the OGTT curves in FIG. 14A.

In particular, FIG. 14A shows the OGTT curves of rats gavaged with hydrated AF-LuCI (180 mg before hydration) and rats gavaged with the same amount of saline. FIG. 14B shows the area under curve (AUC) of the OGTT curves in FIG. 14A. FIG. 14C shows the OGTT curves of rats gavaged with non-coated gelatin capsules containing 180 mg of dry AF-LuCI, rats gavaged with enteric-coated gelatin capsules containing 180 mg of dry AF-LuCI, and rats gavaged with empty non-coated gelatin capsules. FIG. 14D shows the AUC of the OGTT curves in FIG. 14A. OGTT curves of rats gavaged with AF-LuCI in different formulations showed significant reduction of glucose response.

These in vivo results indicate that an oral administration of AF-LuCI in capsules can ensure successful decrease in glucose tolerance by possibly forming a mucoadhesive barrier in a targeted region of the GI tract (i.e. stomach and intestine).

Example 10—Polymerization of PAC in AF-LuCI

Experiments were performed to determine the degree of polymerization in AF-LuCI by using the titration-based methods as described in Nail, S. L., White, J. L. & Hem, S. L. Structure of Aluminum Hydroxide Gel I. Initial Precipitate. Journal of Pharmaceutical Sciences 65, 1188-1191 (1976); and Hem, J. D. & Roberson, C. E. Form and stability of aluminum hydroxide complexes in dilute solution. Geol Surv Water-Supply Pap (US); (United States) (1967). The degree of polymerization of PACs in AF-LuCI and sucralfate molecule was determined using titration method based on the reversible protonation of hydroxo linkages in the PAC backbone. Approximately 10 mg of AF-LuCI were treated with 0.1N, 0.2N, 0.3N, 0.4N and 0.5N HCl solutions in different tubes. The samples were vortexed for 5 seconds followed by 1-hour incubation. The supernatant of each sample was then collected and the pH was measured using a pH meter. The same procedures were performed with sucralfate. The pH of the HCl solutions was measured as the control group and the difference between the control and the treated groups was calculated. The difference in pH corresponds to the proton consumption and the amount of hydroxo linkages that were then used to calculate the number of aluminum per molecule.

Figure 15:
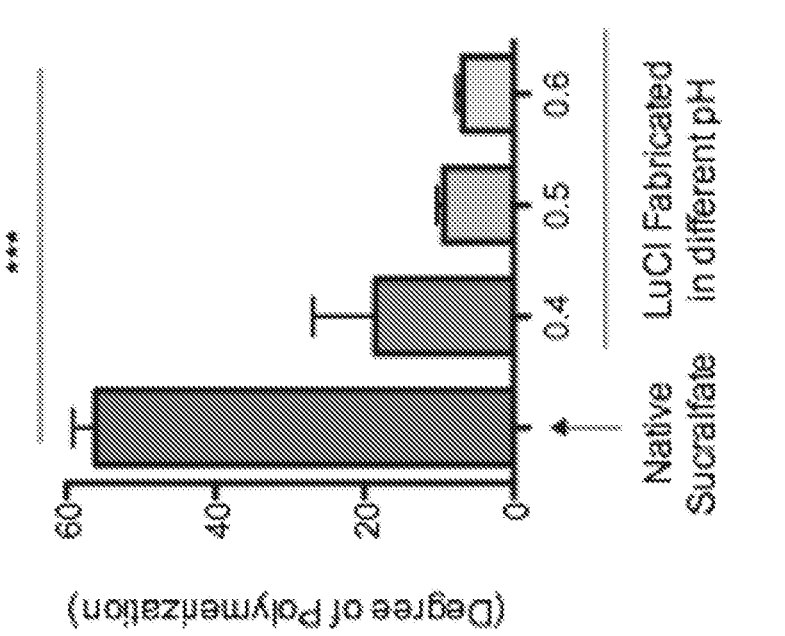
FIG. 15 is a graph showing degree of polymerization of PAC in sucralfate and AF-LuCI measured using titration method calculating the number of hydroxo linkages per aluminum.

The degree of polymerization of PAC in AF-LuCI (i.e. number of aluminum ions per PAC molecule) and the native sucralfate was analyzed. The numbers of aluminum ions per molecule of AF-LuCIs (18.6±8.4, 9.4±0.9, and 6.9±0.8 for AF-LuCIs fabricated using 0.4N, 0.5N, and 0.6N HCl solutions, respectively) were significantly lower than that of sucralfate (56.1±3.0 aluminum per molecule) (FIG. 15). FIG. 15 shows that PAC polymers in AF-LuCI are significantly shorter than in sucralfate indicating the polymers are less pH dependent and capable of forming liquid complex coacervate with anionic sucrose octasulfate (***<0.0001 in One-way ANOVA).

Example 11—Properties of Rehydrated Pastes

Figure 16:
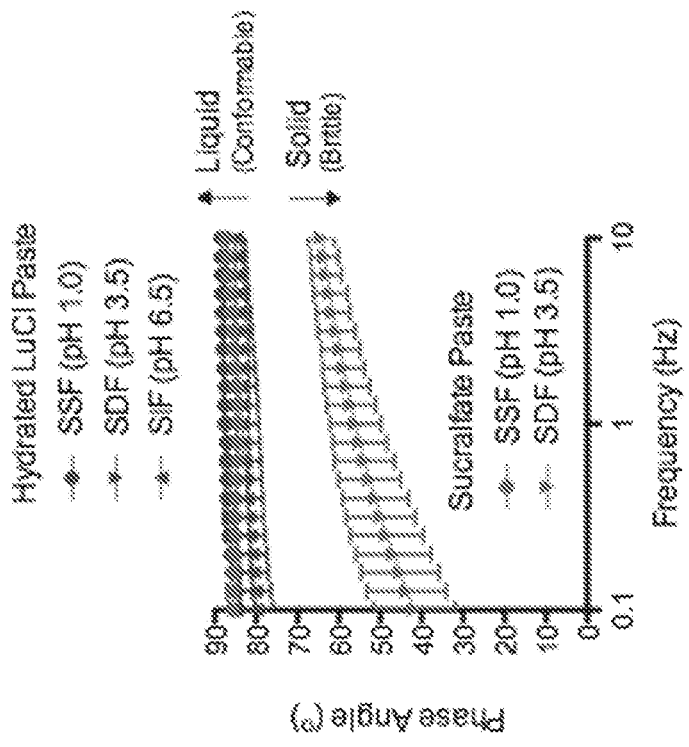
FIG. 16 is a graph showing change of rheological properties of dried AF-LuCI powder re-hydrated in different simulated gastrointestinal fluids.

Experiments were also performed to further determine the properties of rehydrated pastes. When the AF-LuCI paste hydrated in simulated gastric fluid (SGF, pH 1.0) was added with pH 3.5 SDF and pH 6.5 SIF, the phase angle of the resultant pastes were higher than 800 indicating that the resultant pastes are in liquid state that is conformable on a surface forming a continuous layer, while the sucralfate paste in pH 1.0 SGF added with SDF or SIF showed significant decrease of phase angle or formed weak brittle solid particles (FIG. 16). This shows that there was no significant change in the phase angle indicating that AF-LuCI forms liquid in pH-independent manner. The phase angle of acidified sucralfate paste drastically decreased in SDF (pH 3.5) forming weak solid aggregates. Thus, the AF-LuCI can be hydrated into a conformable viscous paste independent to the location in GI tract unlike the native sucralfate that formed particulate aggregates in stomach and didn't attach on duodenum and intestine. This pH-independent hydration behavior is due to the shorter PAC in AF-LuCI that is easier to solubilize in water and thus more accessible to form complex coacervate with the anions compared to the water-insoluble PAC of native sucralfate with higher degree of polymerization.

Figure 17:
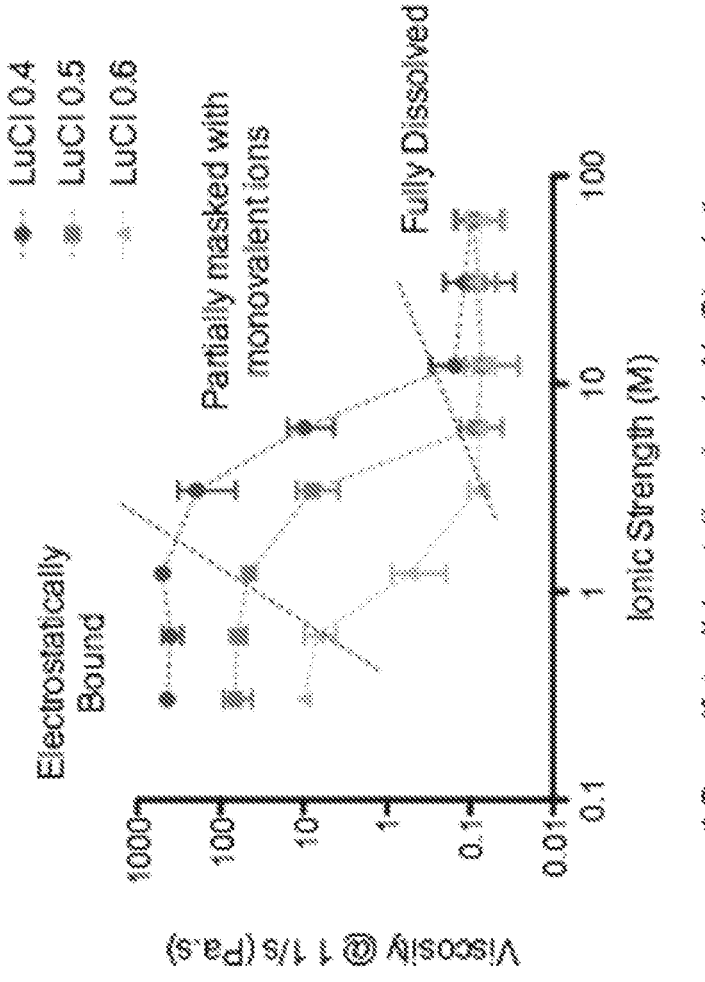
FIG. 17 is a graph showing change of viscosity of re-hydrated AF-LuCI in NaCl solutions with different ionic strength.

When AF-LuCI powders were added with NaCl solutions in different concentrations, they were gradually swollen with increasing NaCl concentrations to form a lower viscosity liquid due to partial masking of charged polymers with monovalent ions, and fully dissolved in higher concentration NaCl solutions above a certain critical level (FIG. 17). FIG. 17 shows that with increasing ionic strength, the viscosity of re-hydrated AF-LuCI pastes decreased due to partial masking of charged groups in PAC and sucrose octasulfate of AF-LuCI, and fully dissolved in NaCl solutions with ionic strength higher than a certain critical point. This is a characteristic behavior of complex coacervate system. This is a characteristic behavior of liquid complex coacervate system (See Wang, Q. & Schlenoff, J. B. The Polyelectrolyte Complex/Coacervate Continuum. Macromolecules 47, 3108-3116 (2014); de Kruif, C. G., Weinbreck, F. & de Vries, R. Complex coacervation of proteins and anionic polysaccharides. Current Opinion in Colloid & Interface Science 9, 340-349 (2004); Veis, A. & Aranyi, C. PHASE SEPARATION IN POLYELECTROLYTE SYSTEMS. I. COMPLEX COACERVATES OF GELATIN. J. Phys. Chem. 64, 1203-1210 (1960)). It indicates that the shorter and more hydrated PAC could form more flexible linkages with the anionic sucrose octasulfate forming the viscous liquid. AF-LuCI fabricated in higher concentration HCl required lower concentration NaCl solution to fully dissolve AF-LuCI (i.e. fully dissociate the PAC and sucrose octasulfate) suggesting that the shorter PAC has lower ionic binding energy contributing to its lower viscosity. Less than 5 w/w % of the native sucralfate was dissolved even in saturated NaCl solutions (~0.35 g/ml in water) and the remaining sucralfate remained suspended indicating that in the native sucralfate the two polyions are bound too strongly together and becomes liquid paste phase only with large amount of stomach acid that extensively breaks down the PAC.

Example 12—AF-LuCI Coating can Lower Glucose Response in Rats

Experiments were performed to assess how AF-LuCI forms a coating in vivo.

Figure 18C:
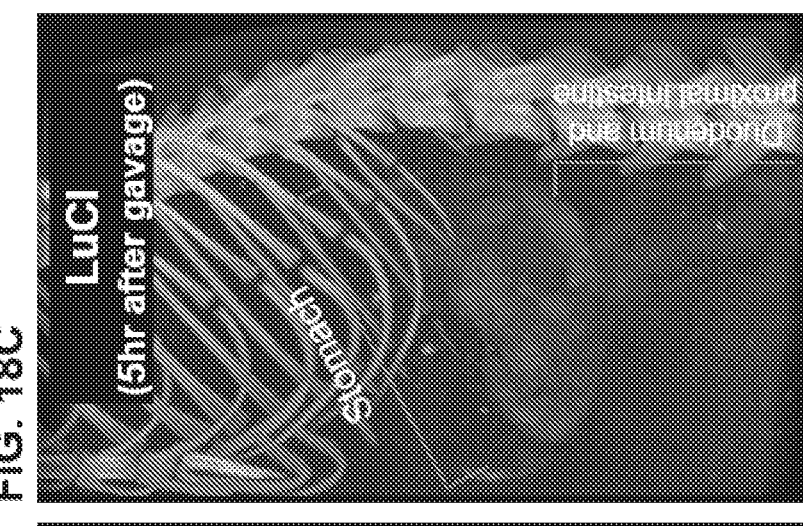
FIGS. 18A, 18B, and 18C are images from micro-computed tomography (microCT) showing the behavior of AF-LuCI gavaged into a rat stomach.
Figure 18B:
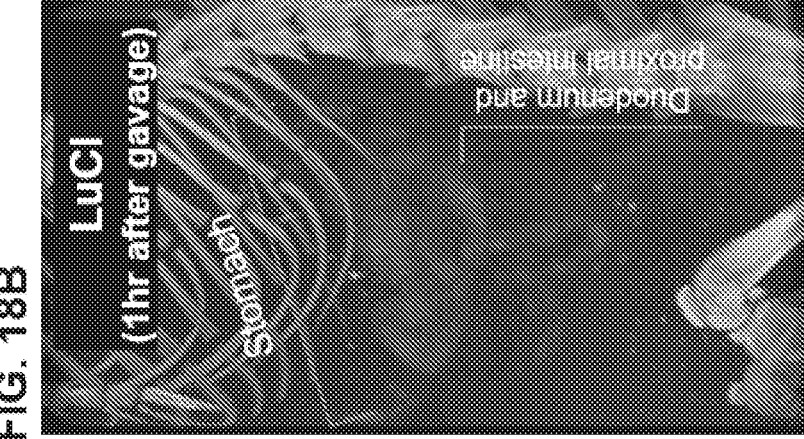
Figure 18A:
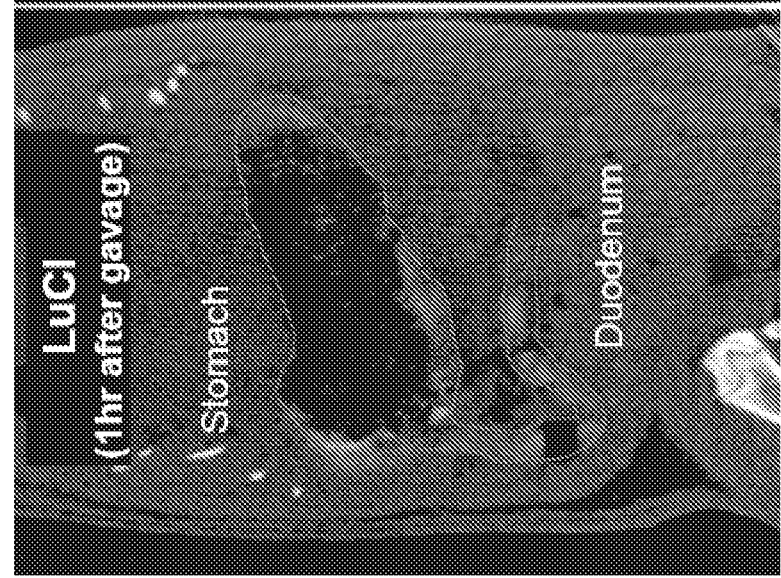

Sprague-Dawley (SD) rats were gavaged into the stomach with hydrated AF-LuCI pastes and imaged using micro-computed tomography (microCT). AF-LuCI pastes could be visualized on gastro-intestinal tissues without additional contrast agents owing to the presence of aluminum. For these experiments, rats were fasted overnight and gavaged directly into the stomach with 450 mg/kg rat of AF-LuCI paste hydrated in 0.9 w/v % normal saline solution. After 1 hr and 5 hr, the rats were anesthetized using isoflurane and imaged using microCT. The images showed that the AF-LuCI pastes formed a layer in the stomach and duodenum after 1 hr of the gavage and the layer was stable for the extent of the study (5 hr) (FIGS. 18A-18 C). FIG. 18A is a coronal plane view of SD rats gavaged with AF-LuCI 1 hr before the imaging. AF-LuCI formed a layer in stomach, duodenum and proximal intestine. FIGS. 18B and 18C are 3-dimentional views of SD rats gavaged with AF-LuCI (FIG. 18B) 1 hr and (FIG. 18C) 5 hr before the microCT imaging. AF-LuCI is attached on stomach, duodenum and proximal intestine at least for 5 hrs after gavage while sucralfate only formed sparsely scattered aggregates on the healthy mucosa When sucralfate was gavaged to SD rats, the microCT images only showed small aggregates on stomach and intestinal areas suggesting that the sucralfate did not form a layer. These data suggest that the AF-LuCI can form a coating on the luminal side of the GI tract with transient stability.

Figures 19A, 19B, 19C:
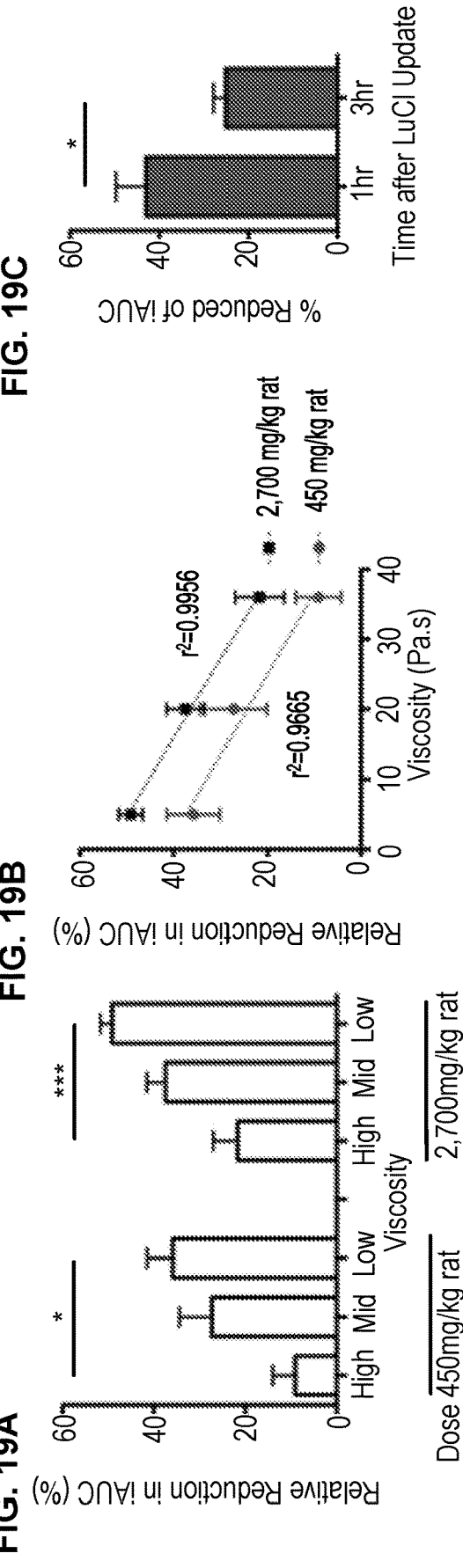
FIG. 19A is a graph showing reduction of glucose responses in incremental Area Under the Curve (iAUC) of Sprague Dawley (SD) rats gavaged with AF-LuCI pastes in different viscosities and doses.
FIG. 19B is a graph showing correlation between the AF-LuCI viscosity in two different doses (450 and 2,700 mg/kg) and iAUC.
FIG. 19C is a graph showing percentage reduction of iAUC in oral glucose tolerance test (OGTT) with different AF-LuCI dosing schedule.

Experiments were then performed to assess if the AF-LuCI coating could lower glucose response. To evaluate the in vivo effect of the barrier coating from AF-LuCI on postprandial glucose response, SD rats were pre-gavaged with the AF-LuCI pastes and standard OGTT was performed. AF-LuCI at different dosage but also different viscosity. It was hypothesized that low viscosity product may lead to barrier formation in larger area and earlier duodenal coating (onset of action). For these studies, rats were fasted overnight and gavaged with AF-LuCI pastes (dose: 450-2,700 mg/kg rat; viscosity: high and low), or saline as a control. One or three hours later, glucose solution (2 g/kg rat) was gavaged and changes in serum glucose levels measured every 30 minutes over the subsequent 120 min (n=4 per arm). Tail vein blood was used to measure glucose levels using glucometer. The viscosity of the AF-LuCI paste had a significant impact on the reduction of blood glucose response (FIGS. 19A and 19B). The AF-LuCI formulation that forms a lower viscosity paste (viscosity: 5 Pa·s, 15% reduction with 450 mg/kg rat dose) showed significantly higher reduction of blood glucose responses compared to higher viscosity paste (viscosity: 36 Pa·s, 3% reduction with 450 mg/kg rat dose). The higher viscosity paste (36 Pa·s) exhibits a similar viscosity with the paste formed from native sucralfate by reacting with SGF. The time gap between AF-LuCI administration and glucose gavage also affects the reduction of blood glucose responses differently depending on the AF-LuCI formulations (FIG. 19C). 3 hr after treatment with 450 mg/kg rat lower viscosity AF-LuCI (i.e. 5 Pa·s), the reduction in glucose response decreased to 7%. In FIG. 19, AF-LuCI fabricated using 0.4N, 0.5N, and 0.6N HCl solution and rehydrated in 0.9 w/v % normal saline is denoted as "Viscosity High", "Viscosity Mid", and "Viscosity Low", respectively.

These results suggest that the oral administration of AF-LuCI can effectively lower the glucose response and the reduction in glucose responses can be maximized by altering physical properties of AF-LuCI (e.g., viscosity) that potentially modulates the coating properties (e.g., duration and location of coating).

In contrast, sucralfate selectively binds to ulcerated mucosa where the bicarbonate secretion is malfunctioned (i.e. acidic), while on bicarbonate-neutralized healthy mucosa sucralfate forms loosely bound discrete solid aggregates attached on the surface rather than forming a continuous layer. Computed tomography (CT) images and fluorescent microscopy images of the rats gavaged with sucralfate showed that sucralfate was sparsely scattered in the stomach and intestine in low density and washed out in a few hours. The neutralized pH on mucus surfaces also compromised the barrier function of sucralfate due to the change of rheological properties. When acidified sucralfate paste was added with solutions with pH higher than 1.0, the phase angle ($\delta$) in oscillatory rheological analysis gradually increased indicating the formation of weak solid aggregates. Furthermore, when sucralfate was applied on the mucus-coated membrane in pH 1.0 and added with solutions with higher pH (>2.0), the barrier function steeply decreased (16.5% glucose blocked in pH 4.0). As a result, when sucralfate was tested in oral glucose tolerance tests (OGTT) using normal Sprague-Dawley (SD) rats, the peak glucose values were similar at all other time points except for one time point at 5 min and there was no significant difference in the area under curve (AUC) between sucralfate and saline treated groups. These results suggest that AF-LuCI are more effective than sucralfate for lowering glucose response.

Example 13—AF-LuCI Coating Lowers Glucose Response Through Physical Barrier Effect Experiments were also performed to determine whether AF-LuCI coating has effect on glucose responses only through physical barrier effect and not through systemic effect. Rats were gavaged with AF-LuCI in the dose with the maximum effect (low viscosity, 450 mg/kg rat), and high dose glucose (2 g/g rat) was administered after an hour either through oral gavage (for OGTT) or through intraperitoneal injection (for IpGTT). In OGTT (FIG. 19D), the blood glucose responses were significantly reduced (FIG. 19E), and iAUC were reduced by 47.3% (FIG. 19F). In IpGTT (FIG. 19G), there was no difference in glucose responses in IpGTT curves (FIG. 19H), and in iAUC (FIG. 19I), suggesting that reduction of glucose response is through localized barrier coating but not through systemic effect.

Example 14—Method for Making a Hydratable Composition Including a Biologically Active Substance The following method was used to fabricate an AF-LuCI particle composition that includes a biologically active substance yet still forms a viscous sticky paste in water without requirement of acid.

One gram of sucralfate (Heisen Pharmaceutical, China) was added in a 20 ml glass vial, added with 10 ml of 0.1-1.0N HCl solutions in water, and immediately vortexed in 3000 rpm for 10 seconds to form a viscous precipitation.

The supernatant solution was removed and 10 ml of methanol, ethanol, isopropanol, or crude reagent alcohol was added. The vial was vortexed in 3000 rpm for 30 seconds to obtain a white particle suspension. The particles were precipitated using centrifugation (1000 rpm for 1 minute) or gravitational precipitation and the supernatant was removed.

In another test, instead of using solvents to dehydrate the acidified sucralfate paste, microwave-assisted drying was used to prepare AF-LuCI particles. One gram of sucralfate (Heisen Pharmaceutical, China) was added in a 20 ml glass vial, added with 10 ml of 0.1-1.0 N HCl solutions in water, and immediately vortexed in 3000 rpm for 10 seconds to form a viscous precipitation. The microwave drying process was performed with a microwave oven (power: 800 W) for 30 seconds.

The white particles were further dried using air-drying for more than 12 hours or under vacuum for at least 1 hour. The dried particles were ground using a mortar and pestle to formulate into white powders. The powders were stored in a closed glass vial in room temperature before mixing with biologically active agents. The chemical status of sucralfate and AF-LuCI particles were evaluated using FT-IR (Bruker, measured from 500 cm-1 to 4000 cm-1 in wavenumber) and TGA (Perkin Elmer, measured from 20° C. to 800° C.).

One milligram of dry HRP powder was homogeneously mixed with 50 mg of AF-LuCI (Formulation A, target loading 2% w/w) in a 2 ml Eppendorf tube and hydrated using 1 ml of PBS (pH 7.4). The supernatant was removed and washed three times with PBS. To calculate the loading efficiency, HRP concentration in the supernatant and each washing buffer was measured using mBCA (loading efficiency, ~84%). In a second formulation (Formulation B), HRP solution (1 mg of HRP in 1 ml of PBS) was added to hydrated LuCI (dry weight, 50 mg), vortexed for 1 minute and washed with PBS three times (loading efficiency, ~80%). In a third formulation (Formulation C), HRP solution (1 mg of HRP in 1 ml of PBS) was added to dry LuCI powder (50 mg), vortexed for 1 minute and washed with PBS three times (loading efficiency, ~99%).

Example 15—LuCI Coating Protects Biologically Active Substance from an Acid Environment Experiments were also performed to show delivery of a biomolecule using LuCI and the ability of a LuCI formulation to protect a protein against degradation in stomach acid (FIG. 20A). In this test, the Horse Radish Peroxidase (HRP)-specific substrate 3,3', 5,5'-tetramethylbenzidine (TMB) was used to measure the activity of HRP encapsulated in LuCI before and after an acid treatment with Simulated Stomach Fluid (SSF), which has a pH of 1.0.

Dry HRP powder (1 mg) was homogeneously mixed with 2 g of dry LuCI powder and hydrated using Hank's balanced salt solution (HBSS). HRP-loaded LuCI (20 μl) was transferred to a 96-well plate (total amount of HRP, 8 μg, calculated using the hydrated volume per dry weight of LuCI). SSF (50 μl, pH 1.0) was added to HRP-loaded LuCI and incubated at 37° C. for 1 hour. The SSF was removed and the LuCI paste washed three times with HBSS. The TMB substrate (liquid substrate, supersensitive for ELISA (Sigma-Aldrich)) was used to test the activity of HRP following the manufacturer's manual. Briefly, 50 μl of TMB substrate was added to the LuCI, incubated for 5 minutes in a shaking incubator (37° C.) and the reaction was stopped using 50 μl of 2.0 N HCl solution in water that also fully dissolved LuCI. The color change of the resultant solution was measured in a plate reader using a wavelength of 420 nm. HBSS, HRP solution, or LuCI without HRP loading were used as the controls. Micro-BCA (mBCA) was used to measure the amount of HRP that remained in LuCI before and after the SSF treatment.

Figure 20C:
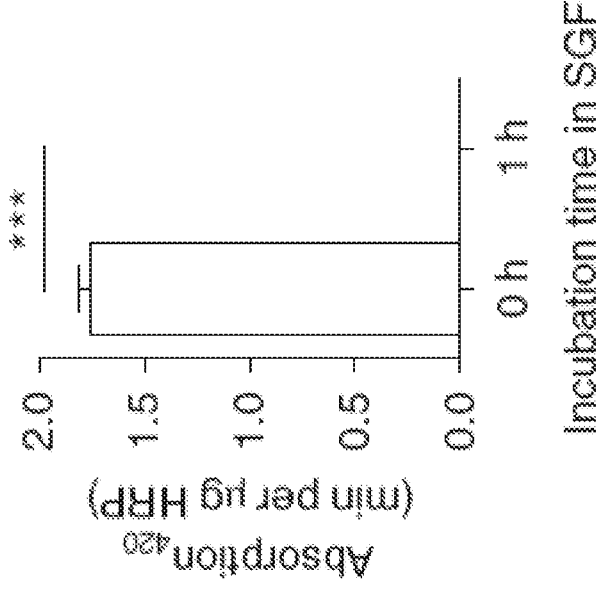
FIG. 20C is a bar graph that shows HRP activity (without any LuCI or other carrier) before and after a one hour incubation in a simulated stomach fluid (pH 1.0). Student t-test (two-tailed, ***P<0.0001).
Figure 20B:
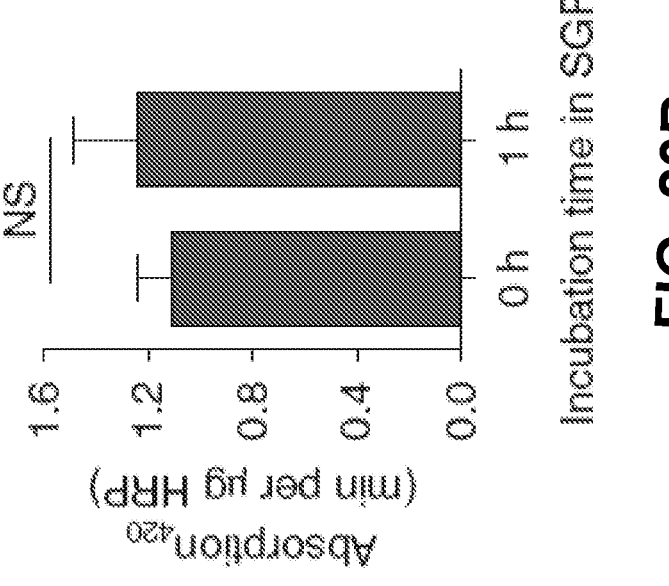
FIG. 20B is a bar graph that shows horse radish peroxidase (HRP) activity protected by a LuCI composition before and after a one hour treatment in a simulated stomach fluid (pH 1.0) normalized by the remaining amount of HRP activity. Student t-test (two-tailed).

The results of this example demonstrated that the LuCI formulation was able to protect a loaded protein from degradation by stomach acid. The HRP that remained loaded in the LuCI showed a similar activity before and after the acid treatment (FIG. 20B), whereas naked HRP exposed to the acid showed a complete loss of activity (FIG. 20C).

This example effectively showed LuCI's ability to protect a biomolecule from the harsh microenvironment of the stomach, and to maintain the biological activity.

Example 16—Release of Biologically Active Substance from Different LuCI Formulations Further experiments were performed to show the ability of LuCI to release a biologically active substance with different LuCI formulations. For this release study, 1 mg of dry HRP powder was homogeneously mixed with 50 mg of LuCI (Formulation A, target loading 2% w/w) in a 2 ml Eppendorf tube and hydrated using 1 ml of PBS (pH 7.4). The supernatant was removed and washed three times with PBS. To calculate the loading efficiency, HRP concentration in the supernatant and each washing buffer was measured using mBCA (loading efficiency, ~84%). In a second formulation (Formulation B), HRP solution (1 mg of HRP in 1 ml of PBS) was added to hydrated LuCI (dry weight, 50 mg), vortexed for 1 minute and washed with PBS three times (loading efficiency, ~80%). In a third formulation (Formulation C), HRP solution (1 mg of HRP in 1 ml of PBS) was added to dry LuCI powder (50 mg), vortexed for 1 minute and washed with PBS three times (loading efficiency, ~99%).

The washed LuCI was combined with 1 ml of PBS and incubated in a shaking incubator (37° C.) for predetermined time points. The release buffer was collected and replaced with 1 ml of PBS. The time points were 5 min, 30 min, 1 hour, 2 hours, 4 hours, 8 hours and 24 hours. The HRP concentration of each release buffer was measured using mBCA. The HRP releases of Formulations B and C were tested using the same method and time points described above.

Figure 20D:
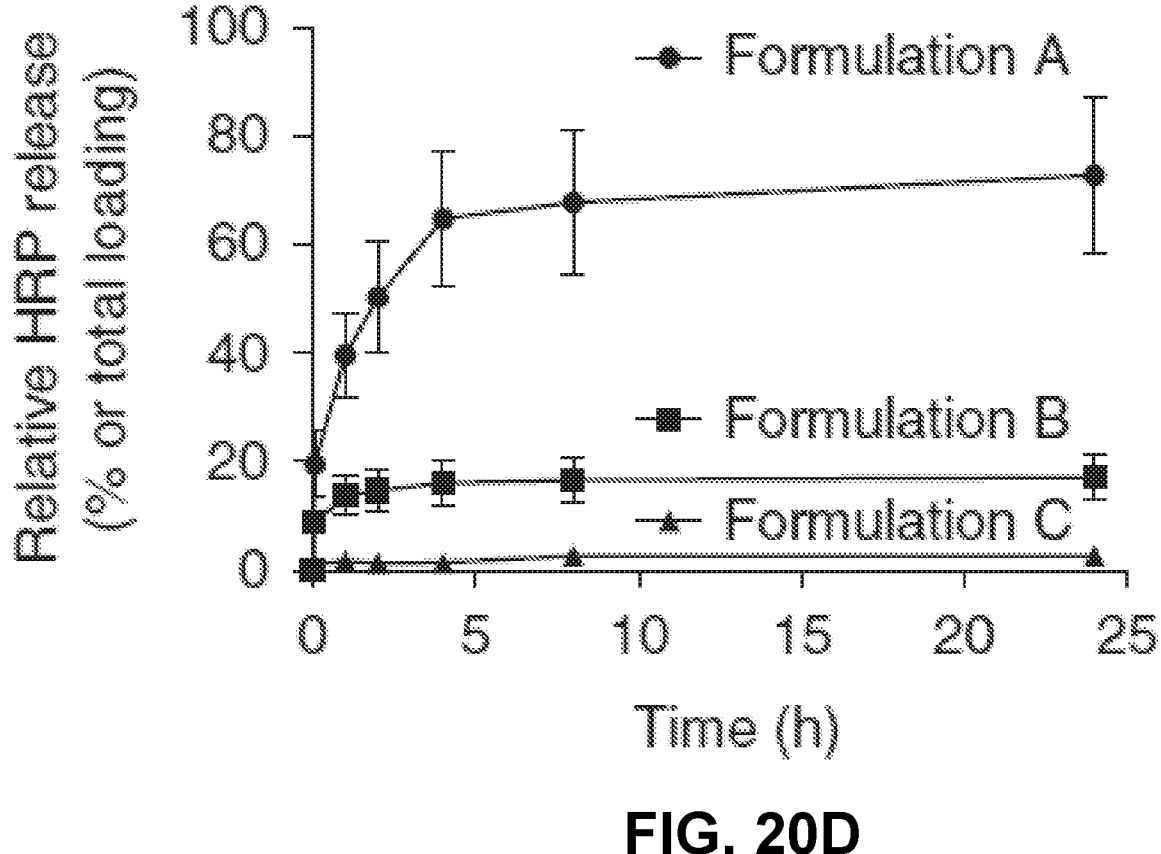
FIG. 20D is a graph that shows the release of HRP from LuCI using different formulations. Formulation A: dry LuCI powder mixed in dry HRP powder. Formulation B: dry LuCI powder+HRP solution in PBS (pH 7.4). Formulation C: hydrated LuCI paste in PBS (pH 7.4)+HRP solution in PBS (pH 7.4).

For Formulation A, when dry HRP powder was directly mixed with dry LuCI powder (loading, 2% w/w in LuCI; loading efficiency, 84%), ~62% of the loaded HRP was gradually released from the LuCI during the first four hours and an additional ~10% of the HRP was released over the course of 24 hours (see FIG. 20D). However, as further shown in FIG. 20D, for Formulation B, which was dry LuCI powder mixed with the HRP solution in PBS (pH 7.4), ~18% of the loaded HRP was gradually released from the LuCI during the first four hours and little additional of the HRP was released over the course of 24 hours. For Formulation C, which was hydrated LuCI paste in PBS (pH 7.4) plus the HRP solution in PBS (pH 7.4), essentially none of the loaded HRP was released from the LuCI during the first four hours, and then only 1% or 2% of the HRP was released over the course of 24 hours. These results may be explained by the expected larger pore formation in the LuCI of Formula A.

Example 17—LuCI Formulations Coat the Entire GI Tract for 24 Hours

When the dry-mixture formulation of LuCI loaded with a fluorescent-tagged model protein (fluorescein isothiocyanate (FITC)—albumin) was gavaged into rats, the protein cargo was delivered to the duodenum and small intestine starting within the first hour after administration and the protein remained in the GI tract for 24 hours.

In particular, SD rats were gavaged with LuCI (dose: 450 mg/kg rat) encapsulated with FITC-BSA (2 w/w % in LuCI powder), and the GI tracts from stomach to cecum were harvested after 1 hour or 24 hours. The harvested GI tracts were imaged using IVIS Spectrum In Vivo Imaging System (Perkin Elmer). Rats without LuCI gavage were used as a control and all the images were normalized using the control.

Figures 21A, 21B, 21C:
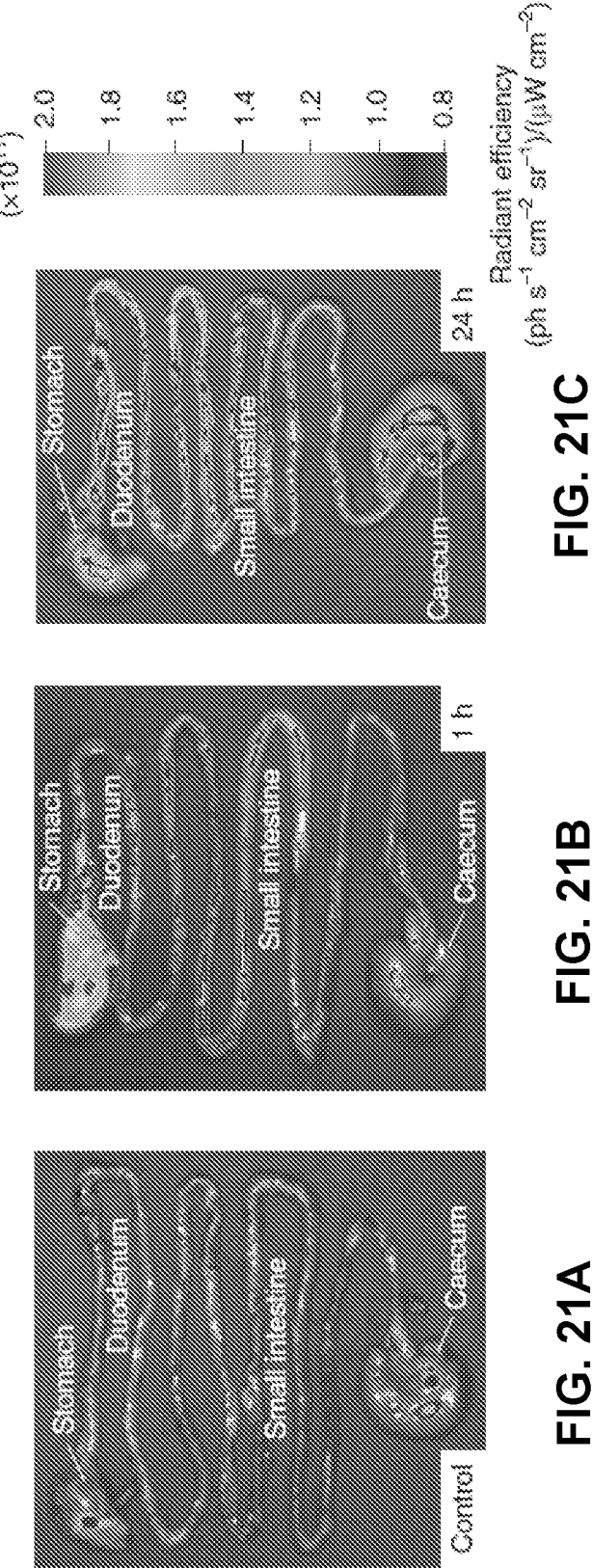
FIGS. 21A-21C are a series of fluorescent images that show the results of IVIS analysis to track the fluorescence-tagged model protein (FITC-albumin) encapsulated in LuCI as it passed through the GI tract in a rat.
Figure 22:
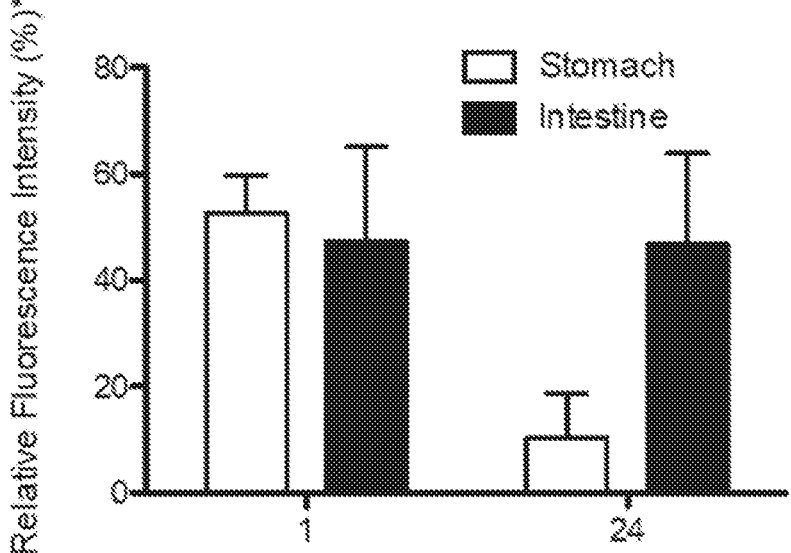
FIG. 22 is a bar graph that shows relative fluorescence intensity for 24 hours after the administration of LuCI encapsulated FITC-BSA.

A fluorescence signal from the model protein was detected mostly in the stomach and duodenum after one hour (FIG. 21), and detected in the duodenum and small intestine even after 24 hours (FIG. 21C). The control shows no signal (FIG. 21A). As shown in the bar graph of FIG. 22, the total fluorescence intensity was maintained at a similar level in the intestine from 1 to 24 hours, while the intensity of total fluorescence in the stomach significantly decreased from 1 hour to 24 hours. Overall, $46.8 \pm 24.1\%$ of the fluorescence signal was retained in the gut compared to the total fluorescence found after 1 hour.

These experiments showed that LuCI protected and delivered a biomolecule through the stomach into the intestines and maintained the protein in the small intestines for up to 24 hours.

Example 18—LuCI Coating Used to Deliver Another Biologically Active Substance A metformin release study was done to further investigate the ability of LuCI formulations to deliver biologically active substances to the small intestines.

In this example, 10, 20, 30, or 40 mg of metformin hydrochloride (Sigma Aldrich) powder was homogeneously mixed with 100 mg of LuCI (target loading 1:10, 2:10, 3:10, 4:40 w/w, respectively) in a 2 ml Eppendorf tube and hydrated using 1 ml of PBS (pH 7.4). The supernatant was removed and washed 3 times with PBS. To calculate the loading efficiency, metformin concentration in supernatant and each washing buffer was measured using high performance liquid chromatography (HPLC). The washed LuCI was combined with 1 ml PBS and incubated in a shaking incubator (37° C.) for predetermined time points. The release buffer was collected and replaced with 1 ml PBS. The time points were 5 minutes, 30 minutes, 1 hour, 2 hours, 4 hours, 24 hours, 48 hours, and 72 hours. The metformin concentration of each release buffer was measured using HPLC. The percentage release is calculated based on the initial loading amount.

Figure 23A:
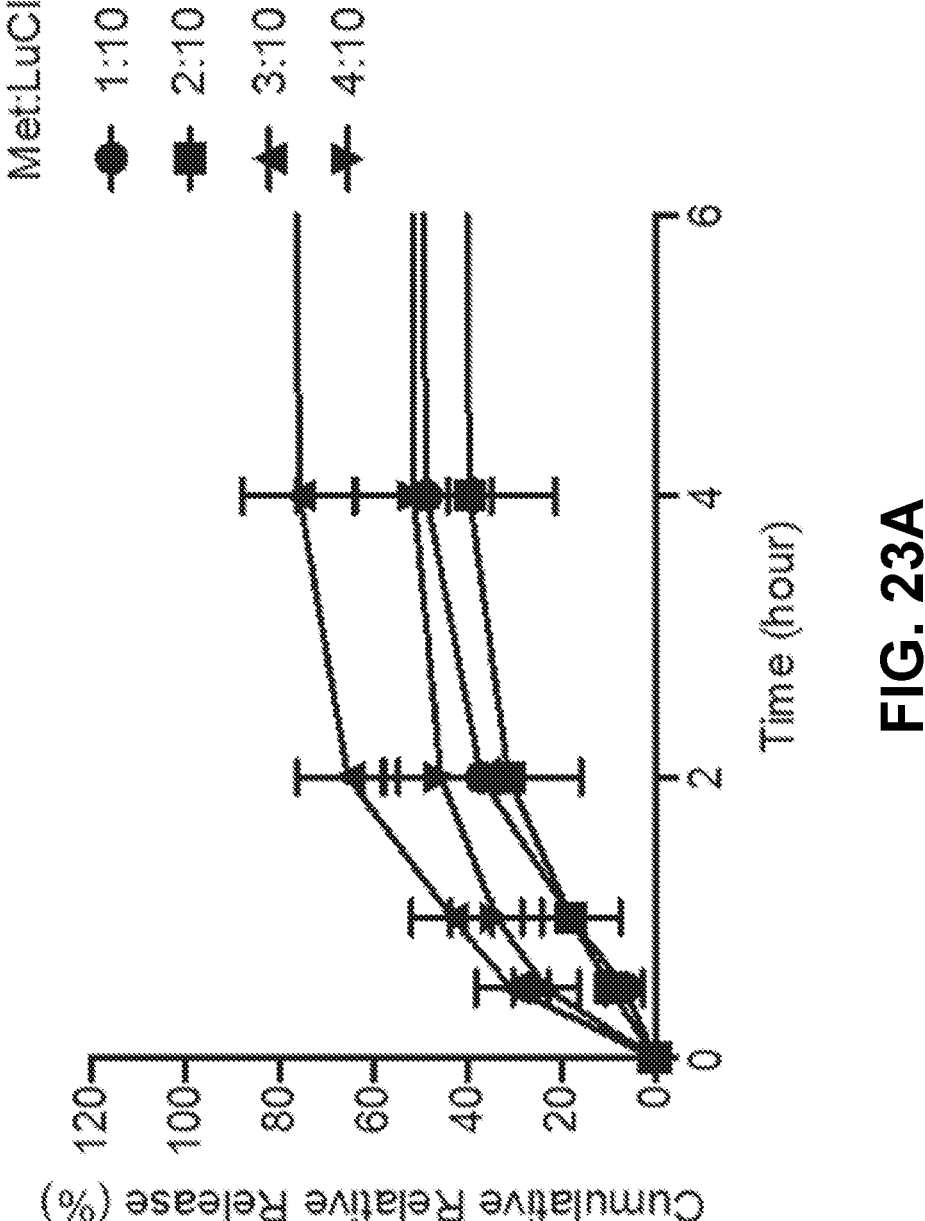
FIG. 23A is a graph that shows metformin release over time for different ratios of Metformin to LuCI.
Figure 23B:
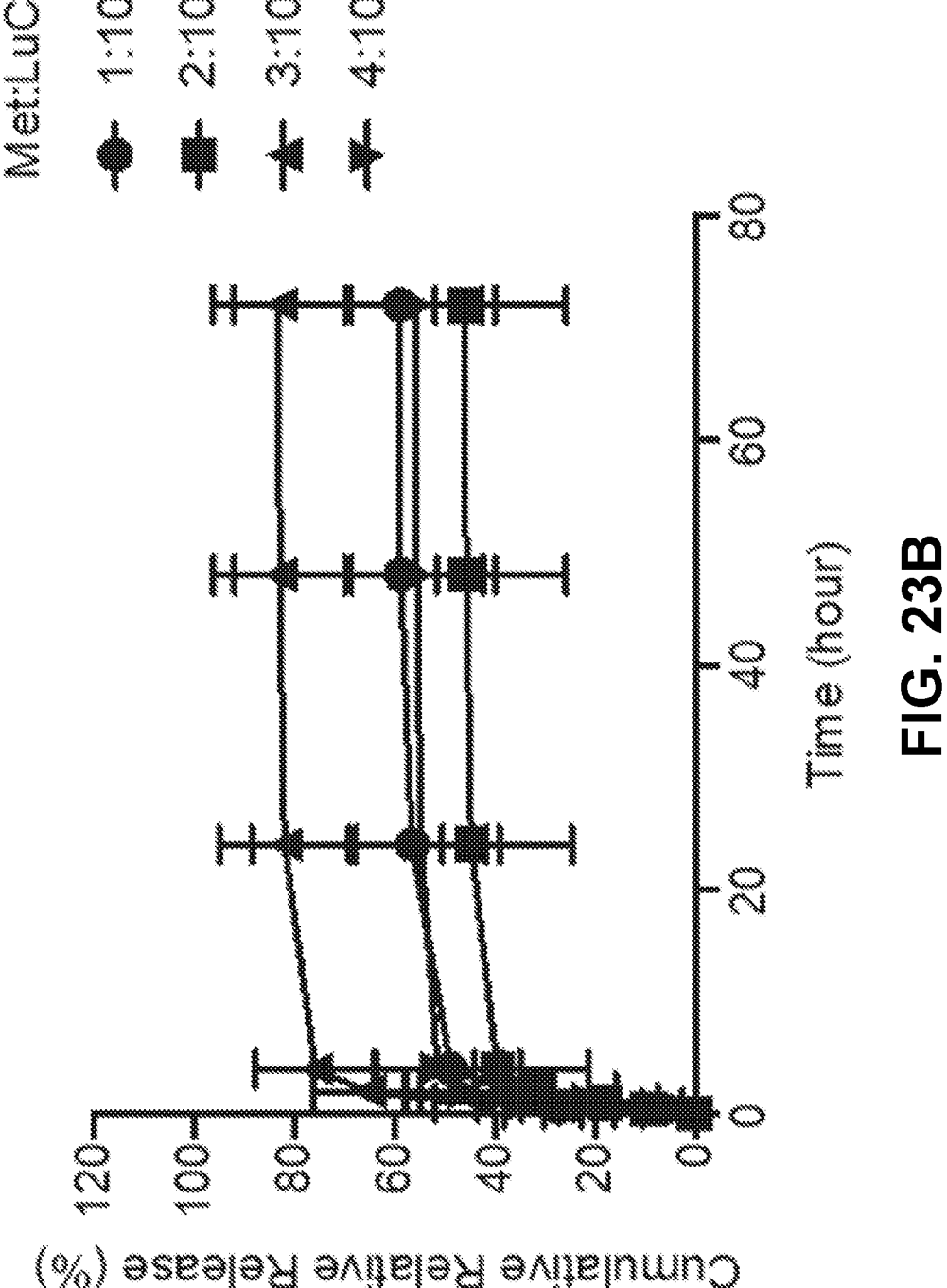
FIG. 23B is a close up of the graph that shows metformin release over time for different ratios of Metformin to LuCI (showing the first 6 minutes of FIG. 22A).

As shown in FIGS. 23A and 23B, all ratios used led to release of metformin from LuCI. Metformin release was consistent through at least 72 hours after the Metformin was loaded into LuCI. As shown in FIG. 23A, which shows the results in the first 6 hours, most of the metformin was released within this timeframe. As shown in FIG. 23B, not much additional metformin was released for the remaining hours to the time point of 72 hours.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of making a stable, sulfated agent hydratable composition including a biologically active substance, the method comprising:

mixing a sulfated agent with an acid solution to form a viscous precipitate, wherein the sulfated agent comprises one or more of sucralfate, sulfated dextran, sulfated dextrin, sulfated amylopectin, sulfated amylose, sulfated cellulose, carrageenan, chondroitin sulfate, glucose sulfate, sucrose sulfate, heparin, heparin sulfate, or raffinose sulfate;

mixing the viscous precipitate with a sufficient amount of a water-miscible or water-soluble solvent for a time sufficient to obtain a particle suspension;

dehydrating the particle suspension by removing particles from the particle suspension by precipitation to obtain a stable, sulfated agent hydratable composition of dry particles;

forming the dry particles into a dry powder; and mixing the dry powder with one or more biologically active substances, in dry powder form, and thereafter hydrating the resulting powder mixture with a pharmaceutically acceptable carrier liquid, wherein the one or more biologically active substances comprise one or more proteins.

2. The method of claim 1, wherein the acid solution comprises a 0.1-1.0 N HCl solution and the sufficient amount of the water-miscible or water-soluble solvent comprises at least 30 v/v % of the water-miscible solvent.

3. The method of claim 1, wherein the one or more biologically active substances are protected from acid in a subject's stomach and maintain at least 10% of their biological activity when present in the intestines after passing through the subject's stomach.

4. The method of claim 1, wherein the sulfated agent comprises sucralfate.

5. The method of claim 1, wherein the water-miscible or water-soluble solvent comprises one or more of an alcohol, acetone, dimethyl sulfide (DMSO), N,N-dimethyl formamide (DMF), acetonitrile, 1,4-dioxane, tetrahydrofuran (THF), acetic acid, acetaldehyde, 1,2-butandiol, 1,3-butandiol, 1,4-butandiol, butyric acid, diethanolamine, diethylenetriamine, dimethoxyethane, ethylamine, ethylene glycol, formic acid, glycerol, methyl diethanolamine, methyl isocyanide, 1,3-propanediol, 1,5-pentanediol, propanoic acid, propylene glycol, pyridine, or triethylene glycol.

6. The method of claim 5, wherein the water-miscible or water-soluble solvent comprises alcohol.

7. The method of claim 6, wherein the alcohol comprises one or more of methanol, ethanol, isopropanol, n-propanol, reagent alcohol, 2-butoxiethanol, or furfuryl alcohol.

8. The method of claim 5, wherein the water-miscible or water-soluble solvent comprises DMSO.

9. The method of claim 1, wherein the acid solution comprises one or more of hydrochloric acid (HCl), hydroiodic acid (HI), hydrobromic acid (HBr), perchloric acid ($HClO_4$), nitric acid ($HNO_3$), or sulfuric acid ($H_2SO_4$).

10. The method of claim 9, wherein the acid solution comprises HCl at a concentration of 0.1 N to 1.0 N.

11. A method of making a stable, sulfated agent hydratable composition including a biologically active substance, the method comprising:

mixing a sulfated agent with an acid solution to form a viscous precipitate, wherein the sulfated agent comprises one or more of sucralfate, sulfated dextran, sulfated dextrin, sulfated amylopectin, sulfated amylose, sulfated cellulose, carrageenan, chondroitin sulfate, glucose sulfate, sucrose sulfate, heparin, heparin sulfate, or raffinose sulfate;

preparing a particle suspension by mixing the viscous precipitate with a water-soluble solvent or a water-miscible solvent;

removing particles from the particle suspension by precipitation to obtain dry particles;

forming the dry particles into a dry powder; and mixing the dry powder with a biologically active substance in dry powder form, and thereafter hydrating the resulting powder mixture with a pharmaceutically acceptable carrier liquid, wherein the biologically active substance comprises a protein.

12. The method of claim 11, wherein the acid solution comprises a 0.1-1.0 N HCl solution and the water-soluble solvent or the water-miscible solvent comprises at least 30 v/v % of the water-miscible solvent.

13. The method of claim 11, wherein the one or more biologically active substances are protected from acid in a subject's stomach and maintain at least 10% of their biological activity when present in the intestines after passing through the subject's stomach.

14. The method of claim 11, wherein the sulfated agent comprises sucralfate.

15. The method of claim 11, wherein the water-soluble solvent or the water-miscible solvent comprises one or more of an alcohol, acetone, dimethyl sulfide (DMSO), N,N-dimethyl formamide (DMF), acetonitrile, 1,4-dioxane, tetrahydrofuran (THF), acetic acid, acetaldehyde, 1,2-butandiol, 1,3-butandiol, 1,4-butandiol, butyric acid, diethanolamine, diethylenetriamine, dimethoxyethane, ethylamine, ethylene glycol, formic acid, glycerol, methyl diethanolamine, methyl isocyanide, 1,3-propanediol, 1,5-pentanediol, propanoic acid, propylene glycol, pyridine, or triethylene glycol.

16. The method of claim 15, wherein the water-soluble solvent or the water-miscible solvent comprises alcohol.

17. The method of claim 16, wherein the alcohol comprises one or more of methanol, ethanol, isopropanol, n-propanol, reagent alcohol, 2-butoxiethanol, or furfuryl alcohol.

18. The method of claim 15, wherein the water-soluble solvent or the water-miscible solvent comprises DMSO.

19. The method of claim 11, wherein the acid solution comprises one or more of hydrochloric acid (HCl), hydroiodic acid (HI), hydrobromic acid (HBr), perchloric acid ($HClO_4$), nitric acid ($HNO_3$), or sulfuric acid ($H_2SO_4$).

20. The method of claim 19, wherein the acid solution comprises HCl at a concentration of 0.1 N to 1.0 N.

* * * * *